(12) United States Patent
Boss et al.

US010307464B2

(10) Patent No.: US 10,307,464 B2
(45) Date of Patent: *Jun. 4, 2019

(54) USE OF ULTRARAPID ACTING INSULIN

(71) Applicant: MannKind Corporation, Valencia, CA (US)

(72) Inventors: Anders Hasager Boss, Princeton, NJ (US); Richard Petrucci, New Canaan, CT (US)

(73) Assignee: MannKind Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/300,239

(22) PCT Filed: Mar. 27, 2015

(86) PCT No.: PCT/US2015/022956
§ 371 (c)(1),
(2) Date: Sep. 28, 2016

(87) PCT Pub. No.: WO2015/148905
PCT Pub. Date: Oct. 1, 2015

(65) Prior Publication Data
US 2017/0189492 A1    Jul. 6, 2017

(51) Int. Cl.
*A61K 38/28* (2006.01)
*A61K 31/155* (2006.01)
*A61K 9/00* (2006.01)

(52) U.S. Cl.
CPC .............. *A61K 38/28* (2013.01); *A61K 9/007* (2013.01); *A61K 9/0075* (2013.01); *A61K 31/155* (2013.01); *A61K 9/0019* (2013.01)

(58) Field of Classification Search
CPC .................................................... A61K 38/28
See application file for complete search history.

(56) References Cited

U.S. PATENT DOCUMENTS

| | | |
|---|---|---|
| 2,549,303 A | 4/1951 | Friden |
| 2,754,276 A | 7/1956 | Joseph et al. |
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,673,698 A | 7/1972 | Guerard |
| 3,669,113 A | 8/1972 | Altounyan et al. |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |

(Continued)

FOREIGN PATENT DOCUMENTS

| | | |
|---|---|---|
| CA | 2536047 A1 | 3/2005 |
| CA | 2551182 C | 8/2010 |

(Continued)

OTHER PUBLICATIONS

Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat J. Clin. Invest., 95 : 417-421 (1995).

(Continued)

*Primary Examiner* — Gyan Chandra
(74) *Attorney, Agent, or Firm* — K&L Gates LLP; Louis C. Cullman; Hal Gibson

(57) ABSTRACT

Disclosed herein are improved methods of treating hyperglycemia with a combination of an ultrarapid acting insulin and insulin glargine comprising prandial administration of the ultrarapid insulin, and administration of a first dose of insulin glargine within 6 hours of waking for a day.

12 Claims, 18 Drawing Sheets

(56) References Cited

U.S. PATENT DOCUMENTS

| | | |
|---|---|---|
| D269,463 S | 6/1983 | Young et al. |
| 4,407,525 A | 10/1983 | Hoppe |
| 4,456,007 A | 6/1984 | Nakao et al. |
| 4,481,139 A | 11/1984 | Folkers et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,671,954 A | 6/1987 | Goldberg et al. |
| 4,681,752 A | 7/1987 | Melillo |
| D295,321 S | 4/1988 | Hallworth |
| 4,742,156 A | 5/1988 | Wright |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoefling |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Ilium |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,239,993 A | 8/1993 | Evans |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,469,750 A | 11/1995 | Lloyd et al. |
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |

(56) References Cited

U.S. PATENT DOCUMENTS

| | | |
|---|---|---|
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,514,646 A | 5/1996 | Chance et al. |
| 5,518,998 A | 5/1996 | Backstorm et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,715,811 A | 2/1998 | Ohki et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |
| 5,972,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |

(56) References Cited

U.S. PATENT DOCUMENTS

| | | |
|---|---|---|
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffman |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystorm et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| 6,085,745 A | 6/2000 | Levander et al. |
| D428,486 S | 7/2000 | Schuckmann |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,099,517 A | 9/2000 | Daughtery |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,247,598 B1 | 6/2001 | Hosaka et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Schuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstorm et al. |
| 6,357,442 B1 | 3/2002 | Casper et al. |
| 6,358,058 B1 | 3/2002 | Strupat et al. |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelberth et al. |
| 6,443,143 B1 | 9/2002 | Ishida et al. |
| 6,443,307 B1 | 9/2002 | Burridge |
| 6,444,226 B1 | 9/2002 | Steiner et al. |
| 6,446,626 B1 | 9/2002 | Virtanen |
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |

(56) References Cited

U.S. PATENT DOCUMENTS

| | | |
|---|---|---|
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelberth et al. |
| 6,630,169 B1 | 10/2003 | Bat et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman et al. |
| 6,672,304 B1 | 1/2004 | Casper et al. |
| 6,676,931 B2 | 1/2004 | Dugger, III |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B1 | 2/2004 | Patton et al. |
| 6,696,090 B1 | 2/2004 | Nilsson et al. |
| 6,698,421 B2 | 3/2004 | Attolini |
| 6,698,422 B2 | 3/2004 | Fugelsang et al. |
| 6,698,425 B1 | 3/2004 | Widerstorm |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Raul |
| 6,737,045 B2 | 5/2004 | Patton |
| 6,745,761 B2 | 6/2004 | Christup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,794,357 B1 | 9/2004 | Backstrom et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,835,372 B2 | 12/2004 | Kuo et al. |
| 6,838,075 B2 | 1/2005 | Stevenson et al. |
| 6,838,076 B2 | 1/2005 | Platton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliot |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| D511,977 S | 11/2005 | Saelzer |

(56) References Cited

U.S. PATENT DOCUMENTS

| | | |
|---|---|---|
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,105,489 B2 | 9/2006 | Hathaway |
| 7,107,988 B2 | 9/2006 | Pinon et al. |
| 7,109,161 B1 | 9/2006 | Gayed |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| D540,671 S | 4/2007 | Born |
| D541,151 S | 4/2007 | Born |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,265,087 B1 | 9/2007 | Goke et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Mryman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| D566,549 S | 4/2008 | Russell |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,712 B2 | 7/2008 | Kaye et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |
| 7,799,344 B2 | 9/2010 | Oberg |
| 7,803,404 B2 | 9/2010 | Hokenson |
| 7,820,676 B2 | 10/2010 | Leone-Bay et al. |
| D626,836 S | 11/2010 | Lien |
| D628,090 S | 11/2010 | Stuiber et al. |
| 7,833,549 B2 | 11/2010 | Steiner et al. |

(56) References Cited

U.S. PATENT DOCUMENTS

| | | |
|---|---|---|
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |
| D643,308 S | 8/2011 | Bergey |
| D645,954 S | 9/2011 | Hately |
| D647,195 S | 10/2011 | Clarke et al. |
| D647,196 S | 10/2011 | Clarke et al. |
| 8,037,880 B2 | 10/2011 | Zhu et al. |
| 8,037,881 B2 | 10/2011 | Pentafragas |
| 8,039,431 B2 | 10/2011 | Wilson et al. |
| 8,047,203 B2 | 11/2011 | Young et al. |
| D652,322 S | 1/2012 | Stuiber et al. |
| 8,109,267 B2 | 2/2012 | Villax et al. |
| 8,119,593 B2 | 2/2012 | Richardson |
| D655,622 S | 3/2012 | Sadler et al. |
| 8,133,514 B2 | 3/2012 | Milstein |
| 8,146,588 B2 | 4/2012 | Steiner et al. |
| 8,156,936 B2 | 4/2012 | Steiner et al. |
| D659,020 S | 5/2012 | Kemner |
| D659,022 S | 5/2012 | Kemner |
| D660,956 S | 5/2012 | Zuyderhoudt |
| 8,166,970 B2 | 5/2012 | Poole et al. |
| 8,172,817 B2 | 5/2012 | Michaels et al. |
| 8,196,576 B2 | 6/2012 | Kriksunov et al. |
| 8,201,555 B2 | 6/2012 | Chawla |
| 8,202,992 B2 | 6/2012 | Stevenson |
| D663,830 S | 7/2012 | Sears |
| D664,640 S | 7/2012 | Smutney et al. |
| 8,215,300 B2 | 7/2012 | Steiner et al. |
| 8,217,007 B1 | 7/2012 | Schteingart et al. |
| 8,227,409 B2 | 7/2012 | Kraft |
| 8,236,766 B2 | 8/2012 | Schteingart et al. |
| 8,252,916 B2 | 8/2012 | Simard et al. |
| 8,258,095 B2 | 9/2012 | Boss et al. |
| 8,278,308 B2 | 10/2012 | Leone-Bay et al. |
| 8,293,869 B2 | 10/2012 | Bossard |
| 8,314,106 B2 | 11/2012 | Kraft |
| D671,842 S | 12/2012 | Bergey |
| D674,893 S | 1/2013 | Kinsey et al. |
| 8,372,804 B2 | 2/2013 | Richardson |
| 8,377,869 B2 | 2/2013 | Richardson |
| 8,389,470 B2 | 3/2013 | Steiner |
| 8,394,414 B2 | 3/2013 | Steiner et al. |
| 8,408,200 B2 | 4/2013 | Clark et al. |
| 8,420,604 B2 | 4/2013 | Hokenson |
| 8,424,518 B2 | 4/2013 | Smutney |
| 8,485,180 B2 | 7/2013 | Smutney et al. |
| 8,486,894 B2 | 7/2013 | Schteingart et al. |
| 8,499,757 B2 | 8/2013 | Smutney |
| 8,512,932 B2 | 8/2013 | Wilson et al. |
| 8,522,775 B2 | 9/2013 | Malhotra et al. |
| 8,536,131 B2 | 9/2013 | Schteingart et al. |
| 8,538,707 B2 | 9/2013 | Adamo et al. |
| 8,539,946 B2 | 9/2013 | Esteve et al. |
| 8,551,528 B2 | 10/2013 | Grant et al. |
| 8,563,101 B2 | 10/2013 | Spallek |
| 8,636,001 B2 | 1/2014 | Smutney |
| 8,642,548 B2 | 2/2014 | Richardson et al. |
| 8,671,937 B2 | 3/2014 | Steiner et al. |
| 8,677,992 B2 | 3/2014 | Villax |
| 8,763,606 B2 | 7/2014 | Mosier et al. |
| 8,778,403 B2 | 7/2014 | Grant et al. |
| 8,783,249 B2 | 7/2014 | Poole et al. |
| D711,740 S | 8/2014 | Lien |
| 8,808,786 B2 | 8/2014 | Jinks et al. |
| 8,820,324 B2 | 9/2014 | Smith et al. |
| 8,900,555 B2 | 12/2014 | Kuo et al. |
| 8,909,487 B2 | 12/2014 | Adamo et al. |
| 8,925,726 B2 | 1/2015 | Bergey |
| 9,041,925 B2 | 5/2015 | Adamo et al. |
| 9,138,407 B2 | 9/2015 | Caponetti et al. |
| D771,237 S | 11/2016 | Smutney et al. |
| D802,116 S | 11/2017 | Smutney et al. |
| 2001/0020147 A1 | 9/2001 | Staniforth et al. |
| 2001/0039442 A1 | 11/2001 | Gorge et al. |
| 2002/0000225 A1 | 1/2002 | Schuler et al. |
| 2002/0015737 A1 | 2/2002 | Shih et al. |
| 2002/0033177 A1 | 3/2002 | Ohki et al. |
| 2002/0052381 A1 | 5/2002 | Bar-Or et al. |
| 2002/0053344 A1 | 5/2002 | Davies et al. |
| 2002/0053347 A1 | 5/2002 | Ziaee |
| 2002/0065239 A1 | 5/2002 | Caplan et al. |
| 2002/0088462 A1 | 7/2002 | Genova et al. |
| 2002/0101590 A1 | 8/2002 | Shimaoka |
| 2002/0144680 A1 | 10/2002 | Nilsson et al. |
| 2002/0161001 A1 | 10/2002 | Kanstrup et al. |
| 2003/0000524 A1 | 1/2003 | Andersson et al. |
| 2003/0010794 A1 | 1/2003 | Herdtle et al. |
| 2003/0013641 A1 | 1/2003 | Steiner et al. |
| 2003/0017211 A1 | 1/2003 | Steiner |
| 2003/0053960 A1 | 3/2003 | Heijerman et al. |
| 2003/0064097 A1 | 4/2003 | Patel et al. |
| 2003/0068378 A1 | 4/2003 | Chen et al. |
| 2003/0099636 A1 | 5/2003 | Epshtein et al. |
| 2003/0136405 A1 | 7/2003 | Goede et al. |
| 2003/0168370 A1 | 9/2003 | Merboth et al. |
| 2003/0194420 A1 | 10/2003 | Holl et al. |
| 2003/0216542 A1 | 11/2003 | Patton et al. |
| 2003/0235538 A1 | 12/2003 | Zirenberg |
| 2004/0022861 A1 | 2/2004 | Williams et al. |
| 2004/0024180 A1 | 2/2004 | Drauz |
| 2004/0025875 A1 | 2/2004 | Reber et al. |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0062722 A1 | 4/2004 | Gonda et al. |
| 2004/0076588 A1 | 4/2004 | Batycky et al. |
| 2004/0077528 A1 | 4/2004 | Steiner et al. |
| 2004/0096403 A1 | 5/2004 | Steiner |
| 2004/0107963 A1 | 6/2004 | Finlay et al. |
| 2004/0121964 A1 | 6/2004 | Madar et al. |
| 2004/0138099 A1 | 7/2004 | Draeger |
| 2004/0151059 A1 | 8/2004 | Robert, II et al. |
| 2004/0151774 A1 | 8/2004 | Pauletti et al. |
| 2004/0157928 A1 | 8/2004 | Kim et al. |
| 2004/0163648 A1 | 8/2004 | Burton |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0211420 A1 | 10/2004 | Minshull et al. |
| 2004/0234615 A1 | 11/2004 | Sabetsky |
| 2004/0234616 A1 | 11/2004 | Sabetsky |
| 2004/0235956 A1 | 11/2004 | Quay |
| 2004/0241232 A1 | 12/2004 | Brown et al. |
| 2004/0247628 A1 | 12/2004 | Lintz et al. |
| 2004/0250812 A1 | 12/2004 | Davies et al. |
| 2005/0000518 A1 | 1/2005 | Dunkley et al. |
| 2005/0003003 A1 | 1/2005 | Basu et al. |
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |
| 2005/0080000 A1 | 4/2005 | Thurow et al. |
| 2005/0119604 A1 | 6/2005 | Bonney et al. |

(56) References Cited

U.S. PATENT DOCUMENTS

| | | |
|---|---|---|
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0203002 A1 | 9/2005 | Tzannis et al. |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0062740 A1 | 3/2006 | Rand |
| 2006/0099269 A1 | 5/2006 | Cheatham et al. |
| 2006/0102511 A1 | 5/2006 | Pasbrig et al. |
| 2006/0120969 A1 | 6/2006 | Nilsson et al. |
| 2006/0130838 A1 | 6/2006 | Lee et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0219242 A1 | 10/2006 | Zierenberg |
| 2006/0239933 A1 | 10/2006 | Nilsson et al. |
| 2006/0239934 A1 | 10/2006 | Cheatham et al. |
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0160789 A1 | 7/2007 | Merical et al. |
| 2007/0175314 A1 | 8/2007 | Wanne |
| 2007/0190163 A1 | 8/2007 | Malakhov et al. |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0243216 A1 | 10/2007 | Kepka et al. |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0039368 A1 | 2/2008 | Steiner et al. |
| 2008/0039402 A1 | 2/2008 | Mossalayi et al. |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127974 A1 | 6/2008 | Lastow |
| 2008/0129791 A1 | 6/2008 | King et al. |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0312155 A1 | 12/2008 | Kitada et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0099077 A1 | 4/2009 | Sur et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0294521 A1 | 12/2009 | De La Huerga |
| 2009/0314291 A1 | 12/2009 | Anderson et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0051027 A1 | 3/2010 | Remmelgas et al. |
| 2010/0065048 A1 | 3/2010 | Walz et al. |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0215588 A1 | 8/2010 | Skaliter |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0023876 A1 | 2/2011 | Vehring et al. |
| 2011/0061653 A1 | 3/2011 | Schuckmann |
| 2011/0083667 A1 | 4/2011 | Briant |
| 2011/0155129 A1 | 6/2011 | Stedman et al. |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adam et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0221097 A1 | 8/2013 | Day et al. |

(56) References Cited

U.S. PATENT DOCUMENTS

| | | |
|---|---|---|
| 2013/0243828 A1 | 9/2013 | Lipp et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |
| 2015/0045295 A1 | 2/2015 | Smutney et al. |
| 2015/0052977 A1 | 2/2015 | Adamo et al. |
| 2015/0065422 A1 | 3/2015 | Kraft |
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283069 A1 | 10/2015 | Smutney et al. |
| 2015/0283213 A1 | 10/2015 | Costello et al. |
| 2015/0290132 A1 | 10/2015 | Gelber et al. |
| 2015/0359744 A1 | 12/2015 | Hokenson et al. |
| 2016/0008557 A1 | 1/2016 | Smutney et al. |
| 2016/0031833 A1 | 2/2016 | Wilson et al. |
| 2016/0067183 A1 | 3/2016 | Kraft |
| 2016/0095990 A1 | 4/2016 | Smutney et al. |
| 2016/0101049 A1 | 4/2016 | Wilson et al. |
| 2016/0151287 A1 | 6/2016 | Oberg et al. |
| 2016/0158156 A1 | 6/2016 | Fabio et al. |
| 2016/0175079 A1 | 6/2016 | Adamo et al. |
| 2016/0193432 A1 | 7/2016 | Harris et al. |
| 2016/0221967 A1 | 8/2016 | Stevenson et al. |
| 2016/0228659 A1 | 8/2016 | Smutney et al. |
| 2016/0243322 A1 | 8/2016 | Smutney et al. |
| 2016/0250297 A1 | 9/2016 | Leone-Bay et al. |
| 2016/0256640 A1 | 9/2016 | Overfield et al. |
| 2016/0287820 A1 | 10/2016 | Smutney et al. |
| 2016/0346212 A1 | 12/2016 | Hokenson et al. |
| 2016/0346394 A1 | 12/2016 | Grant et al. |
| 2017/0087217 A1 | 3/2017 | Cheatham et al. |
| 2017/0143804 A1 | 5/2017 | Boss et al. |
| 2017/0189395 A1 | 7/2017 | Grant et al. |
| 2017/0189492 A1 | 7/2017 | Boss et al. |
| 2017/0209525 A1 | 7/2017 | Leone-Bay et al. |
| 2017/0216280 A1 | 8/2017 | Kraft |
| 2017/0216538 A1 | 8/2017 | Kinsey et al. |
| 2017/0232001 A1 | 8/2017 | Guarneri et al. |
| 2017/0274050 A1 | 9/2017 | Leone-Bay et al. |
| 2017/0281549 A1 | 10/2017 | Oberg et al. |
| 2017/0304404 A1 | 10/2017 | Costello et al. |
| 2017/0369452 A1 | 12/2017 | Stevenson et al. |

FOREIGN PATENT DOCUMENTS

| | | |
|---|---|---|
| CN | 2917673 Y | 7/2007 |
| CN | 101290219 A | 10/2008 |
| CN | 101317821 | 12/2008 |
| CN | 101851213 | 10/2010 |
| CN | 102436238 A | 5/2012 |
| CN | 103110611 A | 5/2013 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 0837710 B1 | 11/2001 |
| EP | 640354 B1 | 12/2001 |
| EP | 1348428 A1 | 10/2003 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | S55-156085 U | 11/1980 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 1990/013285 | 11/1990 |
| WO | 1991/004011 | 4/1991 |
| WO | 1991/006287 | 5/1991 |
| WO | 1991/016038 | 10/1991 |
| WO | 1991/016882 | 11/1991 |
| WO | 1991/019524 | 12/1991 |
| WO | 1992/004069 | 3/1992 |
| WO | 1992/008509 | 5/1992 |
| WO | 1993/002712 | 2/1993 |
| WO | 1993/014110 | 7/1993 |
| WO | 1993/017728 | 9/1993 |
| WO | 1993/018754 A1 | 9/1993 |
| WO | 1994/000291 | 1/1994 |
| WO | 1994/008552 | 4/1994 |
| WO | 1994/008599 | 4/1994 |
| WO | 1994/019041 | 9/1994 |
| WO | 1994/023702 | 10/1994 |
| WO | 1994/025005 A1 | 11/1994 |
| WO | 1995/000127 A1 | 1/1995 |
| WO | 1995/005208 | 2/1995 |
| WO | 1995/011666 | 5/1995 |
| WO | 1995/024183 A1 | 9/1995 |
| WO | 1995/031979 | 11/1995 |

(56) References Cited

FOREIGN PATENT DOCUMENTS

| | | |
|---|---|---|
| WO | 1995/034294 | 12/1995 |
| WO | 1996/001105 | 1/1996 |
| WO | 1996/005810 | 2/1996 |
| WO | 1996/013250 | 5/1996 |
| WO | 1996/022802 A | 8/1996 |
| WO | 1996/027386 A1 | 9/1996 |
| WO | 1996/032149 | 10/1996 |
| WO | 1996/036314 | 11/1996 |
| WO | 1996/036317 A1 | 11/1996 |
| WO | 1996/040206 A1 | 12/1996 |
| WO | 1997/001365 | 1/1997 |
| WO | 1997/004747 | 2/1997 |
| WO | 1997/025086 A2 | 7/1997 |
| WO | 1997/030743 | 8/1997 |
| WO | 1997/035562 A1 | 10/1997 |
| WO | 1997/046206 | 12/1997 |
| WO | 1997/049386 | 12/1997 |
| WO | 1998/026827 A1 | 6/1998 |
| WO | 1998/034661 A1 | 8/1998 |
| WO | 1998/039043 | 9/1998 |
| WO | 1998/041255 A2 | 9/1998 |
| WO | 1998/043615 | 10/1998 |
| WO | 1999/014239 A1 | 3/1999 |
| WO | 1999/018939 A1 | 4/1999 |
| WO | 1999/032510 A1 | 7/1999 |
| WO | 1999/033862 | 7/1999 |
| WO | 1999/052506 | 10/1999 |
| WO | 2000/12116 | 3/2000 |
| WO | 2000/033811 A2 | 6/2000 |
| WO | 2000/059476 A1 | 10/2000 |
| WO | 2000/071154 A2 | 11/2000 |
| WO | 2001/000654 | 1/2001 |
| WO | 2001/081321 A | 1/2001 |
| WO | 2001/032144 A1 | 5/2001 |
| WO | 2001/049274 A2 | 7/2001 |
| WO | 2001/051071 | 7/2001 |
| WO | 2001/052813 A1 | 7/2001 |
| WO | 2001/066064 | 9/2001 |
| WO | 2001/068169 | 9/2001 |
| WO | 2001/097886 A1 | 12/2001 |
| WO | 2001/007107 | 2/2002 |
| WO | 2002/011676 | 2/2002 |
| WO | 2002/012201 A1 | 2/2002 |
| WO | 2002/047659 A2 | 6/2002 |
| WO | 2002/058735 | 8/2002 |
| WO | 2002/059574 A1 | 8/2002 |
| WO | 2002/067995 A1 | 9/2002 |
| WO | 2002/085281 | 10/2002 |
| WO | 2002/098348 | 12/2002 |
| WO | 2002/102444 | 12/2002 |
| WO | 2003/000202 | 1/2003 |
| WO | 2003/015857 A1 | 2/2003 |
| WO | 2003/018059 A2 | 3/2003 |
| WO | 2003/022304 A1 | 3/2003 |
| WO | 2003/055547 A1 | 7/2003 |
| WO | 2003/057170 | 7/2003 |
| WO | 2003/061578 A2 | 7/2003 |
| WO | 2003/072195 A2 | 9/2003 |
| WO | 2003/080149 A2 | 10/2003 |
| WO | 2003/084502 A1 | 10/2003 |
| WO | 2003/086345 | 10/2003 |
| WO | 2003/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054605 A1 | 7/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/002654 A2 | 1/2005 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/082328 A1 | 7/2011 |
| WO | 2011/163272 | 12/2011 |
| WO | 2012/064892 A1 | 5/2012 |
| WO | 2012/135765 | 10/2012 |

(56) References Cited

FOREIGN PATENT DOCUMENTS

| | | |
|---|---|---|
| WO | 2012/174472 A1 | 12/2012 |
| WO | 2012/174556 A1 | 12/2012 |
| WO | 2013/016754 A1 | 2/2013 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/0144895 A1 | 9/2014 |
| WO | 2015/010092 A1 | 1/2015 |
| WO | 2015/021064 A1 | 2/2015 |
| WO | 2015/063100 A1 | 5/2015 |
| WO | 2015/148905 A1 | 10/2015 |
| WO | 2017/132601 | 8/2017 |
| WO | 2017/201463 | 11/2017 |

OTHER PUBLICATIONS

Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=2885&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107,2006.

Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11):4542-4546 (2007).
Yoshida et al., Absorption of insulin delivered to rabbit trachea using aerosol dosage form. J. Pharm. Sci. 68(5):670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action dated Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action dated Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left col. of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation losage forms of insulin with spray fluidized bed granulating system. J. Soc. Powder Technol., Japan, 41: 514-521 (2004).
"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
Adjusting Mealtime Insulin Doses. BD Diabetes. http://www.bd.com/diabetes/page.aspx?cat=7001&id=7280 (2014).

(56) References Cited

OTHER PUBLICATIONS

Ahren "GLP-1 and extra-islet effects." Horm. Med Res 36:842, 2004.
Ahren B et al. "Characterization of GLP-1 effects on b-cell function after meal ingestion in humans." Diabetes Care 26:2860,2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.
Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at meal-times" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.
AVANDIA Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al. "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Bilheimer DW, Ren H, Boss AH. Analysis of cardiovascular adverse events in patients with type 1 or type 2 diabetes enrolled in selected

(56) References Cited

OTHER PUBLICATIONS therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/ Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.
Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G., et al. "Physiological importance of deficiency of early prandial insulin secretion in non-insulin-dependent diabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. AFRESA® (Technosphere® insulin) dosage strengths are interchangeable ADA 2009; Poster 433.
Cassidy JP, Marino MT, Amin N, et al. Lung deposition and absorption of insulin from AFRESA® (Technosphere® insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life Considerations on shape and function." Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3): 203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.

(56) References Cited

OTHER PUBLICATIONS

Chan et al., "Pharmacological Management of Type 2 Diabetes Mellitus: Rationale for Rational Use of Insulin", Mayo Clin Proc, 2003, 78, 459-467.

Chase et al., "Redefining the clinical remission period in children with type 1 diabetes", Pediatric Diabetes, 2004, 5, 16-19.

Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).

Cheatham et al. "A novel pulmonary insulin formulation replicates first phase insulin release and reduces s-proinsulin levels." Presented at the American Diabetes Association 64th Scientific Sessions, Jun. 2004, abstract 457-P.

Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.

Rosenstock et al. "Inhaled Insulin Improves Glycemic Control when Substituted for or Added to Oral Combination Therapy in Type 2 Diabetes." Ann Intern Med 143:549-558, 2005.

Rosenstock et al., "Reduced hypoglycemia risk with insulin glargine: a meta-analysis comparing insulin glargine with human NPH insulin in type 2 diabetes", Diabetes Care, 28(4):950-5 (2005).

Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.

Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.

Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.

Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).

Rossiter A, Howard C, Amin N, et al. Technosphere® insulin: Safety in type 2 diabetes mellitus. ADA 2010; Poster 523.

Roumeliotis, New inhaler launched with a bag, in-Pharma Technologist.com, Decision News Media SAS (2006).

Rousseau et al. "Drug delivery by fumaryl diketopiperazine particles: evidence for passive transport." Presented at the American Diabetes Association 64th Scientific Sessions, Jun. 2004, abstract 484-P.

Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.

Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.

Ryan EA et al. "Successful islet transplantation. Continued insulin reserve provides long-term glycemic control." Diabetes 51:2148-2157, 2002.

Sajeesh et al., Cyclodextrin-insulin complex encapsulated polymethacrylic acid based nanoparticles for oral insulin delivery. International Journal of Pharmaceuticals, 2006, 325, pp. 147-154.

Sakagami M et al. "Respirable microspheres for inhalation: the potential of manipulating pulmonary disposition for improved therapeutic efficacy." Clin Pharmacokinet 44(3):263-277, 2005.

Sakr, A new approach for insulin delivery via the pulmonary route: design and pharmacokinetics in non-diabetic rabbits. International Journal of Pharmaceutics, 86: 1-7 (1992).

Salib, Utilization of sodium alginate in drug microencapsulation. Pharazeutische Industrie, 40(11a): 1230-1234 (1978).

Saraceni C et al. "Effects of glucagon-like peptide-1 and long-acting analogues on cardiovascular and metabolic function" Drugs R D 8:145, 2007.

Sarrach et al., "Binding and entrapment of insulin by liposomes made of lecithin-phosphotidix acid in acid solution" Pharmazie 40:642-645, 1985 (German and English Abstract).

Savage et al., "Effects of peptide YY (PYY) on mouth to caecum intestinal transit time and on the rate of gastric emptying healthy volunteers", Gut, vol. 28, pp. 166-170, 1987.

Sawhney et al., Bioerodible hydrogels based on photopolymerized poly(ethylene glycol)-co-poly(a-hydroxy acid) diacrylate macromers. Macromolecules, 26: 581-587 (1993).

Schaffer et al. "Assembly of high-affinity insulin receptor agonists and antagonists from peptide building blocks." PNAS 100:4435-4439, 2003.

Schepp et al., Eur. J. Pharmacol., 269:183-91, 1994.

Scherbaum "Unlocking the opportunity of tight glycaemic control. Inhaled insulin: clinical efficacy." Diabetes Obesity and Metabolism 7:S9-S13, 2005.

Schirra et al. "Gastric emptying and release of incretin hormones after glucose ingestion in humans." J Clin Invest 97:92-103,1996.

Schluter et al., "Pulmonary Administration of Human Insulin in volunteers and Type I Diabetics", Diabetes, 33, (Suppl) 298 (1984).

Schneider et al., "Stimulation by proinsulin of expression of plasminogen activator inhibitor type 1 in endothelial cells", Diabetes 41(7):890-895 (1992).

Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.

Schroder, " Crystallized carbohydrate spheres as a slow release matrix for biologically active substances", Biomaterials 5:100-104, 1984.

Scrocchi et al. "Glucose intolerance but normal satiety in mice with a null mutation in the glucagon-like peptide 1 receptor gene." Nature Medicine 2:1254-1258, 1996.

Seshiah & Balaji, "Early Insulin Therapy in Type 2 Diabetics", Int. J. Diabetes in Developing Countries, 2003, 23, 90-93.

Seville, P.C. et al., Preparation of dry powder dispersions for non-viral gene delivery by freeze-drying and spray drying. J. Gene Medicine 2002; 4:428-437.

Shah et al. "Lack of suprression of glucagon contributes to postprandial hyperglycemia in subjects with type 2 diabetes mellitus." J Clin Indocrinol Metab 85:4053, 2000.

Shelly et al. "Polysorbate 80 hypersensitivity." The Lancet 345:1312, 1995.

Shimada et al. Translocation pathway of the intertracheally instilled ultrafine particles from the lung into the blood circulation in the mouse. Toxicologic Pathology pp. 949-957 (2006).

Shojania et al. "Effect of quality improvement strategies for type 2 diabetes on glycemic control." JAMA 296:427, 2006.

Silverstein et al., "Care of Children and Adolescens with Type 1 Diabetes, A Statement of the American Diabetes Association", Diabetes Care, Jan. 2005, vol. 28, p. 186-212.

Singh et al., Use of 125I-[Y39]exendin-4 to characterize exendin receptors on dispersed pancreatic acini and gastric chief cells from guinea pig. Regul. Pept. 53 : 47-59 (1994).

Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.

Skyler, Pulmonary insulin: current status. Diabetes Voice, vol. 51, Issue I, p. 23-25, 2006.

Skyler "Pulmonary Insulin Delivery—State of the Art 2007." Diabetes Tecnology & Therapeutics, vol. 9, Supplement 1, pp. S1-S3. 2007.

Skyler JS et al. "Use of inhaled insulin in a basal/bolus insulin regimen in Type 1 diabetic subjects." Diabetes Care 28:1630-1635, 2005.

Smith et al. "New-onset diabetes and risk of all-cause and cardiovascular mortality." Diabetes Care 29:2012, 2006.

(56) References Cited

OTHER PUBLICATIONS

Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 and in Non-Final Offfice Action dated May 22, 2014 for U.S. Appl. No. 13/797,657 and cited by Examiner in Non-Final Office Action dated May 22, 2014 for U.S. Appl. No. 12/883,369.
Shields, Irritable bowel syndrome, archived Jun. 21, 2009, available at: https://web.archive.org/web/200906211 00502/ http://www.gastroenterologistpaloalto.com/conditions-diseases-irritable-bowelsyndrome-palo-alto-ca. html; on Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 15/152,355, filed May 11, 2016.
Design U.S. Appl. No. 29/504,212, filed Oct. 2, 2014.
Chan et al., Physical stability of salmon calcitonin spray-dried powders for inhalation. Journal of Pharmaceutical Sciences, vol. 93, No. 3, pp. 792-804 (2004).
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
Sarala et al., Technosphere: New drug delivery system for inhaled insulin. Future Prescriber, vol. 13, No. 1, pp. 14-16 (2012).
Uwaifo et al., Novel pharmacologic agents for type 2 diabetes. Endocrinology and Metabolism Clinics of North America, vol. 34, No. 1, pp. 155-197 (2005).
Xi-de Tu, et al. Pharmaceutics. Oct. 2002, 3rd edition, second printing, p. 905.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (LISPRO) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, Streptomyces sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insu-

(56) References Cited

OTHER PUBLICATIONS lin into their usual diabetes treatment regimen vs continuing their usual diabetes management. AACE 2010; Poster 283.

Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.

Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).

Raufman et al., Truncated glucagon-like peptide-1 interacts with exendin receptors on dispersed acini from guina pig pancreas. J. Biol. Chem. 267(30) : 21432-21437 (1992).

Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.

Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.

Rave et al. "Dose Response of Inhaled Dry-Powder Insulin and Dose Equivalence to Subcutaneous Insulin Lispro." Diabetes Care 28:2400-2405, 2005.

Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.

Rave et al. "Results of a Dose-Response Study with a New Pulmonary Insulin Formulation and Inhaler." Diabetes 49, Supplement, May 2000, A75.

Rave et al. "Time-action profile of inhaled insulin in comparison with subcutaneously injected insulin lispro and regular human insulin." Diabetes Care 28:1077, 2005.

Rave K, Heise T, Pfuetzner A, et al. Assessment of dose-response characteristics for a new pulmonary insulin formulation and inhaler. Exp Clin Endocrinol Diabetes 2000; 108:S161.

Rave K, Potocka E, Boss AH, et al. Pharmacokinetics and linear exposure of AFRESA™ compared with the subcutaneous injection of regular human insulin Diabetes, Obesity and Metabolism 2009; 11:715-720.

Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.

Razavi et al. "TRPVI+ sensory neurons control beta cell stress and islet inflammation in autoimmune disease." Cell 127:1123, 2006.

Retrieved from website: http://groups.molbiosci.northwestern.edu/holmgren/Glossary/Definitions/Def-P/placebo.html, 1 page, Retrieved on Mar. 12, 2013.

Rhodes et al. "Technosphere: Microspherical Particles from Substituted Diketopiperazines for Use in Oral Drug Delivery." 208th ACS National Meeting, Aug. 1994.

Richardson et al. "Technosphere Insulin Technology." Diabetes Technology & Therapeutics, vol. 9, Supplement 1, pp. S65-S72, 2007.

Richardson PC, Potocka E, Baughman RA, et al. Pharmacokinetics of Technosphere® insulin unchanged in patients with chronic obstructive pulmonary disease. Diabetologia 2009; 52 (suppl 1).

Richter et al. "Characterization of glucagon-like peptide-1(7-36)amide receptors of rat membranes by covalent cross-linking." FEBS Letters 280:247, 1991.

Richter et al. "Characterization of receptors for glucagon-like peptide-1 (7-36)amide on rat lung membranes." FEBS Letters 267:78, 1990.

Riddle "Combining Sulfonylureas and Other Oral Agents." Am J Med, 2000, vol. 108(6A), pp. 15S-22S.

Riddle et al. "Emerging therapies mimicking the effects of amylin and glucagon-like peptide 1." Diabetes Care 29:435, 2006.

Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.

Rosen et al., Substance P microinjected into the periaqueductal gray matter induces antinociception and is released folloing morphine administration. Brain Research, 1001: 87-94 (2004).

Rosenmund et al., Diketopiperazines from Leuchs Anhydrides. Angew Chem Intern. Edit. vol. , No. 2 (1970).

Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018—PO, 2008.

Johnson et al., "Turbuhaler a new device for dry powder terbutaline inhalation", Allergy 43(5):392-395 (1988).

Johnson et al: RyR2 and calpain-10 delineate a novel apoptosis pathway in pancreatic islets. J Biol Chem., 279(23):24794-802, 2004.

Johnson, Keith A., Preparation of peptide and protein powders for inhalation. Advanced Drug Delivery Reviews 1997; 26:3-15.

Jones et al., An investigation of the pulmonary absorption of insulin in the rat. Third European Congress of Biopharmaceutics and Pharmacokinetics, (1987).

Joseph et al. "Oral delivery of glucagon-like peptide-1 in a modified polymer preparation normalizes basal glycaemia in diabetic db/db mice." Diabetologia 43:1319-1328, 2000.

Joy et al. "Incretin mimetics as emerging treatments for type 2 diabetes." Annal Pharmacother 39:110, 2005.

Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.

Kanse et al. "Identification and characterization of glucagon-like peptide-1 7-36 amide-binding sites in the rat brain and lung." FEBS Letters 241:209, 1988.

Kapitza C et al. "Impact of particle size and aerosolization time on the metabolic effect of an inhaled insulin aerosol." Diabetes Tech Ther 6:119, 2004.

Kapitza et al. "Dose-response characteristics for a new pulmonary insulin formulation and inhaler." Presented at the 35th Annual Meeting of the EASD, Sep. 2000, abstract OP29 184.

Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).

Katchalski E et al. "Synthesis of lysine anhydride", J. Amer Chem Soc 68:879-880, 1946.

Katz et al. "Quantitative insulin sensitivity check index: a simple, accurate method for assessing insulin sensitivity in humans." J. Clin. Endocrinol. Metab. 85:5402-2410, 2000.

Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.

Kawai et al. "Evidence that glucagon stimulates insulin secretion through its own receptor in rats." Diabetologia 38:274, 1995.

Kawamori et al. "Does hyperinsulinemia accelerate atherosclerosis?" Department of Medicine, Juntendo University School, vol. 13, No. 12, p. 954-960, 1994.

Kelley, D. et al. "Impaired postprandial glucose utilization in non-insulin dependent diabetes mellitus." Metabolism 43:1549-1557, 1994.

Kenny AJ et al. "Dipeptidyl peptidase IV, a kidney brush-border serin peptidase." Biochem J. 155:169, 1976.

Kim et al. "Development and characterization of a glucagon-like peptide 1-albumin conjugate. The ability to activate the glucagon-like peptide 1 receptor in vivo." Diabetes 52:751, 2003.

(56) References Cited

OTHER PUBLICATIONS

Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmacology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).

(56) References Cited

OTHER PUBLICATIONS

Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al. "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.

Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere™/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
EXUBERA package insert, p. 1, 2008.
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22(10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
GLUCOPHAGE Product Insert. Jan. 2009.
GLUCOTROL Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide

(56) References Cited

OTHER PUBLICATIONS 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk actors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.

Hassan et al. "A Randomized, Controlled Trial Comparing Twice-a-Day Insulin Glargine Mixed with Rapid-Acting Insulin Analogs Versus Standard Neutral Protamine Hagedorn (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep.;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.

(56) References Cited

OTHER PUBLICATIONS

DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, NIKKEI BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™/insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140 : 123-132 (2003).
Svartengren et al., Added External Resistance Reduces Oropharyngeal Deposition and Increases Lung Deposition of Aerosol Particles in Asthmatics. Am. J. Respir. Crit. Care Med., vol. 152, pp. 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).

(56) References Cited

OTHER PUBLICATIONS

Gerber et al., Treatment satisfaction with inhaled insulin in patients with type 1 diabetes. Diabetes Care 24:1556-1559 (2001).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves post-prandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commercial launch of Exubera. Pharmaceutical & Medical Packaging News, vol. 14, No. 6 (2006).
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Lorber D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Lorber D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R,Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1

(56) References Cited

OTHER PUBLICATIONS diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESA® (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed by Examiner on Apr. 30, 2014 and Cited by Examiner in Non-Final Office Action dated May 22, 2014 for U.S. Appl. No. 13/797,657 and Cited by Examiner in Non-Final Office Action dated May 22, 2014 for U.S. Appl. No. 12/883,369.
International Search Report for PCT International Application No. PCT/US2010/055323 filed on Nov. 3, 2010.
Written Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.
International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavored Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Amodeo et al., Pain peptides. Solution structure of orphanin FQ2. FEBS Letters, vol. 473, Issue 2, pp. 157-160 (2000).
Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).
Krondahl et al., Regional differences in bioavailability of an opioid tetrapeptide in vivo rats after administration to the respiratory tract. Peptides, vol. 23, No. 3, pp. 479-488 (2002).
Lee et al., Intrapulmonary potential of polyethylene glycol-modified glucagon-like peptide-1s as a type 2 anti-diabetic agent. Regulatory Peptides, 152:101-107 (2009).
Selam, Jean-Louis. Inhaled Insulin: Promises and Concerns. Journal of Diabetes Science and Technology, vol. 2, Issue 2, pp. 311-315 (2008).
Fabio et al., Heat-stable dry powder oxytocin formulations or delivery by oral inhalation. AAPS PharmSciTech, (2015).
Lane et al., Influence of post-emulsification drying processes on the microencapsulation of Human Serum Albumin. International Journal of Pharmaceutics, 307: 16-22 (2006).
Mumenthaler et al., Feasibility study on spray-drying protein pharmaceuticals: recombinant human growth hormone and tissue-type plasminogen activator. Pharm Res., 11(1):12-20 (1994).
U.S. Appl. No. 15/182,503, filed Jun. 14, 2016.
Design U.S. Appl. No. 29/553,303, filed Jan. 29, 2016.
Design U.S. Appl. No. 29/553,302, filed Jan. 29, 2016.
Design U.S. Appl. No. 29/553,305, filed Jan. 29, 2016.
Design U.S. Appl. No. 29/553,300, filed Jan. 29, 2016.
U.S. Appl. No. 15/233,794, filed Aug. 10, 2016.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.

(56) References Cited

OTHER PUBLICATIONS

Mann "Pulmonary insulin—the future of prandial insulin therapy." Presented at the 5th Annual Meeting of the Diabetes Technology Society, Nov. 2005, abstract A94.
MannKind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analong of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.

Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the fine particle fraction produced by dry powder inhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al. Diabetes, 45(Suppl. 2):152A, 1996.
Moren, Aerosols in Medicine (2nd Ed.), Elsevier, pp. 321-350 (1993).
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report dated Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
European Search report for European Application 16203266.8 dated Jul. 5, 2017.
European Search Report for European Application 13161157.6 dated Dec. 8, 2017.
Hache et al., Inhaled prostacyclin (PGI2) is an efffective addition to the treatment of pulmonary hypertension and hypoxia in the operating room and intensive care unit. Can. J. Anesth., 48:9, pp. 924-929 (2001).
International Search Report and Written Opinion dated Apr. 28, 2017 for International Application No. PCT/US2017/015486 filed on Jan. 27, 2017.
International Search Report and Written Opinion dated Sep. 21, 2017 for International Application No. PCT/US2017/033627 filed on May 19, 2017.
Journal of Technical Disclosure of Japan Institute of Invention and Innovation; Food Drying Process Techniques; Japan Institute of Invention and Innovation; Independent Administrative Agency; National Center for Industrial Property Information and Training; published Mar. 31, 2005; p. 3-6, 8, 11, and 13 (reference showing well-known technique).
Leone-Bay A., Pulmonary Delivery: Pulmonary peptide delivery with a pharmacokinetic profile that closely mimics endogenous peptide secretion. Drug Development & Delivery, vol. 11, No. 4, pp. 34-39 (2011).
Leone-Bay A., Pulmonary Drug Delivery—Simplified. www.ondrugdelivery.com, pp. 18-21 (2011).
Smutney et al., Special Report, Special Focus: Pulmonary Drug Delivery, Device factors affecting pulmonary delivery of dry powders. Ther. Deliv., 4(8):939-949 (2013).
U.S. Appl. No. 15/706,504, filed Sep. 15, 2017.

(56) References Cited

OTHER PUBLICATIONS

U.S. Appl. No. 15/711,916, filed Sep. 21, 2017.
Design U.S. Appl. No. 29/604,731, filed May 19, 2017.
Design U.S. Appl. No. 29/625,323, filed Nov. 8, 2017.
Hawe et al., Towards heat-stable oxytocin formulations: Analysis of degradation kinetics and identification of degradation products. Pharmaceutical Research, vol. 26, No. 7, pp. 1679-1688 (2009).
Kim et al., Dose-response relationships of inhaled insulin delivered via the aerodose insulin inhaler and subcutaneously injected insulin in patients with type 2 diabetes. Diabetes Care, 26:2842-2847 (2003).
Klonoff, David C. M.D., Afrezza inahled insulin: the fastest-acting FDA-approved insulin on the market has favorable properties. Journal of Diabetes Science and Technology, vol. 8(6): 10-71-1073 (2014).
Marconi et al., Chemical composition and nutritional properties of commercial products of mare milk powder. Journal of Food Composition and Analysis 11:178-187 (1998).

FIG. 16

| Demographic and Baseline Characteristics by Randomized Treatment Group (ITT Population) | | | | |
|---|---|---|---|---|
| Characteristic | Statistic | TI Alone (n = 177) | Metformin + Secretagogue (n = 162) | TI + Metformin (n = 169) |
| Gender, Number of Subjects (%) | | | | |
| ➤ Male | | 84 (47.5) | 74 (45.7) | 68 (40.2) |
| ➤ Female | | 93 (52.5) | 88 (54.3) | 101 (59.8) |
| Race, Number of Subjects (%) | | | | |
| ➤ Caucasian | | 133 (75.1) | 114 (70.4) | 129 (76.3) |
| ➤ Black | | 9 (5.1) | 8 (4.9) | 12 (7.1) |
| ➤ Asian | | 4 (2.3) | 5 (3.1) | 2 (1.2) |
| ➤ Hispanic | | 26 (14.7) | 25 (15.4) | 23 (13.6) |
| ➤ Other | | 5 (2.8) | 10 (6.2) | 3 (1.8) |
| Age, Years | | | | |
| | Mean (SD) | 57.3 (8.47) | 57.6 (9.14) | 56.8 (8.31) |
| Weight, Kilograms | | | | |
| | Mean (SD) | 86.14 (15.59) | 84.18 (16.21) | 83.87 (13.93) |
| BMI, kg/m2 | | | | |
| | Mean (SD) | 31.23 (4.30) | 30.73 (4.61) | 30.81 (4.40) |
| Baseline HbA1c (%) | | | | |
| | Mean (SD) | 8.92 (0.95) | 8.90 (0.94) | 8.95 (0.97) |
| Fasting Plasma Glucose (mg/dL) | | | | |
| | Mean (SD) | 193.59 (53.58) | 197.31 (47.96) | 189.39 (47.34) |
| • Percentages are based on the number of subjects in each treatment group in the specified population (n). Statistics are summarized by the randomized treatment group. SD=Standard Deviation | | | | |

USE OF ULTRARAPID ACTING INSULIN

CROSS-REFERENCE TO RELATED APPLICATIONS

This application is a 371 of PCT/US2015/022956, filed Mar. 27, 2015, which claims benefit under 35 U.S.C. § 119(e) from U.S. Provisional Patent Application Ser. No. 61/972,159, filed Mar. 28, 2014, the contents each of which is incorporated herein by reference in its entirety.

FIELD

The present invention relates to methods for treating diabetes mellitus with an ultrarapid acting prandial insulin. Particular embodiments of the invention relate to various modes of administration which take advantage of the unique kinetic profile of such formulations, as well as substitution of such an insulin for one or more oral antidiabetic agents in the standard treatment regimen of diabetes mellitus, type 2.

BACKGROUND

Diabetes mellitus (hereinafter, diabetes) currently afflicts at least 200 million people worldwide. The two main sub-types of diabetes include types 1 and 2. Type 1 diabetes accounts for about 10% of the 200 million afflicted with diabetes. Type 1 diabetes is caused by autoimmune destruction of insulin-secreting β-cells in the pancreatic islets of Langerhans. Type 2 diabetes accounts for the remaining 90% of individuals afflicted, and the prevalence is increasing. Type 2 diabetes is often, but not always, associated with obesity, and although previously termed late-onset or adult-onset diabetes, is now becoming increasingly more prevalent in younger individuals. Type 2 diabetes is caused by a combination of insulin resistance and inadequate insulin secretion.

The Physiological Role of Insulin

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

Five different phases of insulin secretion have been identified: (1) basal insulin secretion wherein insulin is released in the postabsorptive state; (2) the cephalic phase wherein insulin secretion is triggered by the sight, smell and taste of food, before any nutrient is absorbed by the gut, mediated by pancreatic innervation; (3) early-phase insulin secretion wherein an initial burst of insulin is released within the first 5-10 minutes after the β-cell is exposed to a rapid increase in glucose, or other secretagogues; (4) second-phase insulin secretion wherein the insulin levels rise more gradually and are related to the degree and duration of the stimulus; and (5) a third-phase of insulin secretion that has only been described in vitro. During these stages, insulin is secreted, like many other hormones, in a pulsatile fashion, resulting in oscillatory concentrations in the blood. Oscillations include rapid pulses (occurring every 8-15 minutes) superimposed on slower oscillations (occurring every 80-120 minutes) that are related to fluctuations in blood glucose concentration.

Insulin secretion can be induced by other energetic substrates besides glucose (particularly amino acids) as well as by hormones and drugs. Of note is that the insulin response observed after food ingestion cannot be accounted for solely by the increase in blood glucose levels, but also depends on other factors such as the presence of free fatty acids and other secretagogues in the meal, the neurally activated cephalic phase and gastrointestinal hormones.

When an individual is given an intravenous glucose challenge, a biphasic insulin response is seen which includes a rapid increase with a peak, an interpeak nadir and a subsequent slower increasing phase. This biphasic response is only seen when glucose concentration increases rapidly, such as after a glucose bolus or glucose infusion. A slower increase in glucose administration, what is seen under physiologic conditions, induces a more gradually increasing insulin secretion without the well-defined biphasic response seen in response to bolus infusion of glucose.

Modeling of early-phase insulin responses under normal physiologic conditions has demonstrated that, after a meal, glucose concentration increases more gradually ($C_{max}$ reached in approximately 20 minutes) than seen with intravenous bolus injections of glucose ($C_{max}$ reached in approximately 3-10 minutes).

Healthy pancreatic β-cells generate an early response to a meal-like glucose exposure that rapidly elevates serum insulin both in the portal circulation and in the periphery. Conversely, defective β-cells, which have an impaired early-phase insulin response, generate a sluggish response to the meal-like glucose exposure.

Increasingly, evidence indicates that an early relatively rapid insulin response following glucose ingestion plays a critical role in the maintenance of postprandial glucose homeostasis. An early surge in insulin concentration can limit initial glucose excursions, mainly through the inhibition of endogenous glucose production. Therefore the induction of a rapid insulin response in a diabetic individual is expected to produce improved blood glucose homeostasis.

In a normal individual, a meal induces the secretion of a burst of insulin, generating a relatively rapid spike in serum insulin concentration that then decays relatively quickly (see FIG. 1). This early-phase insulin response is responsible for the shut-off, or reduction, of glucose release from the liver. Homeostatic mechanisms then match insulin secretion (and serum insulin levels) to the glucose load. This is observed as a slow decay of modestly elevated serum insulin levels back to baseline and is second-phase kinetics.

Diabetes

A central characteristic of diabetes is impaired β-cell function. One abnormality that occurs early in the disease progression in both type 1 and 2 diabetes is the loss of eating-induced rapid insulin response. Consequently, the liver continues to produce glucose, which adds to the glucose that is ingested and absorbed from the basic components of a meal.

Type 2 diabetics typically exhibit a delayed response to increases in blood glucose levels. While normal individuals usually begin to release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels). Another characteristic of type 2 diabetes is impaired insulin action, termed insulin resistance. Insulin resistance manifests itself as both a reduced maximal glucose elimination rate (GERmax) and an increased insulin concentration required to attain GERmax. Thus, to handle a given glucose load more insulin is required and that increased insulin concentration must be maintained for a longer period of time. Consequently, the diabetic patient is also exposed to elevated glucose concentrations for prolonged periods of time, which further exacerbates insulin resistance. Additionally, prolonged elevated blood glucose levels are themselves toxic to β cells.

Type 1 diabetes occurs as a result of the destruction of the insulin-producing cells of the pancreas (β-cells) by the body's own immune system. This ultimately results in a complete insulin hormone deficiency. Type 2 diabetes arises from different and less well understood circumstances. The early loss of early phase insulin release, and consequent continual glucose release, contributes to elevated glucose concentrations. High glucose levels promote insulin resistance, and insulin resistance generates prolonged elevations of serum glucose concentration. This situation can lead to a self-amplifying cycle in which ever greater concentrations of insulin are less effective at controlling blood glucose levels. Moreover, as noted above, elevated glucose levels are toxic to the β-cells, reducing the number of functional β-cells. Genetic defects impairing the growth or maintenance of the microvasculature nourishing the islets can also play a role in their deterioration (Glee, S. M., et al. *Nature Genetics* 38: 688-693, 2006). Eventually, the pancreas becomes overwhelmed, and individuals progress to develop insulin deficiency similar to people with type 1 diabetes.

Therapy

Insulin therapy is the standard treatment for type 1 diabetes. While incipient type 2 diabetes can be treated with diet and exercise, most early stage type 2 diabetics are currently treated with oral antidiabetic agents, but with limited success. Patients generally transition to insulin therapy as the disease progresses. These treatments, however, do not represent a cure.

In a typical progression the first oral antidiabetic agent used is metformin, a supressor of hepatic glucose output. Use of metformin is not associated with weight gain or hypoglycemia. If metformin treatment is insufficient to control hyperglycemia, an insulin secretagogue, most typically a sulfonylurea, can be added to the treatment regimen. Secretagogues raise the basal level of insulin in order to lower average blood glucose levels. Use of sulphonylureas is associated with weight gain and can lead to hypoglycemia, although severe hypoglycemia is infrequent. If this combination of two oral antidiabetic agents is inadequate to control hyperglycemia either a third oral agent, such as a glitazone, or a long-acting, basal insulin can be added to the regimen. As the disease progresses, insulin therapy can be intensified by the addition of intermediate and short (rapid) acting insulin preparations administered in association with at least some of the day's meals.

Current insulin therapy modalities can supplement or replace endogenously-produced insulin to provide basal and second-phase-like profiles but do not mimic early-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., *N Engl J Med* 353: 2643-53, 2005), but many patients are reluctant to accept the additional injections. Use of these conventional insulin preparations is associated with weight gain and a significant risk of hypoglycemia including severe, life-threatening hypoglycemic events.

Until recently, subcutaneous (SC) injection has been the only route of delivering insulin for self-administration by patients commercially available. However, SC insulin administration does not lead to optimal pharmacodynamics for the administered insulin. Absorption into the blood (even with rapid acting insulin analogues) does not mimic the prandial physiologic insulin secretion pattern of a rapid spike in serum insulin concentration. Subcutaneous injections are also rarely ideal in providing insulin to type 2 diabetics and may actually worsen insulin action because of delayed, variable and slow rate of absorption into the bloodstream. It has been shown, however, that if insulin is administered intravenously with a meal, early stage type 2 diabetics experience the shutdown of hepatic glucose release and exhibit increased physiologic glucose control. In addition their free fatty acids levels fall at a faster rate than without insulin therapy. While possibly effective in treating type 2 diabetes, intravenous administration of insulin is not a reasonable solution, as it is not safe or feasible for patients to intravenously administer insulin at every meal.

For a short period of time there was an inhalable insulin, EXUBERA® (Pfizer), which was marketed for the treatment of diabetes. This insulin preparation had a pharmacokinetic profile similar to the injectable rapid acting analogues and was used as a substitute for short acting insulin in the standard treatment paradigm. While this insulin preparation did allow patients using short acting insulins to avoid injections, it offered no other notable advantage which contributed to its commercial failure. Moreover, because its kinetic profile was so similar to subcutaneously administered regular and rapid-acting insulins, that after accounting for differences in bioavailability, its dosing and modes of administration could generally follow that of those subcutaneous insulins.

Though not yet commercially available, an ultrarapid acting insulin, insulin-fumaryl diketopiperazine (FDKP) has been under development. Growing experience with the use of this insulin formulation in human studies is showing that its unique kinetic profile can accommodate different dosing schemes and modes of administration as its use is applied to various situations and patient populations in order to achieve improved glycemic control. Such methods are the object of the present disclosure.

SUMMARY

Embodiments disclosed herein include methods useful for treating diabetes mellitus including both type 1 and type 2 using an ultrarapid acting insulin formulation. The disclosed methods relate to procedures for determining dosages, the use of standard dosages that are not adjusted from individual meal to meal, and the use of split dosages wherein the insulin formulation is administered at the beginning of the meal and at a subsequent point in time. In certain embodiments, the insulin formulation is insulin-FDKP and is administered by pulmonary inhalation. Such formulations can be advantageously used in the treatment of patients with subcutaneous insulin resistance, and methods of selecting such patients are also disclosed herein.

Embodiments of the method include administration of insulin in a manner that mimics the meal-related early phase insulin response. In mimicking early phase kinetics peak serum insulin levels can be reached within about 12 to within about 30 minutes of administration. Serum insulin levels can also return to approach baseline within about two or three hours of administration. Insulin preparations mimicking early phase kinetics in this manner are referred to herein as ultrarapid acting insulins. In one embodiment a dose sufficient to reduce or control glucose excursions is used. In one embodiment, insulin is administered to a patient in need of insulin therapy at mealtime, that is, within about 10 minutes, preferably 5 minutes before, or 30, 25, 15, or 10 minutes after starting a meal. (The shorter times after starting being preferred for patients with normal gastric emptying, the longer times after starting being appropriate for patients with delayed gastric emptying). In further embodiments, insulin is administered at least twice, initially at the beginning of the meal (that is within 10 minutes plus or minus of starting a meal) and a second time such as 30-120 minutes after beginning the meal or after the mealtime dose.

In preferred embodiments, a pulmonary delivery is achieved by inhalation of a dry powder formulation comprising fumaryl diketopiperazine (FDKP) associated with insulin. In such usage the term "fumaryl diketopiperazine" as used herein also includes the salts thereof. One such embodiment comprises insulin and an FDKP salt. In another such embodiment insulin is complexed with FDKP. For example insulin may be complexed (bound) to the surface of self-assembled crystalline FDKP microparticles, referred to herein generically as "insulin-FDKP", but also as TECHNOSPHERE® insulin (TI, MannKind Corp.). In other embodiments, FDKP is replaced by other C-substituted diketopiperazines, for example 3,6-di(succinyl-4-aminobutyl)-2,5-diketopiperazine ("succinyl diketopiperazine", SDKP). In an aspect of these embodiments delivery is facilitated by use of a unit dose inhaler such as the MEDTONE® inhaler system (MannKind Corp.) utilized in the examples below and described in U.S. Pat. Nos. 7,305,986 and 7,464,706 which are incorporated herein by reference in their entirety. Preferred dosages, based on fill for this system, are in the range of about 7.5 IU to 120 IU, particularly 15 to 90 IU, or greater than 24 IU of insulin complexed with fumaryl diketopiperazine, or the equivalent. Dosages can also be expressed as the dose emitted from the inhaler. These doses are preferably in the range of 6 U to 48 U per inhaler cartridge for patient dosages of 6 U to 72 or 96 U. As explained below dosages can be more universally expressed in subcutaneous equivalent (subQ eq) units. In these units preferred dosages are in the range of 1-32 or more units, for example 3, 6, 9 . . . or 4, 8, 12 . . . subQ eq units. For example with an alternative inhaler system as described in U.S. patent application Ser. Nos. 12/484,125, 12/484,129, and 12/484,137, dosages of 3-4 or 6-8 subQ eq units are obtained with cartridges filled with 10-11 or 20-22 IU, respectively.

In an embodiment, the insulin dose comprises a dose sufficient to control glucose excursions. In another embodiment, the insulin reaches peak serum levels within about 15 minutes of administration. In another embodiment, the peak serum insulin level is at least 60 mU/L. In still another embodiment, the peak serum insulin concentration is at least 60, 100, or 120 mU/L above the pre-dosing insulin concentration baseline. In one aspect of this embodiment, the recipient has type 2 diabetes. In another embodiment, the insulin dose is sufficient to control blood glucose levels. In yet another embodiment, the insulin dose is sufficient to reduce or suppress glucose release from the liver. In one aspect of this embodiment, the suppression lasts several hours (see FIG. 5). In one aspect of this embodiment a nadir in endogenous glucose production is reached more quickly than following subcutaneous administration of regular insulin or a rapid-acting insulin analogue, preferably in ≤60 minutes, more preferably in ≤50 minutes, still more preferably in about 40 minutes. In still another embodiment the dose is sufficient to maximally suppress endogenous glucose production.

Additional embodiments provide methods for improved treatment of patients with diabetes comprising selecting a patient in need of improved glycemic control, discontinuing current treatment, and routinely administering an ultrarapid acting insulin with at least two meals each day.

In other embodiments, the need for improved glycemic control is determined from HbA1c levels. In one embodiment, the level of serum HbA1c is ≤8%. In yet other embodiments, the level of serum HbA1c is ≤7.5%, ≤7.0%, ≤6.5%, or ≤6.0%. In other embodiments, the need for improved glycemic control is determined from elevated mean amplitude of glucose excursions or elevated post prandial blood glucose levels. In yet another embodiment, the patient has evidence of elevated oxidative stress and the oxidative stress is measured by 8-iso PGF(2a) levels. Elevated oxidative stress is correlated with elevated mean amplitude of glucose excursions.

In one aspect of these embodiments, the patient is further in need of avoiding weight gain, and treatment with the ultrarapid acting insulin does not result in weight gain or as much weight gain as expected from another mode of treatment. In a related embodiment, the patient is obese and/or in need of losing weight and treatment with the ultrarapid acting insulin results in weight loss, stable weight, or less weight gain as expected from another mode of treatment. Such embodiments can further comprise a step for assessing weight loss or less than otherwise expected weight gain. In one aspect of the invention the assessment is conducted at ≤12 weeks of treatment with meal-time ultrarapid acting insulin. In another aspect the assessment is conducted at ≤24 weeks. In yet other aspects the assessment is conducted at ≤36 week or ≤48 weeks.

In various embodiments, the method further comprises assessment of an improvement in glycemic control. In one embodiment, glycemic control is assessed as HbA1c level. In another embodiment, glycemic control is assessed as postprandial glucose excursion. In one aspect postprandial glucose excursion is assessed as postprandial blood glucose level. In another aspect it is assessed as oxidative stress, e.g. as 8-iso PGF(2a) levels or other indicators known in the art. In another embodiment, glycemic control is assessed as fasting blood glucose. In further embodiments, these factors are assessed in various combinations. In one aspect of embodiments, the assessment is conducted at ≤12 weeks of treatment with meal-time ultrarapid acting insulin. In another aspect, the assessment is conducted at ≤24 weeks. In yet other aspects the assessment is conducted at ≤36 week or ≤48 weeks.

In one embodiment, ultrarapid acting insulin is routinely administered with at least two meals each day. In another embodiment, ultrarapid acting insulin is administered with at least three meals each day. In another embodiment, ultrarapid acting insulin is administered with each main or substantive meal each day. In another embodiment, the ultrarapid acting insulin is administered with any meal containing more than 15 g of carbohydrate.

Some embodiments comprise modifying a current standard of care treatment regimen for diabetes by substituting prandial administration of an ultrarapid acting insulin preparation for one or another of the advocated treatments.

One embodiment provides methods for more effectively combining an ultrarapid acting insulin with a long acting insulin analog, for example insulin glargine. In this embodiment prandial administration of the ultrarapid acting insulin is combined with a morning dose of a long acting insulin analog administered within 6 hours of waking for a day. In aspects if this embodiment the long acting insulin analog dose is administered within 1, 2, 3, or 4 hours of waking. In one aspect of this embodiment the long acting insulin analog is insulin glargine. In another aspect of this embodiment the long acting insulin analog is insulin detemir. In related aspects the long acting insulin analog is insulin glargine and a second dose is administered from 8 to 14 hours after the morning dose. Alternatively the first dose is the only dose administered in the course of the day. In still another embodiment instead of using injections of a long acting insulin, an insulin pump is used to provide a continuous infusion of an insulin, for example regular human insulin. In one embodiment the ultrarapid acting insulin formulation comprises insulin and a diketopiperazine. In a particular embodiment the ultrarapid acting insulin formulation comprises insulin-FDKP.

Some embodiments comprise modifying a current standard of care treatment regimen for type 2 diabetes by substituting prandial administration of an ultrarapid acting insulin for treatment with an insulin secretagogue. Other embodiments comprise modifying a current standard of care treatment regimen for type 2 diabetes by substituting prandial administration of an ultrarapid acting insulin for treatment with an insulin sensitizer. Still other embodiments comprise modifying a current standard of care treatment regimen for type 2 diabetes by substituting prandial administration of an ultrarapid acting insulin for treatment with both an insulin secretagogue and an insulin sensitizer.

In one embodiment disclosed herein, a method is provided for treating diabetes type 2, comprising: selecting a patient with diabetes type 2 currently being treated with a suppressor of hepatic glucose output and an insulin secretagogue; discontinuing treatment with the insulin secretagogue; and routinely administering an ultrarapid acting insulin preparation with at least one established meal. In another embodiment, treatment with the suppressor of hepatic glucose output is also discontinued.

In another embodiment, the patient is further selected for having an insulin resistance at the lower portion of the insulin resistance spectrum. In yet another embodiment, the patient is further selected for needing to reduce or avoid weight gain. In yet another embodiment, the patient is further selected for having well or moderately controlled fasting blood glucose. In yet another embodiment, the patient is further selected for having an HbA1c level ≤8. In yet another embodiment, the patient is further selected for having an elevated mean amplitude of glucose excursions In yet another embodiment, the administering step does not comprise an injection and wherein patient is further a candidate for treatment with insulin and is further selected on the basis of being needle-phobic or desiring to avoid frequent injections.

In another embodiment, the suppressor of hepatic glucose output is metformin and the insulin secretagogue is a sulfonylurea. In one embodiment, the ultrarapid acting insulin preparation is administered by inhalation, such as a dry powder. In another embodiment, the ultrarapid acting insulin preparation comprises a fumaryl diketopiperazine (FDKP) associated with insulin such as insulin-FDKP.

In another embodiment, the ultrarapid acting insulin preparation is administered with each meal containing more than 15 g of carbohydrate. In another embodiment, ultrarapid acting insulin preparation is administered at a dosage sufficient to maximally reduce hepatic glucose output within 60 minutes of administration. In another embodiment, the ultrarapid acting insulin preparation is administered at a dosage within the range of 1 to 32 subcutaneous equivalent units.

In one embodiment, provided herein is a method of treating diabetes type 2, comprising: selecting a patient with diabetes type 2 currently being treated with a suppressor of hepatic glucose output who is in need of improved glycemic control and who would be a candidate for combination treatment with said suppressor of hepatic glucose output and an insulin secretagogue; and instead combining treatment with said suppressor of hepatic glucose output with routinely administering an ultrarapid acting insulin preparation with at least one established meal.

In one embodiment provided herein is a method of treating diabetes type 2, comprising: selecting a patient with diabetes type 2 currently being treated with an insulin sensitizer and an insulin secretagogue; discontinuing treatment with the insulin secretagogue; and routinely administering an ultrarapid insulin preparation with each meal. In another embodiment, treatment with the insulin sensitizer is also discontinued. In yet another embodiment, the patient is further selected for having an insulin resistance at the higher portion of the insulin resistance spectrum. In another embodiment, the insulin sensitizer is a thiazolidinedione (TZD) such as pioglitazone.

In one embodiment, provided herein is an improved method of treating hyperglycemia with a combination of an ultrarapid acting insulin and a long acting insulin analog comprising: prandial administration of the ultrarapid insulin, and administration of a dose of the long-acting insulin analog within 6 hours of waking for a day. In another embodiment, the hyperglycemia is resultant of diabetes type 2. In another embodiment, the administration of the long acting insulin analog is within 3 hours of waking. In another embodiment, the long acting insulin analog is insulin detemir or insulin glargine. In yet another embodiment, the long acting insulin is insulin glargine and the method further comprises administering a second dose of insulin glargine and the second dose is administered from 8 to 14 hours after said morning dose.

In another embodiment, the ultrarapid acting insulin comprises a formulation comprising insulin and a diketopiperazine, such as insulin-FDKP. In another embodiment, the ultrarapid acting insulin is administered by inhalation into the lungs.

In one embodiment, provided herein is an improved method of treating hyperglycemia with a combination of an ultrarapid acting insulin and an exogenous basal insulin comprising: prandial administration of the ultrarapid insulin, and continuous infusion of a short acting insulin with an insulin pump. In another embodiment, the short-acting insulin is regular human insulin or a rapid acting insulin analog. In another embodiment, the ultrarapid-acting insulin formulation is insulin-FDKP.

In one embodiment, provided herein is a method of controlling glycemia related to a daily meal without adjusting an insulin dose for meal content comprising the step of administering a predetermined dosage of an ultrarapid acting insulin formulation at mealtime for each daily meal. In another embodiment, the meal content is ≤25%, ≤50%, ≤150%, or ≤200% of a usual meal content as used in determination of the predetermined dose.

In one embodiment, provided herein is a method of controlling glycemia related to a daily meal for a patient with delayed or prolonged nutrient absorption comprising the steps of: selecting a patient with delayed nutrient absorption; administering 50% to 75% of a predetermined dosage of an ultrarapid-acting insulin formulation at mealtime for the daily meal; and administering the remainder of the predetermined dosage 30 to 120 minutes after beginning the daily meal. In another embodiment, the ultrarapid acting insulin formulation is insulin-FDKP.

In another embodiment, the delayed nutrient absorption is related to a disease state. In yet another embodiment, the delayed nutrient absorption is related to a meal content high in fat or fiber. In yet another embodiment, the prolonged nutrient absorption is related to a prolonged meal.

In one embodiment, provided herein is a method of controlling glycemia related to a daily meal wherein insulin dosage is adjusted to the glycemic load of the meal consumed comprising the steps of: administering an initial predetermined dose of an ultrarapid acting insulin formulation at mealtime for the daily meal; determining postprandial blood glucose 1 to 2 hours after beginning the daily meal; and if the postprandial blood glucose is >140 mg/dl administering a second dose of the ultra rapid acting insulin formulation wherein the second dose is 25% to 100% of the initial dose. In another embodiment, the ultrarapid acting insulin formulation is insulin-FDKP.

In one embodiment, provided herein is a method of treating diabetics with subcutaneous insulin resistance comprising the steps of: selecting a patient with subcutaneous insulin resistance on the basis of atypically high insulin dosage; discontinuing treatment with subcutaneously administered rapid-, short-, or intermediate-acting insulin formulations; and initiating treatment by administration of prandial doses of insulin-FDKP by inhalation effective for the control of postprandial hypoglycemia.

In another embodiment, the atypically high insulin dosage is ≤2 units/Kg/day. In another embodiment, the selecting step further comprises selection of the basis that the patient has normal or near-normal levels of endogenous basal insulin. In yet another embodiment, the level of endogenous basal insulin is ≥50 µU/ml.

In another embodiment, the selecting step further comprises one of the following: selection on the basis of injection site lipoatrophy or lipodystrophy; selection of the basis of the patient having 2 HbA1c level determinations ≥9% in a 6 to 9 month period while on an intensified insulin regimen; or selection of the basis of the patient having life threatening glycemic instability characterized by periods of hyperglycemia and/or hypoglycemia despite adherence to their insulin regimen and any diet or exercise regimen.

In another embodiment, the method further comprises the step of confirming the patient has subcutaneous insulin resistance by determining that a similar or improved degree of glycemic control is achieved with a substantially lower dosage of insulin after adjustment based on relative bioavailability.

In one embodiment, provided herein is a method for determining an individual's dosage of an ultrarapid acting insulin for a daily meal comprising the steps of: administering a low dose of the ultrarapid acting insulin at mealtime for the daily meal for which the dosage is being titrated each day for at least 3 days within a titration period of not more than a week; iteratively increasing the dosage by the amount of the low dose in each subsequent titration period and administering at mealtime for the daily meal for which the dosage is being titrated each of at least three days in the titration period until a titration endpoint is reached.

In another embodiment, the low dose is provided in a unit dose cartridge. In another embodiment, titration period is 3 days or one week. In another embodiment, the low dose is 1-5 subQ eq units. In another embodiment, the ultrarapid acting insulin formulation is insulin-FDKP.

In another embodiment, the titration endpoint is selected from: 1) achieving a 2-hour post-prandial median glucose less than 160 mg/dl or alternatively less than 140 mg/dl, or a median glucose just prior to the next meal that is between 70 and 110 mg/dl, 2) the dosage based on subcutaneous equivalent (subQ eq) units is a maximal dosage, 3) an episode of severe hypoglycemia with a confirmed SMBG<36 mg/dl occurs and the dosage is decreased by the equivalent of one low-dose cartridge, and 4) an episode of mild to moderate hypoglycemia with a confirmed SMBG of <70 mg/dl occurs, the dosage is decreased by the equivalent of one low dose cartridge for one week and then the titration is resumed until it reaches any of said endpoints 1-3 or the dosage is set at the level below that which again produces the mild to moderate hypoglycemia.

In another embodiment, the dosages for two or more daily meals are titrated concurrently. In another embodiment the dosages for two or more daily meals are titrated successively from the daily meal resulting in the highest 2-hour postprandial blood glucose to the daily meal resulting in the lowest 2-hour postprandial blood glucose.

In another embodiment, the maximal dosage is 24 subQ eq units or 32 subQ eq units.

The entire disclosures of U.S. Ser. No. 14/102,383 filed Dec. 10, 2013, U.S. Ser. No. 13/351,855 filed Jan. 17, 2012, now U.S. Pat. No. 8,623,817, U.S. Ser. No. 12/539,459 filed Aug. 11, 2009, now U.S. Pat. No. 8,119,593, U.S. 61/087,943 filed Aug. 11, 2008, 61/097,495 filed Sep. 16, 2008, 61/097,516 filed Sep. 16, 2008, and 61/138,863 filed Dec. 18, 2008, are each incorporated herein by reference in their entirety.

The entire disclosures of U.S. Ser. No. 13/357,821, filed Jan. 25, 2012, U.S. Ser. No. 12/539,499 filed Aug. 11, 2009, now U.S. Pat. No. 8,258,095, U.S. 61/087,943 filed Aug. 11, 2008, 61/097,495 filed Sep. 16, 2008, 61/097,516 filed Sep. 16, 2008, and 61/138,863 filed Dec. 18, 2008, and 61/972,159, filed Mar. 28, 2014, are each incorporated herein by reference in their entirety.

BRIEF DESCRIPTION OF THE DRAWINGS

FIG. 16 depicts the baseline demographics of patients enrolled in the study of FIG. 15.

DEFINITION OF TERMS

Figure 1:
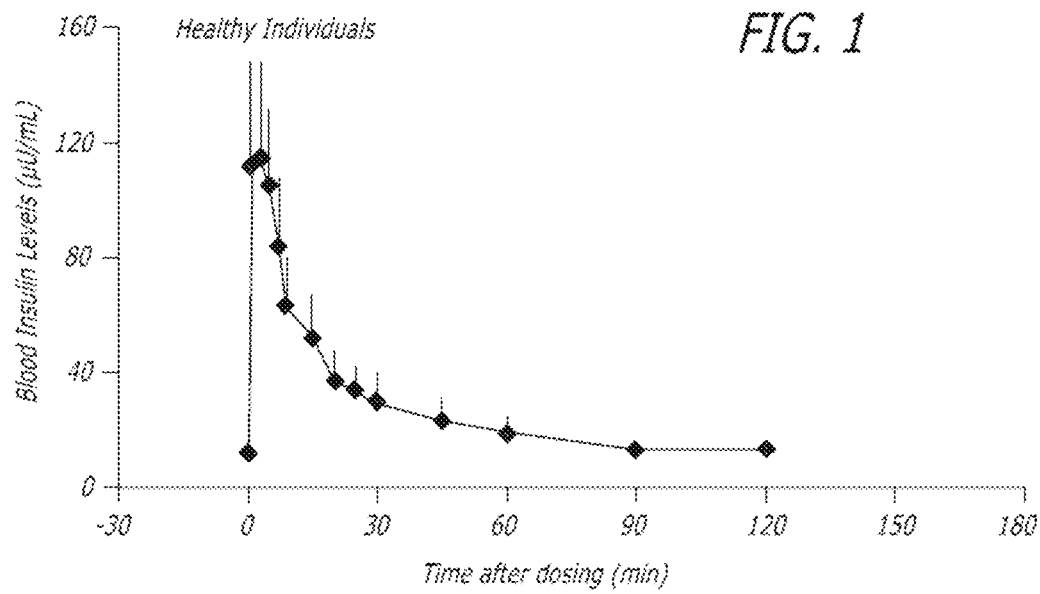
FIG. 1 depicts the measurement of first-phase insulin release kinetics following artificial stimulation by bolus glucose infusion.
Figure 2:
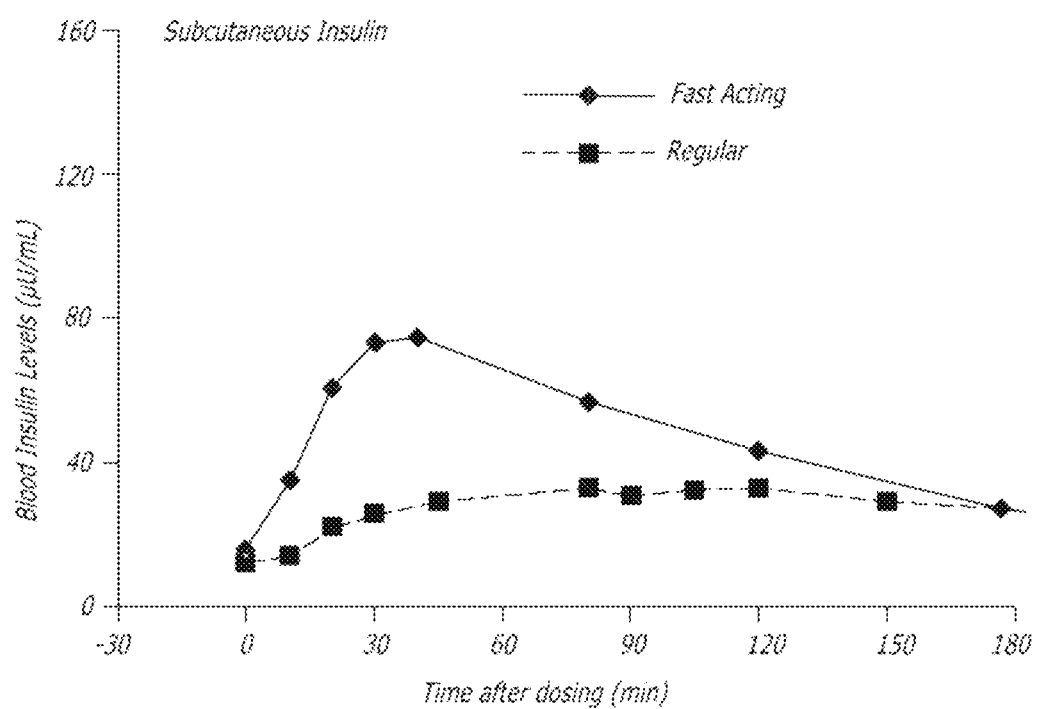
FIG. 2 depicts serum insulin concentration after administration of subcutaneous (SC) regular human insulin or SC fast acting insulin (NOVOLOG™) NOVOLOG™ is a registered trademark of Novo Nordisk Pharmaceuticals, Bagsvaerd, Denmark.

Prior to setting forth the detailed disclosure, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

First-Phase: As used herein, "first-phase" refers to the spike in insulin levels as induced by a bolus intravenous injection of glucose. A first-phase insulin release generates a spike in blood insulin concentration that is a rapid peak which then decays relatively quickly.

Early phase: As used herein "early phase" refers to the rise in blood insulin concentration induced in response to a meal which peaks within 20-30 minutes. The distinction between early phase and first phase is not always carefully adhered to in the general literature.

Excursion: As used herein, "excursion" refers to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

Glucose elimination rate: As used herein, "glucose elimination rate" (GER) is the rate at which glucose disappears from the blood. Using a glucose clamp it can be determined as the glucose infusion rate required to maintain stable blood glucose, often around 120 mg/dL during a glucose clamp experimental procedure. This glucose elimination rate is equal to the glucose infusion rate, abbreviated as GIR.

Honeymoon phase: As used herein, the "honeymoon phase" of type 1 diabetes refers to the early stages of the disease characterized by loss of early phase insulin release and the remaining β-cell function produces some insulin, which is released with second-phase kinetics.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL (3.5 mM). Clinically relevant hypoglycemia is defined as blood glucose concentration below 63 mg/dL or causing patient symptoms such as cognitive impairment, behavioral changes, pallor, diaphoresis hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal.

Insulin composition: As used herein, "insulin composition" refers to any form of insulin suitable for administration to a mammal (for example, human insulin) and includes insulin isolated from mammals, recombinant insulin, insulin associated or derivatized with other molecules, and insulin molecules with altered sequences, so long as they retain clinically relevant blood glucose lowering activity. Also included are compositions of insulin suitable for administration by any route including pulmonary, subcutaneous, nasal, oral, buccal and sublingual. Insulin compositions can be formulated as dry powders, aqueous solutions or suspensions, or non-aqueous solutions or suspensions (as is typical for metered dose inhalers) for inhalation; aqueous solutions or suspensions for subcutaneous, sublingual, buccal, nasal or oral administration; and solid dosage forms for oral and sublingual administration.

Insulin-related disorder: As used herein, "insulin-related disorders" refers to disorders involving production, regulation, metabolism, and action of insulin in a mammal. Insulin-related disorders include, but are not limited to, pre-diabetes, type 1 diabetes mellitus, type 2 diabetes mellitus, hypoglycemia, hyperglycemia, insulin resistance, secretory dysfunction, loss of pancreatic β-cell function, and loss of pancreatic β-cells.

Non-insulin dependent patients having insulin-related disorders: As used herein "non-insulin dependent patients having insulin-related disorders" refers to patients with disorders for which therapy with exogenously-provided insulin is not the current standard treatment upon diagnosis. Non-insulin dependent patients having insulin-related disorders which are not treated with exogenously-administered insulin include early type 2 diabetes, type 1 diabetes in the honeymoon phase, pre-diabetes and insulin-producing cell transplant recipients.

Insulin resistance: As used herein, the term "insulin resistance" refers to the inability of a patient's cells to respond to insulin appropriately or efficiently. The pancreas responds to this problem at the cellular level by producing more insulin. Eventually, the pancreas cannot keep up with the body's need for insulin and excess glucose builds up in the bloodstream. Patients with insulin resistance often have high levels of blood glucose and high levels of insulin circulating in their blood at the same time.

Insulin resistance spectrum: As used herein "insulin resistance spectrum" refers to the range over which the degree to which a patient is resistant to insulin can vary. It is well understood that from person to person, and from one point in the progression of type 2 diabetes to another the degree of insulin resistance can differ. Although there are no generally accepted units of insulin resistance it is well within the ability of one of ordinary skill in the art to recognize a lower degree of insulin resistance as opposed to a higher degree of insulin resistance. Ideally insulin resistance can be measured with euglycemic clamp procedures, but these are not practical for routine use. Simpler assessments include HOMA (see Matthew D R, Hosker J P, Rudenski A S, et al., Homeostasis model assessment: insulin resistance and β-cell function from fasting plasma glucose and insulin concentrations in man, *Diabetologia* 1985; 28:412-419) and the related QUICKI (Katz A, Nambi S S, Mather K, Baron A D, Follmann D A, Sullivan G, Quon M J. Quantitative insulin sensitivity check index: a simple, accurate method for assessing insulin sensitivity in humans. *J Clin Endocrinol Metab.* 2000 July; 85(7): 2402-10). Fasting serum insulin levels themselves can also be used as an indicator of the degree of insulin resistance with concentrations of 50-100 pmol/L indicating resistance at the lower end of the spectrum and concentrations of 300 pmol/L indicating resistance at the higher end of the spectrum. Finally, for patients already on an insulin treatment, the total daily dose is commonly taken as an indicator of whether the subject has a high or low degree of insulin resistance.

Intermediate acting insulin: As used herein, "intermediate acting insulin" or lente insulin, refers to an insulin with an onset of action usually about two to four hours after injection and peaks four to 12 hours after injection, and it keeps working for 10 to 18 hours. Typical intermediate acting insulins are obtained by mixing regular insulin with a substance that makes the body absorb the insulin more slowly. A non-limiting example is NPH insulin. Intermediate acting insulin can provide many of the benefits of long acting insulin.

Long acting insulin: As used herein, the term "long acting insulin" refers to an insulin formulation that starts working within about 1-6 hours and provides a continuous level of insulin activity for up to 24 hours or more. Long-acting insulin operates at maximum strength after about 8-12 hours, sometimes longer. Long-acting insulin is usually administered in the morning or before bed. Non-limiting examples of long acting insulin include, but are not limited to, insulin glargine or insulin detemir, which are insulin analogs, and ultralente insulin which is regular human insulin formulated to slow absorption. Long acting insulin is best suited to provide for basal, as opposed to prandial, insulin requirements.

Meal: As used herein, "meal", "meals", and/or "mealtime", etc. include traditional meals and meal times; however, these also include the ingestion of any sustenance regardless of size and/or timing. As used herein "established meal" refers specifically to the daily periods of primary food consumption such as the usual or traditional three daily meals. Some diabetics are encouraged to eat four somewhat smaller daily meals to reduce peak blood glucose levels; such meals are also included within the meaning of the term established meal.

Microparticles: As used herein, the term "microparticles" includes microcapsules having an outer shell composed of either a diketopiperazine alone or a combination of a diketopiperazine and one or more drugs. It also includes microspheres containing drug dispersed throughout the sphere; particles of irregular shape; and particles in which the drug is coated on the surface(s) of the particle or fills voids therein.

Prandial: As used herein, "prandial" relates something to a meal or a snack. Depending on context in can refer to a period of time less than an hour after beginning a meal, or for as long as consumption of food continues.

Periprandial: As used herein, "periprandial" refers to a period of time starting shortly before and ending shortly after the ingestion of a meal or snack.

Postprandial: As used herein, "postprandial" refers to a period of time, generally an hour or more, after beginning a meal and after ingestion of a meal is completed. As used herein, late postprandial refers to a period of time beyond 2 hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Pre-Diabetic: As used herein, the term "pre-diabetic" refers to a patient with impaired fasting glucose impaired glucose tolerance, that is with a fasting blood glucose level between 100 mg/dL (5.5 mmol/L) and 126 mg/dL (7.0 mmol/L), or a 2 hour post-prandial blood glucose level between 140 mg/dL (7.8 mmol/L) and 200 mg/dL (11.1 mmol/L).

Rapid acting insulin: As used herein, the term "rapid acting insulin" refers to an insulin formulation that reaches peak blood concentration in approximately 45-90 minutes and peak activity approximately one to 3 hours after administration. Rapid acting insulin can remain active for about four to six hours. A non-limiting example of a rapid acting insulin is the insulin analog insulin lispro (HUMALOG®). The withdrawn product EXUBERA® and the experimental formulation VIAJECT® (Biodel Inc.), both based on regular human insulin, have kinetic profiles falling within this definition.

Second-Phase: As used herein, "second-phase" refers to the non-spiking release of insulin in response to elevated blood glucose levels. This is distinct from "second-phase kinetics" which refers to the slow decay of modestly elevated blood insulin levels back to baseline.

Short acting insulin: As used herein the term "short acting insulin" includes regular insulin and the rapid acting preparations, typically used around mealtimes.

Snack: As used herein "snack" refers specifically to food consumed between established meals.

Suppressor of hepatic glucose output: As used herein, the phrase "suppressor of hepatic glucose output" refers to drugs which suppress hepatic glucose production (hepatic gluconeogenesis, mobilization from glycogen stores). A non-limiting example of a suppressor of hepatic glucose output is metformin.

TECHNOSPHERE® Insulin: As used herein, "TECHNOSPHERE® Insulin" or "TI" refers to an insulin composition comprising regular human insulin and TECHNOSPHERE® microparticles, a drug delivery system. TECHNOSPHERE® microparticles comprise a diketopiperazine, specifically 3,6-di(fumaryl-4-aminobutyl)-2,5-diketopiperazine (fumaryl diketopiperazine, FDKP). Specifically, TECHNOSPHERE® Insulin comprises a FDKP/human insulin composition. TECHNOSPHERE® Insulin is an ultrarapid acting insulin as delivered by pulmonary administration and mimics physiologic mealtime early phase insulin release. This formulation is also referred to generically herein as "insulin-FDKP". In some contexts the product is referred to as insulin monomer human [rDNA origin] inhalation powder.

As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

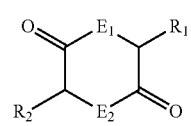

Formula 1

Diketopiperazine microparticles, in addition to making aerodynamically suitable microparticles enabling delivery to the deep lung, also rapidly dissolve and release any drug cargo further speeding absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In another embodiment of the present invention, the DKP is a derivative of 3,6-di(4-aminobutyl)-2,5-diketopiperazine, which can be formed by (thermal) condensation of the amino acid lysine. Exemplary derivatives include 3,6-di (succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in co-pending U.S. patent application Ser. No. 11/210,710 filed Aug. 23, 2005, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety.

TECHNOSPHERE®/Placebo: As used herein, "TECHNOSPHERE®/Placebo" refers to TECHNOSPHERE® particles which are not associated with insulin or other active agent.

Tmax: As used herein, the term "Tmax" refers to the time from administration for a parameter (such as concentration or activity) to reach its maximum value.

Units of measure: Subcutaneous and intravenous insulin dosages are expressed in IU which is defined by a standardized biologic measurement. Amounts of insulin formulated with fumaryl diketopiperazine are also reported in IU as are measurements of insulin in the blood. TECHNOSPHERE®/Insulin dosages are expressed in arbitrary units (U) which are numerically equivalent to the amount of insulin formulated in the dosage.

DETAILED DESCRIPTION

Insulin-FDKP was discovered to be an ultrarapid acting insulin capable of mimicking physiologic mealtime early phase insulin release. In exploring how an insulin preparation with this unique pharmacokinetic profile might be used advantageously in the treatment of type 2 diabetes, it has up to now been evaluated in comparison to other insulin preparations (see for example U.S. patent application Ser. Nos. 11/032,278, 11/329,686, 11/278,381, and 11/461,746, each of which are hereby incorporated by reference in their entirety). Embodiments disclosed herein are concerned with how specific dosages and modes of administration for such insulin preparations can be chosen for individual patients and applied to various patient populations for advantageous effect. Certain embodiments are concerned with how such insulin preparations can be used in combination with and/or in place of oral antidiabetic medications, particularly insulin sensitizers and insulin secretagogues, to achieve similar or advantageous effect. Certain other embodiments are concerned with how such insulin preparations can be used in combination with and/or in place of exogenously provided basal insulins to achieve similar or advantageous effect. Similar disclosure is also found in U.S. Provisional patent application Nos. 61/087,943, 61/097,495, 61/097,516, and 61/138,863, each of which is incorporated herein by reference in its entirety.

In general, various embodiments involve the use of prandial ultrarapid acting insulin in defined populations. These populations may be referred to as being in need of, capable of benefiting from, or desirous of receiving the benefit of one or another or more of the advantages offered by the various methods described. Such advantages can be expressed as receiving or seeking some stated clinical benefit. Such advantages can also include elimination or avoidance of various side-effects, adverse outcomes, contraindications, and the like, or reducing the risk or potential for them to occur. Similarly the methods can involve a step of selecting a patient on the basis of being part of one or another of populations. It should be understood that selecting can comprise a physician or other healthcare professional evaluating a patient in respect to the particular parameters but can also comprise a self-selection by the patient to be treated on the basis of similar data or in accepting the advice of the physician or other healthcare professional. In like manner, administering steps of these methods can comprise the physical taking of a medicament (or similarly discontinuing treatment with a medicament) by a patient but can also comprise a physician or other healthcare professional prescribing or providing other specific instruction to take (or discontinue) a medicament. Further embodiments of the invention include use of ultrarapid acting insulin preparations, compositions, or formulations for such purposes, and in the manufacture of medicaments for such purposes.

As used herein, mimicking physiologic mealtime early phase insulin release (or similar terms) does not necessarily indicate exact replication of all features of the physiologic response. It can refer to insulin preparations and methodologies producing a spike or peak of insulin concentration in the blood that constitutes both a relatively quick rise and fall in concentration. In certain embodiments, the rise to peak concentration takes less than 30 minutes, preferably less than about 20 minutes or 15 minutes and in further embodiments takes at least 5 or at least 10 minutes to peak; for example reaching a peak concentration in 12-14 minutes or 10-20 minutes, etc., from administration or first departure from baseline. In certain embodiments the fall from the peak insulin concentration involves descent through half maximal by 80 minutes, alternatively 50 minutes, or alternatively 35 minutes after peak. Typically insulin concentration will be approaching baseline with 2 to 3 hours of administration. This is in contrast to insulin preparations and methods producing a more gradual rise (from 30 minutes to several hours) to the maximal insulin concentration achieved and a prolonged plateau near maximal concentrations. The rapid acting analogs (RAA) do show a greater degree of peaking that regular human insulin, but even the fastest of the commercially available RAAs, as disclosed in their prescribing information, insulin lispro (HUMALOG®) reports a Tmax of 30-90 minutes. For comparison, insulin aspart (NOVOLOG®) reports a median Tmax of 40-50 minutes in subjects with type 1 diabetes and insulin glulisine (APIDRA®) reports a median Tmax of 60 and 100 minutes in subjects with type 1 and type 2 diabetes, respectively with a range of 40-120 minutes in both populations. Moreover the RAAs require approximately 6 hours for concentration to return to baseline. Mimicking physiologic mealtime early phase insulin release can also refer to insulin preparations and methodologies in which the spike in insulin concentration can be reliably coordinated with the start of a meal. It can also refer to the achievement (and associated methodologies) of a maximal glucose elimination rate (GERmax) within about 30-90 minutes, preferably around 45-60 minutes, after administration. Insulin preparations with such characteristics are referred to herein as ultrarapid acting. In embodiments of the invention a methodology that mimics early phase release is generally also one that can be practiced by diabetics upon themselves without special medical training, such as training in intravenous injection. Special medical training would not include training to use medical devices, such as dry powder inhalers, that are routinely used by persons who are not trained medical professionals. In some embodiments ultrarapid acting insulin can be administered with every ingestion of any sustenance regardless of size and/or timing. Nonetheless it is preferred that insulin be administered only for a meal providing at least a threshold glycemic load (which can depend on the insulin dose) so as to avoid a risk of hypoglycemia. Various methods of assessing glycemic load are known in the art including "carb counting" (calculating/estimating the number of grams of carbohydrate in a meal), the use of bread exchanges, and consideration of the glycemic index of the foods to be consumed.

The meaning of ultrarapid can also be understood by further comparison to other insulin preparations. Regular human insulin preparations for subcutaneous injection are considered short acting, referring primarily to their duration of action. Typically they will take at least 1-2 hours to reach maximal blood insulin concentration and can take 2-4 hours to reach maximal activity. Significant elevation or activity can last for as long as 10-12 hours. Other short acting insulins include the rapid acting insulin analogs such as insulin aspart, insulin glulisine, and insulin lispro. Because these insulin preparations more readily dissociate from hexamer to monomer upon injection they reach peak blood concentrations sooner (30-100 minutes) and consequently also have a faster onset of action than regular human insulin. Insulin preparations for pulmonary administration, such as the now withdrawn product EXUBERA® display pharmacodynamics similar to the rapid acting analogs. A comparison of the pharmacodynamic profiles of several pulmonary formulations, insulin lispro, and insulin-FDKP has been published showing that insulin-FDKP is distinctly faster in reaching maximal activity and declines toward baseline sooner (Heinemann et al. Br J Diab Dis 4: 295-301, 2004). Thus, whereas an ultrarapid acting insulin will have expended approximately two thirds of its insulin lowering activity within 2 hours after administration these other preparations will typically have expended about a third or less of their insulin lowering activity in that same time frame. At the other end of the spectrum are the long acting insulins, such as insulin glargine or insulin detemir which ideally provide a constant level of insulin activity over long periods of time, for example up to 24 hours. These are intended to provide basal activity and are typically administered once or twice a day. As such the rapidity of onset of action is not a critical parameter. Finally there are insulin preparations, termed intermediate acting, with durations of action between the short and long acting products.

The potentiation of GER contributing to the rapid attainment of GERmax is understood to depend not only on the rapidity of the rise in insulin concentration, but also on achieving sufficient peak height. For type 1 diabetics this is a peak insulin concentration of at least about 60 mU/L, preferably at least about 80 mU/L. For type 2 diabetics the insulin resistance that is part of the condition can necessitate higher insulin concentrations; typically at least about 100 mU/L, preferably at least about 120 mU/L, at least about 140 mU/L, or more, depending on the degree of resistance. Thus in various embodiments the peak height is at least 60, 100, or 120 mU/L above the pre-dosing insulin concentration baseline. These peak insulin concentrations are substantially higher than those attained with typical doses of non-spiking insulin products such as standard preparations for subcutaneous administration, including those termed rapid- or fast-acting, and preparations for non-injected administration having similar kinetics that have been described.

The comparatively slow and shallow rise in insulin concentration and prolonged period of action associated with insulin preparations that do not mimic early phase release limits their ability to control glucose excursions. The dose that can be given is generally inadequate to control the rise in blood glucose following a meal due to the need to avoid inducing hypoglycemia after the glycemic load from the meal has been abated. These issues are further discussed in co-pending U.S. patent application Ser. No. 11/278,381, which is incorporated herein by reference in its entirety. It is emerging that acute fluctuations in blood glucose concentrations (measured for example as MAGE: mean amplitude of glycemic excursions) have a greater effect than chronic hyperglycemia (typically measured as Hb1Ac level) on diabetes-associated oxidative stress, and thus is an important parameter to control to avoid diabetic complications attributable to such stress (see Monnier, L., et al. *JAMA* 295: 1681-1687, 2006; and Brownlee, M. & Hirsch, I. *JAMA* 295: 1707-1708, which are incorporated herein by reference in their entirety). It is the applicant's further understanding that a high surge and rapid rate of change in insulin concentration suppresses glucagon production, reducing hepatic glucose release. This results in lessened glycemic load and consequently lessened demand for insulin and reduced glucose excursion.

Ultrarapid acting insulin is particularly well suited to the control of postprandial blood glucose (PPG). (For a review of the significance of PPG see MannKind Corporation. Postprandial hyperglycemia: Clinical significance, pathogenesis, and treatment. Valencia, Calif.: MannKind Corporation; 2009:1-20). The ultrarapid kinetics not only enable better matching of insulin activity to the time when glucose is being absorbed from a meal, there is also similarly quicker and advantageously timed suppression of hepatic glucose output (see Example 1). Thus it addresses both sources of glucose contributing to postprandial hyperglycemia. Embodiments disclosed herein seek to constrain 1 and 2 hour PPG to ≤140 mg/dl, ≤180 mg/dl, or ≤200 mg/dl. Surprisingly, it has also become apparent that control of PPG levels has long term beneficial effects on fasting blood glucose levels as well. Through consideration of these properties and the data from clinical use presented in the Examples below, it is herein disclosed how ultrarapid acting insulins such as insulin-FDKP may be advantageously used in particular patient populations alone or in combination with standard oral antidiabetic medications and in contrast to current treatment paradigms.

Treatment of diabetes has traditionally focused on controlling average blood glucose concentrations, as reflected by Hb1Ac levels. The presently disclosed methods are designed to minimize not only Hb1Ac levels (average blood glucose concentration) and attendant glucose toxicity; but also to control acute fluctuations in glucose concentration (glucose excursions). The reduction of glucose excursions also relieves the general inflammatory burden and oxidative damage to microvasculature resulting from oxidative stress. Thus even for patients in whom substitution of ultrarapid insulin for one or more oral medications may result in only similar control of HbA1c levels the treatment can confer a benefit over treatment with oral medications alone. Indeed this is a benefit that is also not attainable by addition of basal insulin to the treatment regimen. Nor can the merely rapid acting insulins be expected to deliver this benefit in full measure, especially as compared to an optimized dose of an ultrarapid acting insulin.

This benefit is accomplished by routinely administering an insulin preparation that mimics early phase release, that is an ultrarapid acting insulin preparation, in conjunction with at least one, preferably at least two or three meals a day, or with every established meal, or with every meal including snacks. Such treatment should be maintained, in increasing preference and for increasing effectiveness, for any number of days, weeks, months, and years, up to the remainder of the patient's life (or until such time as the underlying insulin-related disorder is cured or otherwise alleviated). By routinely it is meant that the advocated schedule of administration is the ideal and usual usage, but real world practice deviations from this protocol, such as occasional missed meals or missed doses, do not depart from the scope of the claimed invention. In various embodiments insulin is routinely administered with any meal or snack that would otherwise cause blood glucose to exceed 140 mg/dL, or alternatively 180 mg/dl; with any meal or snack constituting 1, 2, 3, or more bread exchanges; with any meal or snack containing more than about 15, 20, 30, or 45 g of carbohydrate.

Embodiments of the methods disclosed herein include a variety of dosing regimens including, but not limited to, dosing at every meal or snack, dosing at every meal or snack having a carbohydrate content of more than 15 g, dosing at every meal or snack having a carbohydrate content of more than 30 g, every meal or snack having a carbohydrate content of more than 45 g. Dosages and desired insulin composition concentrations may vary depending on the particular use envisioned. The determination of the appropriate dosage or route of administration is generally within the skill of an ordinary physician. However physicians are most commonly familiar with liquid formulations of insulin which allow for the continuous variation of dose. Insulin-FDKP is supplied as a dry powder in premeasured unit doses. Therefore specific instructions for determining the appropriate dosages of insulin-FDKP for an individual are disclosed herein. Furthermore the length of treatment may vary on the particular use and determination of the length of treatment is within the skill of an ordinary physician.

The rapid absorption and lack of a substantial tail in the activity profile of ultrarapid acting insulin preparations, such as insulin-FDKP, also mean that they pose a reduced potential for inducing hypoglycemia as compared to other insulins. Snacking to counteract late postprandial hypoglycemia is understood to contribute to the weight gain associated with standard insulin therapies. In contrast, use of insulin-FDKP has been associated with a lack of weight gain; indeed weight loss has been observed.

Intravenous injection of insulin can effectively replicate the first phase response and approximate the early phase response, but is not a practical therapy for a lifelong condition requiring multiple daily administrations. For these reasons, insulin for intravenous injection is not contemplated by the term ultrarapid acting insulin preparations as used herein. Traditional subcutaneous injections are absorbed into the bloodstream slowly by comparison, even using fast acting formulations, which still take up to an hour to reach maximal concentration in the blood and have a plateau lasting several hours. Many pulmonary formulations that have been assessed are equivalent to subcutaneous insulin in effectiveness and similarly fail to achieve the ultrarapid kinetics needed to mimic early phase release, as defined above. Nonetheless, the potential does exist for truly fast absorption using a non-intravenous based delivery, such as pulmonary and oral administration or subcutaneous injection of formulations comprising absorption promoting excipients. As described herein, pulmonary delivery using diketopiperazine-based dry powder formulations have been utilized.

Thus, a preferred embodiment provides a method to achieve the desirable early phase-like kinetics through pulmonary administration of a dry powder insulin formulation containing insulin complexed to diketopiperazine microparticles. This formulation is rapidly absorbed reaching peak serum levels within about 10 to 15 minutes. This is fast enough to mimic the kinetics of the physiologic meal-related early phase insulin response. The short, sharp rise to peak serum insulin concentration is critical to the rapid suppression of endogenous glucose production and has the additional effect of compressing the bulk of insulin action to the peri-prandial time interval, in contrast with slower acting formulations. This reduces the magnitude and duration of any meal-related excursions from normal glucose levels and associated glucose toxicity, as well as the risk of postprandial hypoglycemia. Such improved control of blood glucose levels obtainable with this dry powder insulin is more fully described in co-pending U.S. patent application Ser. No. 11/278,381, filed Mar. 31, 2006, which is incorporated herein by reference in its entirety. As disclosed in U.S. application Ser. No. 11/329,686 and noted above, prior high insulin levels potentiate glucose elimination rate, meaning glucose can be eliminated more quickly if there is a prior high insulin concentration spike.

Diketopiperazine microparticle drug delivery systems and associated methods are described in U.S. Pat. Nos. 5,352,461 and 5,503,852. The use of diketopiperazine and biodegradable polymer microparticles in pulmonary delivery is described in U.S. Pat. Nos. 6,428,771 and 6,071,497. Details regarding various aspects of possible formulation and manufacturing processes can be found in U.S. Pat. Nos. 6,444,226 and 6,652,885; in U.S. Pat. No. 6,440,463; in U.S. Provisional Patent Application Nos. 60/717,524, filed Sep. 14, 2005; and 60/776,605, filed Apr. 14, 2006. The properties and design of a preferred breath-powered dry powder inhaler system is disclosed in U.S. patent application Ser. No. 10/655,153. Aspects of treatment using insulin complexed to diketopiperazine microparticles are disclosed in U.S. Pat. No. 6,652,885 as well as in co-pending U.S. patent application Ser. No. 11/032,278. Additionally U.S. patent application Ser. No. 11/210,710 discloses the use of diketopiperazine salts to formulate insulin for both pulmonary and oral delivery. Each of the patents and patent applications mentioned in this paragraph is herein incorporated by reference in its entirety.

Whether insulin-FDKP or another insulin mimicking early phase release is administered alone or in conjunction with another agent, such as basal insulin, a suppressor of hepatic glucose release such as metformin, or an insulin sensitizing medication for example a thiazolidinedione (TZD), the ultrarapid acting insulin is administered in association with established meals, at least once and preferably two to four times daily, or more times up to with every meal, depending upon need. In order to achieve the maximum benefit of the treatment, it should be taken over an extended period of time, preferably at least 12 weeks, more preferably at least 24 weeks still more preferably from about 6 months to about two years, and most preferably for the remaining life of the patient or until the underlying diabetes is cured.

Current treatment of diabetes generally aims to reduce HbA1c levels to 7% or below. HbA1c levels above 8% indicate that patient's current therapy should be re-evaluated. It may be desirable to achieve normal HbA1c levels, but with the currently marketed insulin products this could only be accomplished at an unacceptable risk of severe hypoglycemia. Thus patients with HbA1c levels below 8% would not usually be considered candidates for more intensive treatment, that is, for treatment with insulin especially the current prandial insulins. Even those with HbA1c above 8% but not yet receiving basal or mixed insulin would not be considered to be candidates for treatment with a prandial insulin regimen. In embodiments disclosed herein the risk of hypoglycemia is much reduced, in part due to the lack of a tail of insulin activity exhibited by ultrarapid acting insulin, and it is possible to treat patients with HbA1c below 7%. Additionally, benefit can be expected from lowering blood glucose even at the high end of the normal range. For example one study showed that the risk of cardiovascular disease events was 5-8 times higher for individuals with HbA1c>7% as compared to those with HbA1c<5%, Another study showed a progressive increase in risk of kidney disease as HbA1c went from <6% to >8%. Accordingly, in some embodiments, patients with HbA1c levels ≤6.5% or ≤6% are selected for treatment. While the methods are generally discussed in reference to human patients adaptation to non-human mammals is not beyond the scope of the disclosure or the abilities of one of skill in the related arts.

Determination of Individual Dosage

Insulin-FDKP is a dry powder formulation for inhalation provided in cartridges containing a premeasured amount of powder which are inserted into an inhaler. The insulin is administered by inhaling through the inhaler to deliver the powder into the lungs. Cartridges containing different doses can be provided and an individual dosage can be obtained either by using a single cartridge containing the desired dosage or by using multiple cartridges (one at a time).

The patient can be a diabetic with inadequately controlled hyperglycemia, for example with HbA1c greater than 7%, or one with adequately controlled blood glucose levels but desiring to take advantage of other advantages obtainable with ultrarapid acting insulin (for example, weight loss or avoidance of weight gain, reduced risk of hypoglycemia, reduced glucose excursions, etc.).

Determination of individual dosage starts with identification of the daily meal (that is breakfast, lunch, dinner, regularly occurring snack, etc.) resulting in the highest 2-hour post-prandial blood glucose levels using 7 point SMBG (serum measured blood glucose). One then titrates up the dosage for that meal. Once an appropriate dosage is established for that meal the dosage for the daily meal leading to the next highest blood glucose level is titrated, and so on until dosages for all daily meals have been determined. In one embodiment the initial dosage is taken with the untitrated meals. In an alternative embodiment the titration for all daily meals is carried our concurrently rather than sequentially. Meals for which dose titration is being carried out are preferably "usual" for the patient in terms of size and food component content with little variation in these parameters.

Titration begins by taking one low-dose cartridge with the meal(s) in question. Low dose insulin-FDKP cartridges can provide an emitted dose of, for example, 6 or 12 U of insulin. Most commonly the titration is carried out with 12 U cartridges but patients with smaller body masses, with lesser degrees of hyperglycemia to control, and/or lower degrees of insulin resistance may prefer to start the titration at a lower dose and/or proceed through the titration in smaller increments. For clarity the titration is described below with respect to the 12 U dose but it should be understood that the titration could similarly be based on a 6 U or other low-dose cartridge. Similarly even if titrating based on a cartridge that is not the lowest dose available one can use a smaller dose low-dose cartridge to provide the last increment (or decrease) in dosage as an alternative to the procedure described below.

One uses the initial dosage for a week. In each subsequent week the dosage for the meal is increased by the dose of the low-dose cartridge (i.e. 12 U) until a titration endpoint is reached. In various embodiments, the titration endpoint or endpoints can be 1) the post-prandial median blood glucose measured at a point from about 90 minutes to about 2 hours after beginning the meal is between 110 and 160 mg/dl, or 2) the pre-meal/pre-bedtime median blood glucose is 70 and 110 mg/dl or 3) the dosage, based on emitted dose, is 72 U, or 4) an episode of hypoglycemia occurs. For episodes of mild to moderate hypoglycemia with confirmed SMBG of <70 mg/dl decrease dosage by one low dose (i.e. 12 U) cartridge and hold at that dose for one week then resume the titration. For an episode of severe hypoglycemia with confirmed SMBG<36 mg/dl decrease dosage by one low dose (i.e. 12 U) cartridge, hold at this new dose, and begin titration for next meal Generally with a URAI, a titration endpoint based on 90-120 minute blood glucose measurements will be preferred to one based on pre-meal based measurements. In some embodiments the third criteria above for terminating dose escalation specifies a higher terminal dose or the criteria is not used at all. In further embodiments, the dosage can be increased when the 90-minute to 2 hour post-prandial median blood glucose is greater than 140, 160, or 180 mg/dl (that is the titration endpoint is <110, <140, <160, or <180 mg/dl). The particular median blood glucose value used in a titration can be based on the aggressiveness with which a physician determines it is appropriate to treat an individual patient. Factors such as being otherwise in good health, long life expectancy, willingness and ability to comply with the intended treatment regimen weigh in favor of more aggressive treatment while their opposites weigh in favor of less aggressive treatment.

In an alternative embodiment the initial dosage can be estimated based on relative bioavailability from the dosage of a subcutaneously administered insulin. This becomes important in adapting the titration scheme to other formulations and inhaler systems than that used in the examples below. A more universal scale is obtained by identifying dosage according to the insulin exposure (that is the AUC of blood insulin concentration over time). As the titration is described above 12 U emitted corresponds to 3-4 subcutaneous equivalent units (subQ eq). Thus in various embodiments the low dose can be, for example, about 1, 1.5, 2, 3, 4, or 5 subQ eq units. The limit for dose escalation can be about 18, 24, 32 or more subQ eq units.

The expression of dose in subQ eq units also facilitates migration to use of an ultrarapid acting insulin if the patient is already on an insulin regimen. If the patient is already on a prandial insulin regimen they should start with the same subQ eq dose as they are currently using which is then titrated up or down from there basically as described above. If the patient is on a regimen with longer acting insulin alone or a mixture of short and longer acting insulins then 50% of the total daily dose should be divided by the number of daily meals and that amount of ultrarapid acting insulin in sub/Q eq units should be used as the initial dose in the titration. In the case in which the ultrarapid acting insulin is provided in form that does not allow an exact match to the current dosage one can round down or round to the nearest (that is up or down) dose of the ultrarapid acting insulin to use as the initial dose. In one embodiment this choice is left to the practitioner, but particular embodiments specify one or the other choice.

Accordingly, provided herein is a method of determining an individual's dosage of insulin-FDKP for a daily meal comprising the step of administering an initial dosage equivalent to one low-dose cartridge with the meal each day for a week. In each subsequent week the dosage is increased by the amount of one low-dose cartridge until a titration endpoint is reached wherein the titration is selected for the group of 1) achieving a 90-minute to 2-hour post-prandial median glucose is between 110 and 160 mg/dl 70, 2) the dosage based on emitted dose is 72 U, 3) an episode of severe hypoglycemia with a confirmed SMBG<36 mg/dl occurs and the dosage is decreased by the equivalent of one low-dose cartridge, and 4) an episode of mild to moderate hypoglycemia with a confirmed SMBG of <70 (or alternatively 80) mg/dl occurs, the dosage is decreased by the equivalent of one low-dose cartridge for one week and then the titration is resumed until it reaches one of the other endpoints or the dosage is set at the level below that which produces the mild to moderate hypoglycemia. As described above some embodiments do not use a maximum dosage as a titration endpoint or use a different dosage as the maximum.

Embodiments disclosed herein comprise a method in which the dosage for each daily meal is determined as described above for each of the daily meals in succession. This embodiment comprises determining which daily meal results in the highest 2-hour postprandial blood glucose level and titrating that meal first. In some embodiments this determination utilizes a 7 point SMBG. The daily meal resulting in the next highest 2-hour postprandial blood glucose level is then titrated in turn. The initial dosage is administered with each meal not being titrated for with a dosage has not been determined. In alternative embodiments dosages for all daily meals are titrated concurrently.

In one embodiment the low-dose cartridge provides an emitted dose of 3-4 subQ eq units of insulin. In another embodiment the low-dose cartridge provides an emitted dose of 1.5-2 subQ eq units of insulin. In yet another embodiment the low-dose cartridge provides and emitted dose of 2.5 subQ eq units of insulin. In some embodiments the group of titration endpoints further comprises a premeal blood glucose level between 70 mg/dl (or alternatively 80 mg/dl) and 110 mg/dl.

In various alternative embodiments the titration is based on at least three consecutive daily measurements as opposed to being carried out daily over a week as described above, or in a further alternative 3-6 daily measurements over the course of a week. In other alternative embodiments the titration is based on preprandial/pre-bedtime SMBG instead of 90-minute to 2 hour postprandial SMBG. That is the pre-lunch measurement is used to determine the breakfast dose, the pre-dinner measurement is used to determine the lunch dose, and the pre-bedtime measurement is used to determine the dinner dose.

Use of a Standard Dose

Traditional prandial insulin treatment has involved careful adjustment of insulin dosage to the expected glycemic load of the individual meal based on its size and content. The need for this can be avoided, or at least reduced through the use of an ultrarapid acting insulin formulation. Traditional prandial insulin formulations, whether administered by subcutaneous injection/infusion or by inhalation, exert their effect on blood glucose level largely by elevating the glucose elimination rate over a relatively extended period of time. The total glucose elimination brought about is generally proportional to the dose administered. In contrast ultrarapid acting insulin formulations exert their effect over a relatively constrained period of time and a greater proportion of their effect on blood glucose level is the result of rapidly reducing hepatic glucose release to basal levels. The rapid rise of blood insulin level obtained with ultrarapid insulins potentiates a rapid rise in glucose elimination activity and also provide a signal to the liver to reduce glucose release. However the high concentrations of insulin achieved to bring about these effects exceed the range in which glucose elimination rate (GER) is proportional to insulin concentration. Thus while further increasing insulin dosage does lengthen the period of time over which GER is elevated this is brought about by increasing the period of time in which the insulin concentration exceeds the range in which GER is proportional to insulin concentration. Therefore total glucose elimination with ultrarapid acting insulins is much less sensitive to dose. Moreover insulin concentrations return to baseline levels sooner after administration so the effect is also constrained in time and homeostatic mechanisms reassert themselves much sooner than with the relatively longer acting traditional short-acting formulations, thereby reducing the potential for late postprandial hypoglycemia due to the activity of the exogenous insulin.

As a result it can be feasible to set a standard dosage for each of the daily meals and use that dose without regard for variation in caloric content or glycemic load from meal to meal. Because so much of the blood glucose lowering effect is related to reduction of hepatic glucose release, effective reduction is achieved without careful matching of dosage to glycemic or caloric load even if a larger meal than usual is consumed. Because the elevation of GER is comparatively short-lived and generally well-matched in time to the period during which a meal will increase blood glucose levels there is a low risk of hypoglycemia even if a smaller meal is consumed. Nonetheless in preferred embodiments the caloric content and/or glycemic load of the meal is maintained within a range of from 25, 50, or 75% to 125, 150, 200 or 250%, of that of the usual meal (used in determining the standard dose). Since insulin resistance, and therefore responsiveness to insulin, does vary with circadian cycle it will generally be preferred to set a standard dose for each daily meal, though as a practical matter the standard dosage determined may be the same for different daily meals. This method can be particularly well-suited to diabetics with significant residual ability to produce insulin and regulate blood glucose levels, such as type 2 diabetics earlier in the progression of the disease.

Accordingly, provided herein are methods for treating diabetes with standardized doses that are not adjusted based on individual meal content. The method comprises prandial administration of a predetermined standard dosage of an ultrarapid acting insulin formulation without adjustment of the dosage based on meal content. In various embodiments any or all daily meals are treated according to this method; that is for example breakfast, or breakfast and lunch, or breakfast and dinner, or breakfast, lunch, and dinner, etc. In some embodiments a single predetermined dosage is used for all meals. Preferred embodiments utilize predetermined dosages for each daily meal; that is for example, for breakfast, for lunch, for dinner, etc. In some embodiments meal content is assessed as caloric content. In other embodiments meal content is assessed as glycemic load. In preferred embodiments meal content is maintained within a range of from 25, 50, or 75% to 125, 150, 200 or 250% of a usual meal used in determining the predetermined insulin dosage.

In one embodiment the ultrarapid acting insulin formulation is insulin-FDKP. In another embodiment the administration is by inhalation into the lungs.

Use of Split, Supplemental, and Delayed Dosages

With traditional prandial insulin regimens a dosage is selected based on an expectation of how much food will be consumed and then an attempt is made to conform consumption to the advance expectation. If more food is consumed, or its proportion of carbohydrate, fiber, and fat differs from usual or anticipated, it is not possible to improve glycemic control by administering a secondary dose subsequent to the meal when these factors are known with greater certainty, because of the delay between administration and onset of action with traditional formulations. In contrast ultrarapid acting insulin formulations take effect so quickly it can be advantageous to adjust the dosage of insulin to the meal by administering a secondary dose subsequent to the meal. Use of split dosages can be particularly well-suited to diabetics other than type 2 diabetics with good endogenous insulin production and only moderate insulin resistance, for example type 1 diabetics (past the "honeymoon" stage of the disease) and type 2 diabetics later in the progression of the disease In one application of this mode of administration split dosage is applied to meals in which delayed absorption is expected. The delay can be due to disease state—long-term diabetes is associated with delayed nutrient absorption; or can be due to meal content—higher fat and fiber content tend to delay food absorption. Use of split dosages can also be advantageously used in conjunction with multi-course or other prolonged meals such as at holiday celebrations and banquets. Even if the individual limits total consumption in accordance with their usual meals the fact that consumption extends over a longer than usual period of time will also lead to a prolongation of nutrient absorption. Split doses provide a way to address this prolonged profile of nutrient absorption. As compared to the dosage of insulin that would be used with the meal as a single dose one-half to three-quarters, for example two thirds, of the dose is administered at the beginning of the meal and the remainder of the dosage is administered 30 to 120 minutes later.

Accordingly, additional embodiments provide a method of treating diabetes comprising selecting a patient expected to have delayed nutrient absorption, administering an initial dose of ½ to ¾ of a predetermined dosage of an ultrarapid acting insulin formulation at the beginning of a meal, and administering the remainder of the predetermined dosage 30-120 minutes later. In one embodiment, the initial dose is ⅔ of the predetermined dosage. In some embodiments delayed adsorption is related to a state of the disease (diabetes). In other embodiments delayed adsorption is related to meal content. In further aspects of these embodiments meal content comprises high fiber content. In other aspects of these embodiments meal content comprises high fat content. In a further aspect the high fat content constitutes ≥25% of the meal content. In a further aspect the high fat content constitutes ≥35% of the meal content. In one embodiment the ultrarapid acting insulin formulation is insulin-FDKP. In another embodiment the administration is by inhalation into the lungs.

In further embodiments, split dosing is used to control pre-meal (that is, any or all of pre-lunch, pre-dinner, or pre-bedtime) blood glucose that is higher than desired. For example, some patients may find that, even though their blood glucose appears adequately controlled when checked at a point 90 to 120 minutes after beginning a meal (for example, it is <180 mg/dl, <160 mg/dl, <150 mg/dl, <140 mg/dl, <120 mg/dl, or <110 mg/dl, as may be variously advised by their physician), their following pre-meal blood glucose level is regularly greater than desired or targeted, for example greater than 100 mg/dl, 110 mg/dl, 120 mg/dl, 130 mg/dl, or 140 mg/dl. In certain embodiments, the pre-meal period can refer to, for example, up to 30 minutes prior to beginning the meal or going to sleep, or the like.

In such circumstances it may not be recommended or safe to further increase the mealtime dosage. In such cases a second dose can be routinely taken 90-150 minutes, 60-150 minutes or 30-150 minutes after beginning the meal preceding the mealtime(s) or bedtime(s) at which higher than targeted pre-meal blood glucose levels were observed. For example, if the patient's pre-lunch blood glucose level is greater than 100 mg/dl, that patient can be administered a second, supplemental insulin dose 90-150 minutes after beginning their breakfast meal. Thus, higher than targeted pre-meal blood glucose levels for a following meal can be controlled by administering an initial and second dose at the prior meal. In embodiments the insulin doses can comprise an ultrarapid acting insulin formulation comprising for example human insulin and FDKP. These embodiments are distinct from the split dosing methods described above in that the above methods entail the administration of an ultrarapid acting insulin formulation in a postprandial period for immediate correction of post prandially elevated blood glucose on the basis of a currently observed or expected elevation of blood glucose whereas these embodiments entail the regular administration of an ultrarapid acting insulin formulation in a postprandial period for the subsequent correction of anticipated pre-meal blood glucose levels that are higher than targeted prior to the immediately following meal on the basis of an observed pattern of higher than targeted pre-next-meal blood glucose despite adequate control in the preceding post prandial period.

In preferred embodiments a pre-meal blood glucose level that is regularly greater than desired corresponds to higher than targeted pre-meal blood glucose that is observed upon repeated measurement, for example, on three consecutive days for the pre-meal measurement(s) at issue, although other schedules of observation can also be acceptable. For example, in embodiments "regularly greater than desired" (or "regularly higher than targeted") can comprise a pre-meal blood glucose level greater than 100 mg/dl in a majority of the pre-meal periods in a given time interval, such as three, four, five, six, seven, or 10 consecutive days. Similarly, in embodiments "regularly greater than desired" (or "regularly higher than targeted") can comprise a pre-meal blood glucose level of greater than 100 mg/dl in a majority of the pre-meal periods within a given time interval, but not less than 3 pre-meal blood glucose tests in 10 days. Generally, pre-meal blood glucose substantially below the targeted level should not be observed among these pre-meal blood glucose tests and observations of hypoglycemia mixed with higher than targeted blood glucose levels can indicate that a regular supplemental dose is not appropriate.

In another aspect of these embodiments the higher than targeted pre-meal blood glucose is regularly associated with a particular type of meal, for example meals high in fat or high in fiber or large or prolonged meals (such as meals eaten in restaurants or at festive occasions. In such cases the supplemental dose is taken routinely following such meals.

In embodiments the regularly higher than targeted pre-meal blood glucose is related to a disease state. In such cases the supplemental dose is taken routinely following meals prior to the observed period of higher than targeted pre-meal blood glucose.

Therefore, embodiments disclosed herein can comprise administering to a patient with regularly higher than targeted pre-meal blood glucose levels an initial dose of an ultrarapid acting insulin formulation at mealtime, and administering a second, supplemental dose of the ultrarapid acting insulin formulation 30-150, 60-150, or 90-150 minutes after beginning the meal preceding the mealtime(s) or bedtime(s) at which higher than targeted pre-meal blood glucose levels were observed, if pre-meal blood glucose is regularly greater than desired.

Further embodiments can include a method of treating hyperglycemia comprising administering a secondary dose of an ultra rapid acting insulin formulation 30 to 120 minutes after a mealtime dose comprising between 10% to 100% of an initial dose, wherein the secondary dose is titrated so that median blood glucose 1 to 2 hours after the secondary dose is less than 180 mg/dl, or <160 mg/dl, <150 mg/dl, <140 mg/dl, <120 mg/dl, or <110 mg/dl, as may be variously advised by their physician.

In various aspects of these embodiments concerning split, supplemental, or delayed doses or an ultrarapid acting insulin formulation, blood glucose measurements can be obtained using standard 7-point blood glucose monitoring, continuous blood glucose monitoring, or testing in the interval between a single pair of meals. As higher than targeted pre-meal blood glucose levels in the context of prandial insulin treatment will generally be moderate in comparison to untreated postprandial elevations, dosages from the lower end of an available dosage range can be effective in controlling these higher than targeted pre-meal blood glucose levels. In some embodiments the dosage is ≤3 or ≤4 or ≤6 or ≤8 subQ eq units. However, as with insulin generally, body size and degree of insulin resistance can influence effective dosage. Thus, the dosage of the second dose can be 10% to 100% or 25% to 100% of the dosage of the initial dose. In some embodiments the dosage is titrated. In various aspects of these embodiments it is titrated so that the pre-meal median blood glucose level is less than 90 mg/dl, 100 mg/dl, 110 mg/dl, 120 mg/dl, or 140 mg/dl. In further aspects the pre-meal median blood glucose level is not less than 70 or not less than 80 mg/dl. In some embodiments once regularity of occurrence and an advantageous dose is established the intensive testing of blood glucose needed to establish the routine is discontinued. Periodic testing to check the continuing suitability of the routine is appropriate, as with all diabetes treatments.

Secondary doses can also be used to avoid the limiting effect on glucose elimination that can occur at higher doses. URAI quickly induces a maximal rate of glucose elimination. While increasing dosage will extend the time during which insulin concentration is at or above that needed to support maximal glucose elimination rates, as the amount of insulin in a single administration is increased an ever increasing proportion contributes to raising insulin concentration beyond the point where further increase in insulin concentration can effect glucose elimination rates. For this reason, at higher single administration dosages glucose elimination becomes noticeably non-proportional to URAI dosage. This can be noticed in practice by physician and patient in increased dosage producing a less than expected effect on blood glucose levels. The dosage at which the phenomenon becomes problematic will vary from patient to patient based on factors such as body size and degree of insulin resistance; the greater these are the greater dosages that can be used before the effect becomes noticeable. Therefore once this effect emerges, rather than further increasing the mealtime dosage, a secondary dose should be administered routinely 30 to 120 minutes after the mealtime dose. The dosage of the second dose can be 10% to 100% or 25% to 100% of the dosage of the initial dose. In some embodiments the dosage is titrated. In various aspects of these embodiments it is titrated so that the median blood glucose 1 to 2 hours after the second dose is less than 180 mg/dl, 160 mg/dl, 140 mg/dl, 120 mg/dl, or 110 mg/dl or so that the pre-meal median blood glucose level is less than 90 mg/dl, 110 mg/dl, 120 mg/dl, or 140 mg/dl. In further aspects median blood glucose 1 to 2 hours after the second dose is not less than 70 or not less than 80 mg/dl. In some embodiments once an advantageous dose is established the intensive testing of blood glucose needed to establish the routine is discontinued. Periodic testing to check the continuing suitability of the routine is appropriate, as with all diabetes treatments.

In another application of this mode of administration, split dosage is used to adjust the insulin dosage to the actual glycemic load. An initial dose is administered at the beginning of the meal, blood glucose level is determined 60 to 120 minutes later, and a secondary or supplemental dose is administered if blood glucose exceeds 140 mg/dl. In some embodiments the secondary dosage is equal to 50-100% of the initial dosage. In some embodiments blood glucose is determined by continuous glucose monitoring.

Accordingly, additional embodiments provide a method of treating diabetes comprising administering an initial dose of an ultrarapid acting insulin formulation at the beginning of a meal, determining a blood glucose level 60-120 minutes after beginning the meal, and if the blood glucose level exceeds 140 mg/dl (or alternatively 150 mg/dl, 160 mg/dl or 180 mg/dl) administering a second dose of the ultrarapid acting insulin formulation wherein the dosage of the second dose is 25% to 100% or 50% to100% of the dosage of the initial dose. In one embodiment the ultrarapid acting insulin formulation is insulin-FDKP. In another embodiment the administration is by inhalation into the lungs.

In a variation on this mode of administration no dose is administered at the initiation of the meal. Instead administration is delayed for example until 10, 15, 20, or 30 minutes after beginning the meal. This variation is particularly suitable when delayed nutrient absorption is expected.

Accordingly, embodiments disclosed herein provide a method of treating diabetes comprising administering a dose of an ultrarapid acting insulin formulation subsequent to the beginning of a meal to a patient expecting delayed nutrient absorption. In one embodiment delayed absorption is due to higher fat and fiber content as compared to a usual meal as used in determining dosage. In another embodiment delayed absorption is due to long standing diabetes. In one embodiment the ultrarapid acting insulin formulation is insulin-FDKP. In another embodiment the administration is by inhalation into the lungs.

Treatment of Patients of with Subcutaneous Insulin Resistance

Many of the advantages of insulin-FDKP are related to its ultrarapid kinetics. However insulin-FDKP is typically administered by inhalation of a dry powder preparation. There is a class of patients who can receive an additional benefit from this formulation due to its route of administration, namely patients with subcutaneous insulin resistance. This phenomenon is distinct from and unrelated to the insulin resistance typically associated with type 2 diabetes, which is generally understood to result from a reduced responsiveness of cells throughout the body to insulin.

The phenomenon of subcutaneous insulin resistance is not universally accepted by experts in diabetes as a bona fide physiological state. Certainly its etiology is not well understood and indeed there may be multiple factors that can lead to this condition. Nonetheless experience with inhalable insulin has demonstrated the clinical reality of this phenomenon. There are patients who have required substantially greater doses of insulin than might otherwise be expected when treated with subcutaneously administered insulin who upon switching to a pulmonary insulin require an amount of insulin more in line with what would be expected based on their medical condition. Subcutaneous insulin resistance can also contribute to difficulty in establishing reasonable control of hyperglycemia and in variability in the response to insulin.

To prospectively identify diabetes patients having subcutaneous insulin resistance several factors can be considered. First of all the patient will be using high doses of insulin, especially compared to what would typically be required based on their medical condition including body weight and state of progression of the disease. For example a high dose of insulin is one greater than 2 units/Kg/day. This criterion can further be paired with the patient having normal or near-normal basal levels of endogenous serum insulin, for example 50 pU/ml of insulin. Such patients typically will have type 2 diabetes in an early stage in the progression of the disease. Alternatively high insulin usage can be paired with lipoatrophy or lipodystrophy as diagnostic criteria.

In yet other alternative embodiments high insulin usage can be paired with very poorly controlled hyperglycemia as the selection criteria. Very poorly controlled hyperglycemia can be evidenced by three HbA1c level determinations ≥9% in a 12 month period despite treatment with an intensified insulin regimen, for example basal-bolus therapy, or continuous subcutaneous insulin infusion (CSII; that is, an insulin pump), etc., over a period ≥6 months. Commonly HbA1c levels are determined quarterly. It is preferred that the three HbA1c level determinations ≥9% be consecutive. In alternative embodiments very poorly controlled hyperglycemia can be evidenced by two HbA1c level determinations ≥9% in a 6-9 month period.

In still further alternative embodiments high insulin usage can be paired with life threatening glycemic instability as the criteria for selection. Life threatening glycemic instability can be characterized by periods of hyperglycemia and/or hypoglycemia despite adherence to diet, exercise, and insulin regimens.

Accordingly embodiments herein provide methods of treating diabetics with subcutaneous insulin resistance. These methods include a step for the selection of patients with subcutaneous insulin resistance on the basis of atypically high insulin dosage. In some embodiments the insulin dosage is ≥2 units/Kg/day. In some embodiments the selection is further based on the patient having normal or near-normal levels of endogenous insulin. In some of these patients the basal level endogenous insulin is ≥50 µU/ml. In other embodiments the selection is further based on the patient being on an intensified insulin regimen and having three HbA1c level determinations ≥9% in a 12 month period. In still other embodiments the selection is further based on the patient having life threatening glycemic instability characterized by periods of hyperglycemia and/or hypoglycemia despite adherence to their insulin regimen and any diet or exercise regimen.

These methods also include a step of discontinuing treatment with subcutaneously administered rapid-, short-, or intermediate-acting insulin formulations. Note that patients who cannot produce sufficient insulin to meet basal requirements need to continue taking basal insulin even if it is administered subcutaneously. Presently the only basal (long-acting) insulin formulations commercially available are for subcutaneous administration. However other long acting insulins are being developed which could potentially be administered by other routes of administration and their use in the methods herein is contemplated. These methods also include the step of (initiating) treatment by administration of prandial doses of insulin-FDKP by inhalation.

Further embodiments can include a step for confirming the diagnosis of subcutaneous insulin resistance by determining that a similar or improved degree of glycemic control is achieved with a substantially lower dosage of insulin. In some embodiments glycemic control is assessed as HbA1c level. In other embodiments it is assessed as post-prandial and/or fasting blood glucose levels. In various embodiments the insulin dosage (exclusive of any basal requirement) is reduced by ≥10, ≥20, or ≥50%, or more. In some embodiments the reduced dosage is assessed from measurements of serum insulin levels. In other embodiments it is based on the dosage used and the relative bioavailability of the insulin formulations.

Combined use of Ultrarapid Acting Insulin and Long Acting Insulin Analogs

One mode of use of ultrarapid acting insulin is to use it in combination with a long acting insulin in a basal-bolus regimen. In basal-bolus therapy a long acting insulin is used to provide or supplement a basal level of insulin and a bolus of short acting insulin is administered in conjunction with meals to handle the resultant increased glucose load. The various advantageous characteristics of ultrarapid acting insulin make it an ideal choice for use as the short acting insulin in such regimens.

Many long acting insulins are administered twice a day, but insulin glargine (sold as LANTUS® by Sanofi-Aventis) is approved and marketed for once a day administration. According to the manufacturer's prescribing information (March 2007 revision) insulin glargine provides relatively constant glucose lowering activity over a 24-hour period and may be administered any time during the day provided it is administered at the same time every day. Additionally, insulin detemir (sold as LEVEMIR® by Novo Nordisk) is approved and marketed for administration either twice a day or once a day with the evening meal or at bedtime (manufacturer's prescribing information, Version 3 issued May 16, 2007).

In clinical trials it was found that an ultrarapid acting insulin formulation comprising insulin-FDKP used in combination with insulin glargine was effective in managing glucose excursions. In 7 point glucose measurements insulin-FDKP was able to flatten the jagged pattern resulting from post-prandial glucose excursions, but over the course of the day baseline blood glucose levels tended to rise. Similar behavior was observed in type 1 (See Example 2 and FIG. 12) and type 2 diabetics (see FIG. 13). There are several factors that may contribute to this rise. Insulin resistance tends to rise over the course of the day. Additionally the insulin glargine used in the study was administered in the evening before bedtime as contemplated in the manufacturer's prescribing information. Thus the greatest demand for insulin activity is occurring late in the period of effectiveness of the insulin glargine dose when it is weakening.

In typical combinations insulin glargine is used in combination with either a prandial short acting insulin or mixes of short and intermediate acting insulins administered before breakfast and dinner. Intermediate acting insulins are intended to provide glucose lowering activity for both meal and between-meal periods. Even the marketed short acting insulins exert the majority of their activity after most of a meal's nutrients have been absorbed. Thus in commonly used regimens involving combinations of insulin glargine and shorter acting insulins, the other insulins provide supplementary activity during waking hours. In contrast insulin-FDKP has a short duration of action, well matched to the time period in which a meal produces an increased glucose load, but not providing substantial insulin activity for baseline control. Thus when combined with an ultrarapid acting insulin such as insulin-FDKP any insufficiency of insulin glargine dose or duration will be exacerbated as compared to established regimens. Insulin detemir has a shorter duration of action than insulin glargine so that when used once a day such deficiencies should be even more pronounced. To remediate such effects regimens combining the use of ultrarapid acting insulins and a long acting insulin analog should specify that the long acting insulin analog be administered early in waking hours, for example at breakfast time or within 1, 2, 3 or 4 hours of waking. In some embodiments an early dose of the long acting insulin analog is the only dose given in the course of the day. In other embodiments the long acting insulin analog is insulin glargine and it is administered twice a day, an early dose and a late dose approximately 8 to 14, preferably 10-12, hours later, for example around dinnertime. A typical cycle of sleeping and waking, in which a person sleeps for an extended period, usually at night, and then wakes and becomes active for the remainder of a day, naps notwithstanding, is assumed. Thus phrases such as within a certain time after waking, early in waking hours, and similar terminology refer to the point at which a subject wakes and initiates their daily activities.

Combined use of Ultrarapid Acting Insulin and Basal Insulin Provided by Infusion Insulin pumps are compact devices that deliver various forms of insulin at appropriate times to help control the blood glucose level. Used correctly, these devices improve blood glucose control with fewer hypoglycemic episodes and better long-term control. The pumps are programmable and give patients a degree of freedom to vary what, when or how much they eat by allowing insulin delivery rates to be adjusted for different times of day. The latest models of insulin pumps are relatively easy to use and convenient to carry. These newer pumps have built-in dosage calculators that manage the complex insulin dosage calculations previously performed by patients. Patients are able to program bolus doses to coincide with a meal as well as different basal insulin delivery rates for different times of day, depending on changing needs. These pumps also calculate how much insulin is still working from the previous bolus dose. Some pumps have additional smart features such as programmable reminders and alerts, information and download capabilities that allow the patient to save information to a computer for accurate record-keeping, a carbohydrate database for calculating the amount of carbohydrate ingested in a meal, and certain safety features.

As an alternative to subcutaneous bolus injection of long acting insulin it is also possible to provide basal insulin by continuous infusion. This approach obviates the need for long acting insulin since insulin is continually provided. This approach can also avoid any drawbacks associated with such preparations, for example increased immunogenicity or binding to receptors for insulin-like growth factors that can occur with analogs. As the rate of infusion can be changed throughout the day with this approach, the profile of basal insulin activity can be more readily adjusted to variations in diet and individual physiology. (The capabilities of insulin pumps are more fully discussed in the section dealing with artificial pancreas systems, below). A common methodology with insulin pumps is to aim to cover both prandial and basal needs by using one of the rapid acting analogs. When the pump is only being used to provide basal insulin—as with a prandial non-pumped ultrarapid acting insulin—regular human insulin can be used. However for patients with less stable basal need the more rapid kinetics of the rapid acting analogs can offer an advantage.

Accordingly embodiments provide a method of treating diabetes comprising infusing insulin with an insulin pump to meet basal insulin needs and administering an ultrarapid acting insulin to meet prandial needs. In some embodiments the pumped insulin is regular human insulin. In other embodiments the pumped insulin is a rapid acting insulin analog. In one embodiment the ultrarapid acting insulin formulation is insulin-FDKP. In another embodiment the administration of the ultrarapid acting insulin is by inhalation into the lungs.

Use of Ultrarapid Acting Insulin in Combination with or in Place of Oral Antidiabetic Medications Standard of care in the treatment of type 2 diabetes is defined and regularly updated in consensus statements published jointly by the American Diabetes Association and the European Association for the Study of Diabetes. The general course of treatment advocated, summarized below, has remained fairly stable in recent years (compare for example Nathan et al. *Diabetes Care* 29: 1963-1972, 2006; Nathan et al. *Diabetes Care* 31: 173-175, 2008; and Nathan et al. *Diabetes Care* 32: 193-203, 2009) with the most significant change in the most recent update being the addition of GLP-1 agonists to the treatment algorithm.

The course of treatment as advocated in these consensus statements begins with lifestyle changes plus the drug metformin at diagnosis (Step 1). Lifestyle changes include improved diet and increased exercise. Metformin is a drug classified as a biguanide. Although historically these drugs have been described as insulin sensitizers, there primary effect is to reduce hepatic glucose output. This activity appears to be dependent on the presence of insulin and metformin treatment can be associated with somewhat increased sensitivity to insulin. However avoided herein is applying the term "insulin sensitizer" to the biguanides as the mechanism of action is different from that of the thiazolidinediones which are now more commonly intended by the term and for which the primary effect to increase insulin sensitivity. As metformin is present throughout the day its effect is observed as a reduction in fasting blood glucose levels (FBG). Approximately 30% of patients cannot tolerate metformin, at least at dosages adequate for acceptable glycemic control, with gastrointestinal side-effects being a primary issue. The prescribing information (January 2009 revision) for metformin (sold as GLUCOPHAGE® by Bristol-Myers Squibb) includes contraindications for use in patients with renal disease or dysfunction, hypersensitivity to the drug, or metabolic acidosis, as well as other precautions.

If adequate glycemic control is not attained (generally HbA1c remains ≥7%) with Step 1 treatment Step 2 treatment calls for the addition of a second agent. This can be basal insulin, a sulfonylurea, pioglitazone, or a GLP-1 agonist. If the two agents (the second agent not being basal insulin) still do not establish adequate glycemic control the consensus calls for either switching the second agent to basal insulin, our using a combination of a sulfonylurea and pioglitazone as the second agent. If the combination of a sulfonylurea and pioglitazone still does establish adequate glycemic control the consensus calls for switching the second agent to basal insulin. By any of these paths the consensus advocates that the first insulin regimen used be basal insulin.

The sulfonylureas are insulin secretagogues, that is, they enhance insulin secretion. Included in this class are the drugs chlorpropamide, glyburide, gliclazide, glimepiride and glipizide. A major issue with these agents is an increased risk of hypoglycemia, especially great with chlorpropamide and glyburide. Use of these agents has also been implicated in increased mortality from cardiovascular disease. Weight gain is common with these agents. Contraindications, precautions, and drug interactions typical of the sulfonylureas can be found in the prescribing information for glipizide (sold as GLUCOTROL® by Pfizer; September 2006 revision). Concern has also been raised that insulin secretagogues increase demand on an already overtaxed pancreas contributing to the progressive decrease in β-cell function and limiting their long term usefulness. Other insulin secretagogues are known such as the glinides, for example repaglinide and nateglinide. The risk of weight gain with these agents is similar to the sulfonylureas, but the risk of hypoglycemia may not be as elevated. GLP-1 agonists and DPP-4 (dipeptidyl peptidase-4) inhibitors can also be considered insulin secretagogues. As used, insulin secretagogues provide their activity throughout the day so that their effect is readily seen as a reduction in FBG.

Pioglitazone (sold as ACTOS® by Takeda Pharmaceuticals) is a thiazolidinedione (glitazone, TZD) which increase the sensitivity of muscle, fat, and liver to insulin thereby counteracting the insulin resistance aspect of type 2 diabetes, and are therefore commonly referred to as insulin sensitizers. TZDs have been associated with fluid retention and congestive heart failure and also with increased rates of bone fracture, especially in women with osteoporosis. The TZDs also include the drug rosiglitazone (sold as AVANDIA® by GlaxoSmithKline) which has been further associated with myocardial ischemia. These and other side-effects, precautions, etc., such as weight gain are reporting in the manufacturer's prescribing information for ACTOS® (August 2008 version) and AVANDIA® (October 2008 version).

The third (and last) step in the consensus algorithm is reached if—or when as type 2 diabetes is a progressive disease—adequate glycemic control is not attained by treatment including basal insulin under the second step. The third step advocates that the lifestyle changes and metformin treatment of the previous stages be continued along with intensified insulin treatment. As described intensified treatment can include prandial use of rapid acting insulin analogs, but definitely involves the continued use of basal insulin.

Patient populations treated according to the embodiments herein disclosed are distinct from those most commonly receiving insulin therapies. Indeed the factors that might impel a clinician to prescribe insulin to individuals according to current paradigms do not shed any light on the relative effectiveness of an ultrarapid acting insulin as compared to oral antidiabetic agents especially given the distinct pharmacokinetic profiles of the insulin preparations available. Moreover, as seen above use of insulin typically begins with basal insulin, with prandial insulins being added only after the failure of basal insulin alone. In contrast the methods disclosed herein involve use of prandial ultrarapid acting insulin early in the progression of treatment.

Patients with early stage insulin disorders can be divided into various subpopulations and treated according to various embodiments of the present invention. Some persons make sufficient insulin to maintain a non-hyperglycemic fasting blood glucose level but cannot avoid acute fluctuations in blood glucose after eating. Early type 2 diabetics can often use diet and exercise to control even substantial hyperglycemia, but will have already lost their early phase insulin release. In current practice patients failing diet and exercise are most often next treated with a suppressor of hepatic glucose output, such as metformin, with the goal of overcoming insulin resistance and improving the effectiveness of the insulin that is produced. In embodiments disclosed herein, these patients are administered a prandial, early phase-mimicking insulin preparation instead of, or in addition to, the insulin sensitizer. Less often (and previously) the first oral medication offered diabetics was an insulin secretagogue, such as a sulfonylurea, to increase insulin secretion. More commonly (and currently) such agents are used in combination with a suppressor of hepatic glucose output as a subsequent step in treatment if use of the sensitizer alone does not provide the desired level of glycemic control. However, use of secretagogues can also lead to weight gain and hypoglycemic events so, in a one embodiment, a prandial, early phase-mimicking insulin preparation is used instead of a secretagogue in such combination treatments.

Both fasting and postprandial blood glucose levels contribute to elevation of HbA1c levels. Ultrarapid acting insulin preparations can advantageously impact both fasting and postprandial blood glucose levels. It was initially appreciated that they are particularly well suited to addressing control of postprandial blood glucose in contrast with basal insulins or insulin secretagogues, or even short acting insulins. This is understood to be due in part to their more rapid suppression of endogenous glucose production (see Example 1). Thus embodiments disclosed herein are directed to patients with poorly controlled postprandial blood glucose or in whom the lack of glycemic control is more strongly associated with elevated postprandial blood glucose. For example patients with a lesser degree of insulin resistance may be able to produce sufficient insulin to provide substantial control of fasting blood glucose and in some embodiments can be selected for treatment with ultrarapid insulin alone. In comparison patients with a higher degree of insulin resistance may have poor control of both fasting and postprandial blood glucose and in embodiments would be selected for treatment with ultrarapid insulin and an oral antidiabetic agent in combination.

Ultrarapid Acting Insulin and Suppressors of Hepatic Glucose Output

Both ultrarapid acting insulin and biguanide drugs such as metformin act as suppressors of hepatic glucose release. However as used the drugs exert their effect around the clock whereas prandial ultrarapid acting insulin exerts this effect more particularly following meals. Thus ultrarapid acting insulin can substitute for or augment the activity of the oral suppressors of hepatic glucose output.

Accordingly in one embodiment ultrarapid acting insulin is used in treating a subject with type 2 diabetes in need of improved glycemic control with well or moderately controlled FBG but poorly controlled PPG. In various aspects of the embodiment need for improved glycemic control is determined as HbA1c level, 1- or 2-hour PPG, or oxidative stress. In some embodiments well controlled FBG is FBG≤110 or ≤130 mg/dL. In some embodiment moderately controlled FBG is FBG≤154 mg/dL, ≤180, or ≤192 mg/dL. Studies have determined that at HbA1c levels ≤8.4% at least half of overall hyperglycemia is due to PPG (Monnier, L. et al. *Diabetes Care* 26: 881-885, 2003). Thus in some embodiments a subject with well or moderately controlled FBG but poorly controlled PPG is a subject with HbA1c≤8.4%. (An HbA1c of 8.4% corresponds to a mean plasma glucose level of approximately 192-198 mg/dL; see *Diabetes Care* 32, suppl. 1: Sβ-S61, 2009, especially tables 8 and 9). In various embodiments a subject with poorly controlled PPG in one with 1- or 2-hour PPG≥140, or ≥180, or ≥200 mg/dL. It should be noted that subjects whose 2-hour PPG following a 75 g glucose challenge was ≥200 mg/dL had an almost doubled risk of mortality than those whose 2-hour PPG was <200 mg/dL regardless of their FPG (Lancet 354: 617-621, 1999). In one embodiment the subject is not currently receiving any drug treatment and ultrarapid insulin is used as the sole pharmacologic agent. In another embodiment the subject is undergoing treatment with an oral suppressors of hepatic glucose output and prandial ultrarapid insulin is added to their treatment regimen. In one embodiment the oral suppressors of hepatic glucose output is metformin. In one embodiment the ultrarapid acting insulin formulation is insulin-FDKP. In another embodiment the administration of the ultrarapid acting insulin is by inhalation into the lungs.

In other embodiments, a subject with type 2 diabetes in need of improved glycemic control could benefit from treatment with a suppressor of hepatic glucose output, but such oral agents are contraindicated or not tolerated, and ultrarapid acting insulin is used instead. In a variation the oral agent is not tolerated in sufficient dosage and ultrarapid acting insulin is used to supplement its activity.

Ultrarapid Acting Insulin and Insulin Secretagogues

Insulin secretagogues such as the sulfonylureas and the glinides increase insulin secretion and thereby insulin concentrations in circulation. Ultrarapid acting insulin preparations also increase insulin concentrations in circulation. However as used the drugs exert their effect around the clock whereas prandial ultrarapid acting insulin exerts this effect more particularly following meals. Thus ultrarapid acting insulin can substitute for the activity of the insulin secretagogue. In one embodiment the ultrarapid acting insulin formulation is insulin-FDKP. In another embodiment the administration of the ultrarapid acting insulin is by inhalation into the lungs.

Accordingly in one embodiment, a patient under treatment with a suppressor of hepatic glucose output and an insulin secretagogue discontinues treatment with the secretagogue and institutes treatment with an ultrarapid acting insulin. In a related embodiment a patient under treatment with a suppressor of hepatic glucose output who is a candidate for treatment with an insulin secretagogue and instead institutes treatment with an ultrarapid acting insulin rather than with a secretagogue. In one embodiment the patient is in need of improved glycemic control. In various aspects of the embodiment need for improved glycemic control is determined as HbA1c level, 1- or 2-hour PPG, or oxidative stress.

In other embodiments a subject with type 2 diabetes could benefit from treatment with an insulin secretogogue, but such oral agents are contraindicated or not tolerated, and ultrarapid acting insulin is used instead. In other embodiments the patient is in need of reducing the risk of hypoglycemia or weight gain.

Ultrarapid Acting Insulin and Insulin Sensitizers

Insulin sensitizers, such as pioglitazone and the other TZDs improve insulin utilization in various tissues thereby reducing insulin resistance and leading to a reduction in circulating insulin levels. Treatment with TZDs results in notable decreases in FBG. Treatment with prandial ultrarapid acting insulin leads to a reduction in FBG. This is despite the fact that there is no direct glucose eliminating activity due to prandial ultrarapid acting insulin during fasting periods. The impact of ultrarapid acting insulin preparations on fasting blood glucose levels was unexpected and suggests that they can reduce insulin resistance or act as an insulin sensitizer. Interestingly the rapid insulin concentration peak obtained with ultrarapid acting potentiates subsequent insulin activity. This is particularly noticeable in type 2 diabetics in the time frame immediately following administration however the effect may be longer lived. Thus treatment with prandial ultrarapid acting insulin has effects similar to insulin sensitizers.

Accordingly, in some embodiments, patients are selected for treatment comprising an ultrarapid acting insulin on the basis of having a high degree of insulin resistance. In other embodiments patients who would benefit from treatment with an insulin sensitizer, such as a TZD, but have a sensitivity to the drug or are otherwise contra-indicated, are treated with an ultrarapid acting insulin in place of the drug. For example TZDs can be contraindicated in women with osteoporesis.

Patients who can benefit from treatment with prandial ultrarapid acting insulin according to various embodiments include those who obtain inadequate glycemic control with an insulin sensitizer and would otherwise have an insulin secretagogue added to their treatment regimen, or those who obtain inadequate glycemic control with a combination of an insulin sensitizer and an insulin secretagogue. Subsets of these groups include those who further are needle-phobic or would otherwise want to avoid injections, and those who further are obese, overweight, or otherwise desire to avoid or minimize weight gain or need to lose weight. Additionally elevated insulin levels are associated with a greater occurrence of breast cancer. Thus persons with an elevated risk of breast cancer can particularly benefit from a lowering of insulin resistance. In one embodiment the ultrarapid-acting insulin formulation is insulin-FDKP. In another embodiment the administration of the ultrarapid acting insulin is by inhalation into the lungs.

Prandial Ultrarapid Insulin Versus Basal Insulin

When treatment with two oral medications does not provide adequate glycemic control standard of care offers paths to the use of basal insulin or use of a third oral medication. The choice to add a third oral medication instead of adding insulin is often influenced by reticence to accept daily injections even in the absence of an outright needle phobia, the risk of hypoglycemia, and the likelihood of weight gain. Thus embodiments of the invention provide a successor treatment to combination oral therapy that includes insulin, but is needle-free and minimizes or eliminates weight gain. The inhalable insulin EXUBERA®, because of its subcutaneously delivered insulin-like kinetics, would not be expected to confer the same benefits as an ultrarapid acting insulin preparation. This use shows that prandial ultrarapid insulin offers a unique alternative to the early use of basal insulin generally, and that offers particular advantage to patient populations in which needle use, the risk of hypoglycemia, or the prospect of weight gain are particularly problematic.

Patients who can benefit from treatment according to various embodiments disclosed herein include those who obtain inadequate glycemic control with an oral suppressors of hepatic glucose output and would otherwise have an insulin secretagogue added to their treatment regimen, or those who obtain inadequate glycemic control with a combination of an oral suppressor of hepatic glucose output and an insulin secretagogue. Subsets of these groups include those who further are needle-phobic or would otherwise want to avoid injections, and those who further are obese, overweight, or otherwise desire to avoid weight gain or need to lose weight.

EXAMPLES

Example 1

The experiments were conducted to identify the effect of an ultrarapid acting insulin, specifically a formuslation for inhalation comprising insulin-FDKP, when compared to subcutaneously administered insulin lispro (lispro, HUMALOG®, Eli Lilly & Co.) and an inhaled recombinant human insulin (EXUBERA®, Pfizer Inc.) on endogenous glucose production after a meal challenge and during a euglycemic glucose clamp procedure in subjects with type 2 diabetes. The insulin-FDKP formulation is administered to the subjects by oral inhalation using a MEDTONE® dry powder inhaler (MannKind Corp.).

Following the completion of the meal challenge, the data was analyzed as per the statistical analysis plan. Total insulin exposure was found to be approximately 40% greater following the administration of 12 U lispro than following either 45 U insulin-FDKP (TI) or 4 mg EXUBERA®. Hence, the study was redesigned, and subjects did not proceed to the euglycemic glucose clamp portion of the study under the original protocol and treatments (4 mg EXUBERA®, 45 U TI and 12 U lispro). The study was amended (A1) and included 12 subjects (10 were reenrolled from the first meal challenge), and only two treatments, which were 10 U lispro and 60 and 90 U TI. The doses were selected based on the relative bioavailability observed following the first meal challenge (OP), where under an assumption of linear kinetics, 10 U lispro and 60 U TI would result in similar exposure. The 90 U dose group was included to assess the effect of the highest dose group of TI studied in Phase 3 trials. Six of the 12 subjects received 60 U TI and the other 6 subjects received 90 U TI. All 12 subjects received 10 U lispro in a crossover fashion.

Methods and results below are described in terms of the Original Protocol (OP), which includes the meal challenge in 18 subjects with three treatments (EXUBERA®, lispro and TI) and Amendment 1 (A1), which includes 12 subjects treated with only TI and lispro.

Subjects with insulin-treated type 2 diabetes participated in the study. The subjects were screened and evaluated before, during and after the experiments and their data analyzed as described below. Subjects were selected based on several key inclusion criteria, including, male and female, having ≥18 and ≥70 years of age with clinical diagnosis of type 2 diabetes mellitus for ≥12 months. The subjects selected for the study also had stable anti-diabetic regimen with insulin for the previous 3 months; HbA1c≤8.5%; Body Mass Index (BMI) between ≤34 kg/m² and ≥25 kg/m²; urine cotinine ≤100 ng/mL; PFTs of FEV1≥70% of predicted value, single breath CO diffusing capacity (DLco uncorrected)≥70% of predicted. Subjects had also been treated with oral antidiabetic medication within the previous 3 months; total daily insulin requirement of 1.2 IU/kg body weight. Criteria for exclusion from the study also included unstable diabetes control and/or evidence of serious complications of diabetes (e.g., autonomic neuropathy); serum creatinine >1.8 mg/dL in female subjects and >2.0 mg/dL in male subjects. Other clinically important pulmonary disease was confirmed by documented history or pulmonary function testing.

Under OP, the study was planned to be a randomized, open label, 3-way cross-over study. The visits comprised an initial screening visit, 3 sequential treatment visits for the meal challenge test followed by a minimum 8-week (up to a maximum of 12 weeks) blood-loss recovery period, an interim safety visit, 3 sequential visits for the glucose clamp procedure, and a final close-out visit. At this analysis all patients at least had completed the meal challenge visits and only those data have been used. The screening visit(s) (V1) occurred 1 to 21 days before the first treatment visit (V2) with 7 to 21 days elapsing between treatment-visits (V2, V3, and V4) for the meal challenge test. A minimum of 8 weeks elapsed between V4 and the next treatment visit, (V6). An additional safety visit (V5) was scheduled 1-3 days prior to the first of 3 glucose clamp procedures (V6). The glucose clamp procedure occurred at 3 visits, Visits V6, V7, and V8, with 7 to 21 days elapsing between the visits. A final visit (V9) occurred 2 to 10 days after V8, to assess physical examination such as body weight and height.

Under A1, the study was planned to be a randomized, open label, 2-way cross-over study. The visits comprised an initial screening visit, 2 sequential treatment visits for the meal challenge test followed by a minimum 4-week (up to a maximum of 12 weeks) blood-loss recovery period, an interim safety visit, 2 sequential visits for the glucose clamp procedure, and a final close-out visit. The screening visit(s) (V1) occurred 1 to 21 days before the first treatment visit (V2) with 7 to 21 days elapsing between treatment-visits (V2 and V3) for the meal challenge test. A minimum of 4 weeks elapsed between V3 and the next treatment visit, (V5). An additional safety visit (V4) was scheduled 1-3 days prior to the first of 3 glucose clamp procedures (V5). The glucose clamp procedure occurred at 2 visits, Visits V5 and V7, with 7 to 21 days elapsing between the visits. A final visit (V8) occurred 2 to 10 days after V7, to assess physical examination such as body weight and height.

Each treatment visit during the meal challenge had the subjects hospitalized in the clinical unit the night before initiation of treatment. At the first treatment visit (V2) for the meal challenge test, subjects were randomly allocated to a treatment order for insulin-FDKP, insulin Lispro or EXUBERA® (OP) and insulin-FDKP and lispro (A1) based on a cross-over design. Each subject followed the same randomization order for the glucose-clamp procedures as for the meal challenge tests.

During the study, periodic blood draws for determination of pharmacokinetic and/or pharmacodynamic parameters, and safety were taken beginning at 12 hours prior to onset of the treatment regimens and meal challenge, and thereafter for a period of 8 hours. Screening testing and all 3 meal challenge tests required in combination a total of 409.5 mL of blood for analysis and evaluation of the treatments (OP) and 279 mL blood for A1. The glucose clamp procedure visits, final visit, and the interim safety visit required a total of 514.2 mL of blood (OP) and 365 mL blood for A1 for the analysis and evaluation of the treatments. The total blood voulume needed for A1 studies was 644 mL per subject. Radiolabeled $D_2$-glucose infusion was administered to subjects 12 hours prior to onset of the meal challenge and insulin treatment.

Meal Challenge Test: BOOST PLUS® (12 fl. oz.) consisting of 67.5 g carbohydrate, 21 g protein, 21 g fat, energy content 540 kcal was used for the meal challenge test. The BOOST PLUS® was enriched with U-$^{13}$C-glucose to determine the amount of absorbed glucose. Concurrent enriched continuous infusion of 6,6-$^2$H$_2$ glucose was used to assess endogenous glucose production EGP. Sampling for fasting EGP (f-EGP) occurred before the start of an intravenous insulin lispro infusion, i.e., at the end of a 7-hour period of enriched infusion of 6,6-$^2$H$_2$ glucose under OP. In A1, the continuous insulin infusion was conducted using either insulin lispro (for subjects treated with TI) or regular human insulin (for subjects treated with lispro). Baseline blood glucose concentrations of 90 mg/dL (OP) and 110 mg/dL (A1) were established and maintained by variable infusion of insulin and 20% glucose enriched with 6,6-$^2$H$_2$ glucose over a period of at least 5 hours prior to dosing with insulin-FDKP, insulin lispro, or EXUBERA® (OP) or insulin-FDKP and lispro under A1. Insulin Lispro infusion rate (OP) and lispro or RHI infusion rate (A1) was fixed at the lowest possible level 90 minutes prior to treatment dose. Following dosing, blood glucose concentrations were kept from falling below 90 mg/dL (OP) and 75 mg/dL (A1) by a glucose infusion.

Dosing with the test treatments was performed with administration of a dose of 45 U of Insulin-FDKP, 12 U of subcutaneous insulin lispro, or 4 mg of recombinant human insulin (EXUBERA®) administered by oral inhalation at time point 0 (OP), or 10 U subcutaneous lispro and 60 or 90 U TI (A1) immediately prior to BOOST PLUS® ingestion. Under OP, the dose for insulin lispro was selected based on information obtained from the regulatory label. The dose selected for EXUBERA® was obtained by means of back calculation of the most commonly used dose information presented to the FDA Advisory Committee in the EXUBERA® Briefing Document. The insulin-FDKP dose was derived from results in completed phase 2 and 3 clinical studies carried out by MannKind Corporation, the assignee of the application. Under A1, the doses were calculated based on insulin exposure observed under OP. Blood glucose concentrations were measured at regular intervals from arterialized venous blood samples. The amount of orally absorbed glucose was estimated by determination of U-$^{13}$C-glucose. EGP was determined by measurement of 6,6-$^2$H$_2$ glucose applying the modified calculations for the non-steady state (R. Hovorka, H. Jayatillake, E. Rogatsky, V. Tomuta, T. Hovorka, and D. T. Stein. Calculating glucose fluxes during meal tolerance test: a new computational approach. *Am. J. Physiol Endocrinol. Metab* 293 (2): E610-E619, 2007). C-peptide concentrations were measured pre- and post-dose to assess endogenous insulin secretion. In addition, glucagon and free fatty acid concentrations were also determined.

Glucose-clamp Procedure: An enriched continuous infusion of 6,6-$^2$H$_2$ glucose was used to assess EGP. Blood samples to determine fasting EGP (f-EGP) were taken before the start of an intravenous insulin infusion, i.e., at the end of a 7-hour period of enriched infusion of 6,6-$^2$H$_2$ glucose into the subjects. Baseline blood glucose concentrations of 90 mg/dL (OP) and 110 mg/dL (A1) were established and maintained by variable infusion of insulin and 20% glucose enriched with 6,6-$^2$H$_2$ glucose by means of a Biostator device over a period of at least 4 hours prior to dosing with insulin-FDKP, insulin lispro, or EXUBERA® (OP) and either lispro or TI under A1.

Dosing with the test treatments was performed by administering a dose of 45 U of Insulin-FDKP, 12 U of sc Insulin Lispro, or 4 mg of recombinant human insulin (EXUBERA®) under OP, and lispro or 60 or 90 U of TI (A1) in the same order as for the meal challenge test for each individual subject. EGP was determined for each subject by measuring 6,6-$^2$H$_2$ glucose in the blood samples and applying the modified calculations by Hovorka et al. (ibid) for the non steady-state. Serum C-peptide concentrations were measured pre- and post-dose to assess endogenous insulin secretion. In addition, glucagon and free fatty acid concentrations were determined at regular intervals. All subjects were returned to their prior anti-diabetic treatment regimens at the end of each treatment visit.

Figure 3:
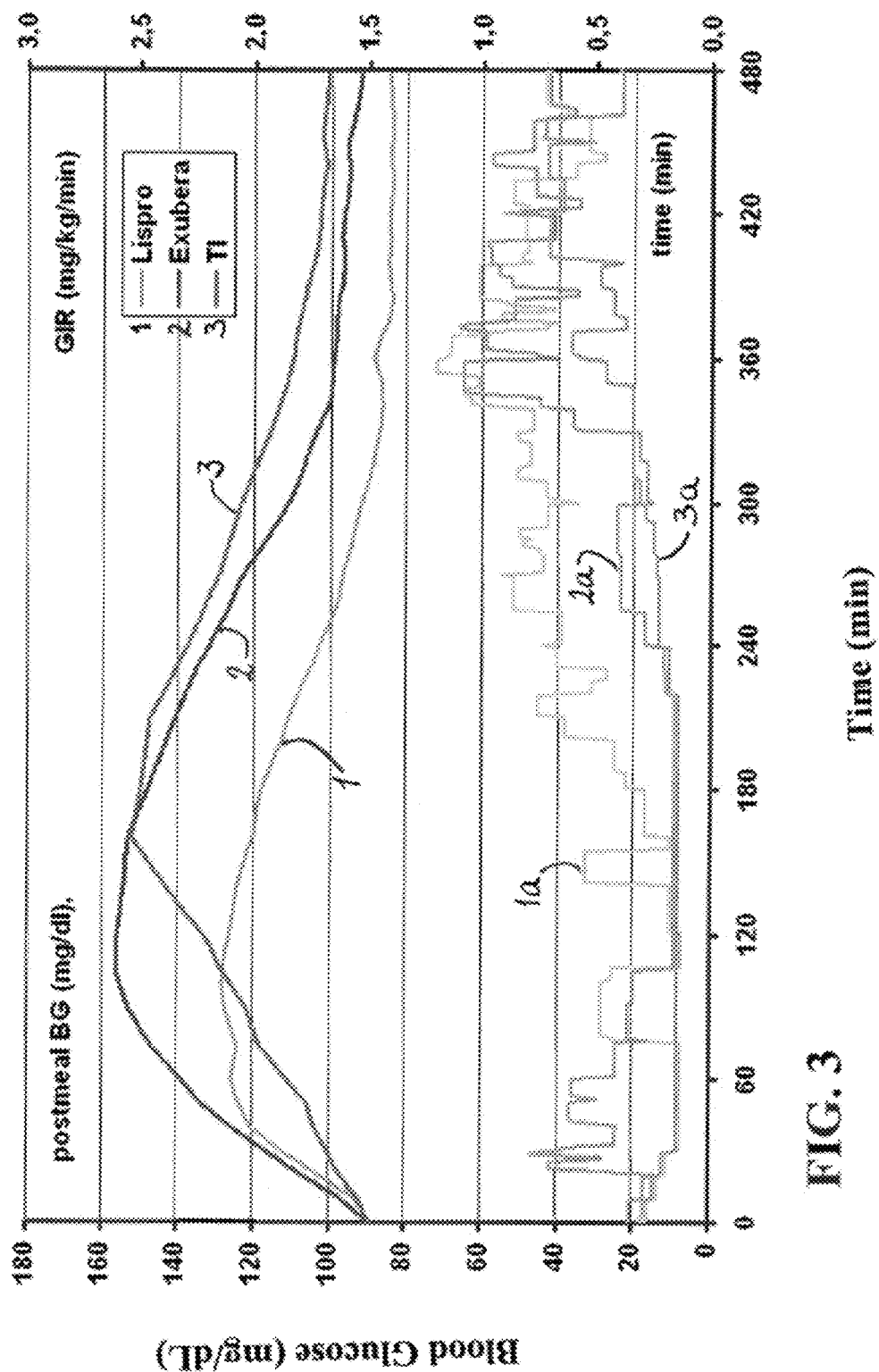
FIG. 3. is a graph of data obtained from a study in which blood glucose concentrations were measured at various times after a meal in patients with type 2 diabetes who were treated with insulin lispro (HUMALOG®, 1), EXUBERA® (2) and an insulin formulation comprising fumaryl diketopiperazine (insulin-FDKP, 3) at the onset of the meal. The graph also shows (line drawings at its bottom) the exogenous glucose infusions administered to the patients as needed to maintain euglycemic levels following administration of each of the treatments and indicated as 1a, 2a and 3a, respectively.

The results of the OP portion of the study are presented in FIGS. 3-6. FIG. 3 is a graphical representation of data plotted from blood sample values obtained from patients in this study. In particular, FIG. 3 shows measured blood glucose concentrations at various times after the meal challenge in patients with type 2 diabetes who were treated with insulin lispro (1), EXUBERA® (2) and an insulin formulation comprising fumaryl diketopiperazine (insulin-FDKP, TI, 3) at the onset of the meal. The time points in the data plots of each treatment curve represent the mean value for all samples analyzed in the study. The graph also shows the exogenous glucose infusions administered to the patients as needed during the experiments to maintain euglycemic (remain above 90 mg/dl of blood glucose) levels following administration of each of the treatments and represented in the graph as 1a, 2a, and 3a, respectively for insulin lispro, EXUBERA® and insulin-FDKP. As seen in FIG. 3, the glucose levels differ for all three treatments. It is evident from the data that the insulin lispro-treated subjects were overdosed due to the need to give the patients repeated glucose infusions to remain above 90 mg/dL. The graph also shows that subjects treated with insulin-FDKP had reduced glucose levels much earlier than the other treatments, with some subjects under this treatment requiring glucose infusions to remain above 90 mg/dL at early stages of the study. However, the insulin-FDKP treated subjects did not require further glucose infusion until about six hours after onset of treatment, which indicate that this treatment was effective at maintaining glycemic control for an extended period of time. The data also show that the glucose concentration was controlled in all subjects by all treatments, however, in subjects treated with insulin-FDKP, glucose control occurred more effectively from onset to about 120 minutes after treatment. Minimal glucose infusions were needed (following the initial phase) until after six hours following insulin-FDKP administration (when glucose demand is likely driven by the baseline insulin infusion) as compared to EXUBERA® and lispro treated subjects who were infused with glucose at about 4 and 3 hours respectively, post-treatment. The data indicate that patients treated with lispro and EXUBERA® may have reached hypoglycemic levels post-dosing if glucose were not infused. Hence, insulin-FDKP may be able to maintain the blood glucose above hypoglycemic levels more efficaciously than the other treatments for a longer period of time.

Figure 4:
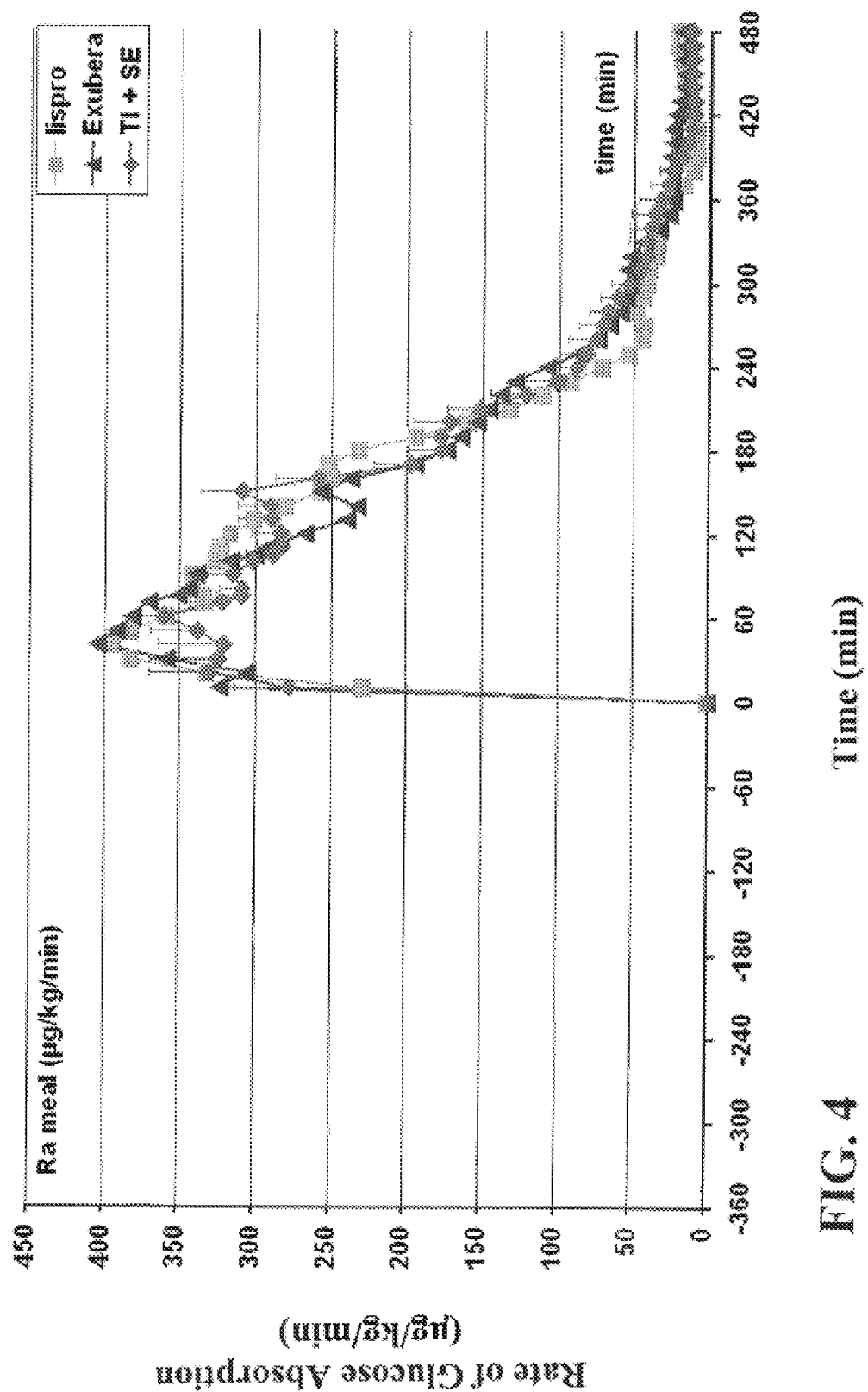
FIG. 4 is a graph of data obtained from a study which measured the rate of absorption of glucose for a period of time after a meal in patients with type 2 diabetes who were treated with insulin lispro, EXUBERA® and an insulin-FDKP formulation at the onset of the meal.

FIG. 4 is a graph of data obtained from the patients in the study described above showing the rate of absorption of glucose for a period of time after a meal in patients with type 2 diabetes who were treated with insulin lispro, EXUBERA® and an insulin-FDKP formulation immediately prior to of the meal. The time points in the data plots of each treatment curve represent the mean value for all samples analyzed in the experiments. The data in FIG. 4 show that the subjects treated with the three treatments all exhibited similar patterns for the rate of glucose absorption from the meal taken. Therefore, the data indicate that the treatment did not alter the rate of glucose absorption in the subjects treated from a meal.

Figure 5:
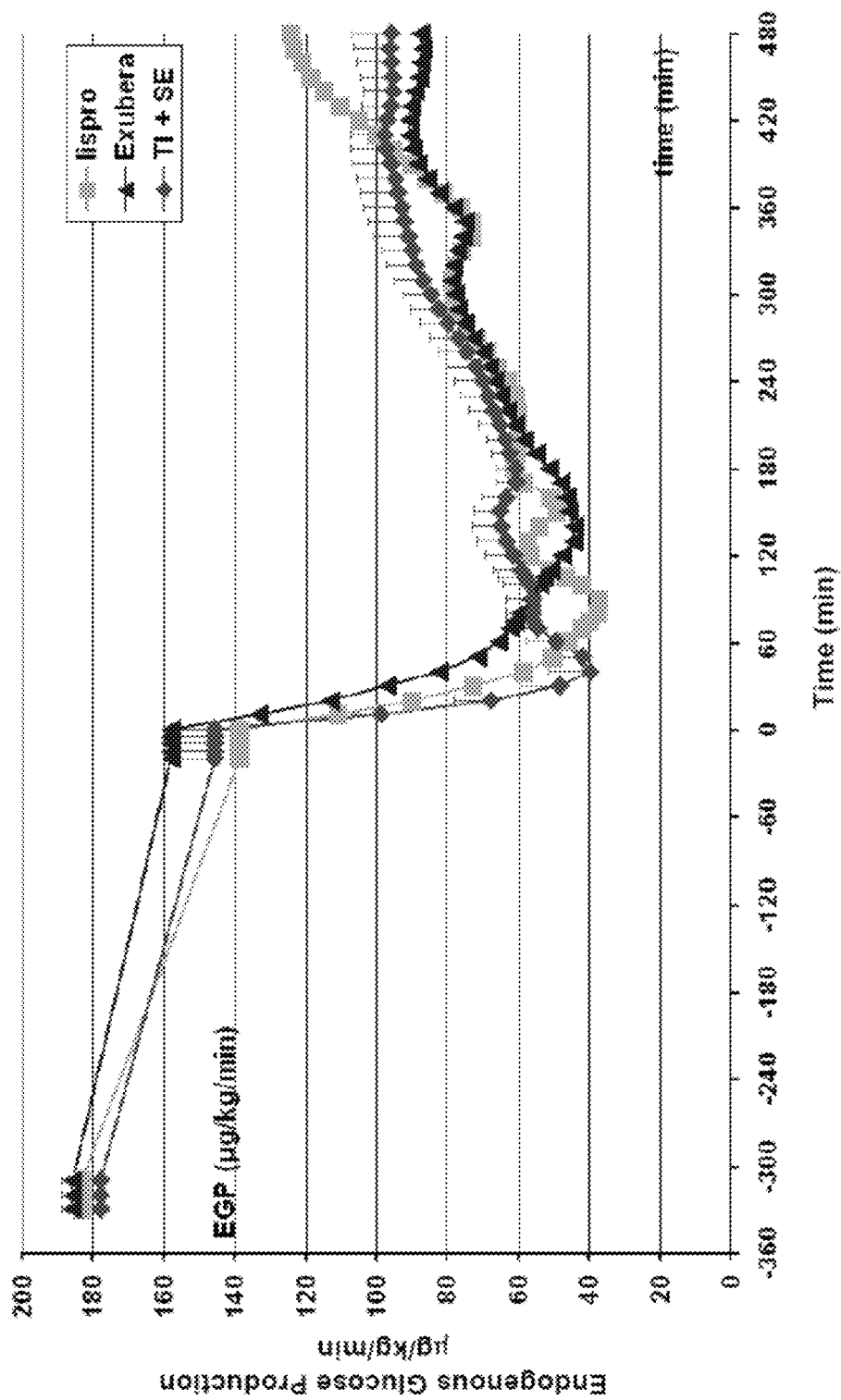
FIG. 5 is a graph of data obtained from a study in which endogenous glucose production after a meal was determined in patients with type 2 diabetes who were treated with insulin lispro, EXUBERA® and an insulin-FDKP formulation at the onset of the meal.

FIG. 5 is a graph of data obtained from experiments in which endogenous glucose production after a meal was determined in patients with type 2 diabetes who were treated with insulin lispro, EXUBERA® and an insulin-FDKP formulation at the onset of the meal. The time points in the data plots in each treatment curve represent the mean value for all samples analyzed in the experiments. The data curves for the three treatments show that all three treatments were effective in inhibiting endogenous glucose production in the treated subjects to a similar degree, suggesting a physiologic maximum for this effect. Notably subjects treated with insulin-FDKP exhibited peak inhibition of endogenous glucose production at a much faster or earlier time (at about 40 minutes) after treatment as compared to insulin lispro (at about 80 minutes) and EXUBERA® (at about 125 minutes).

Figure 6:
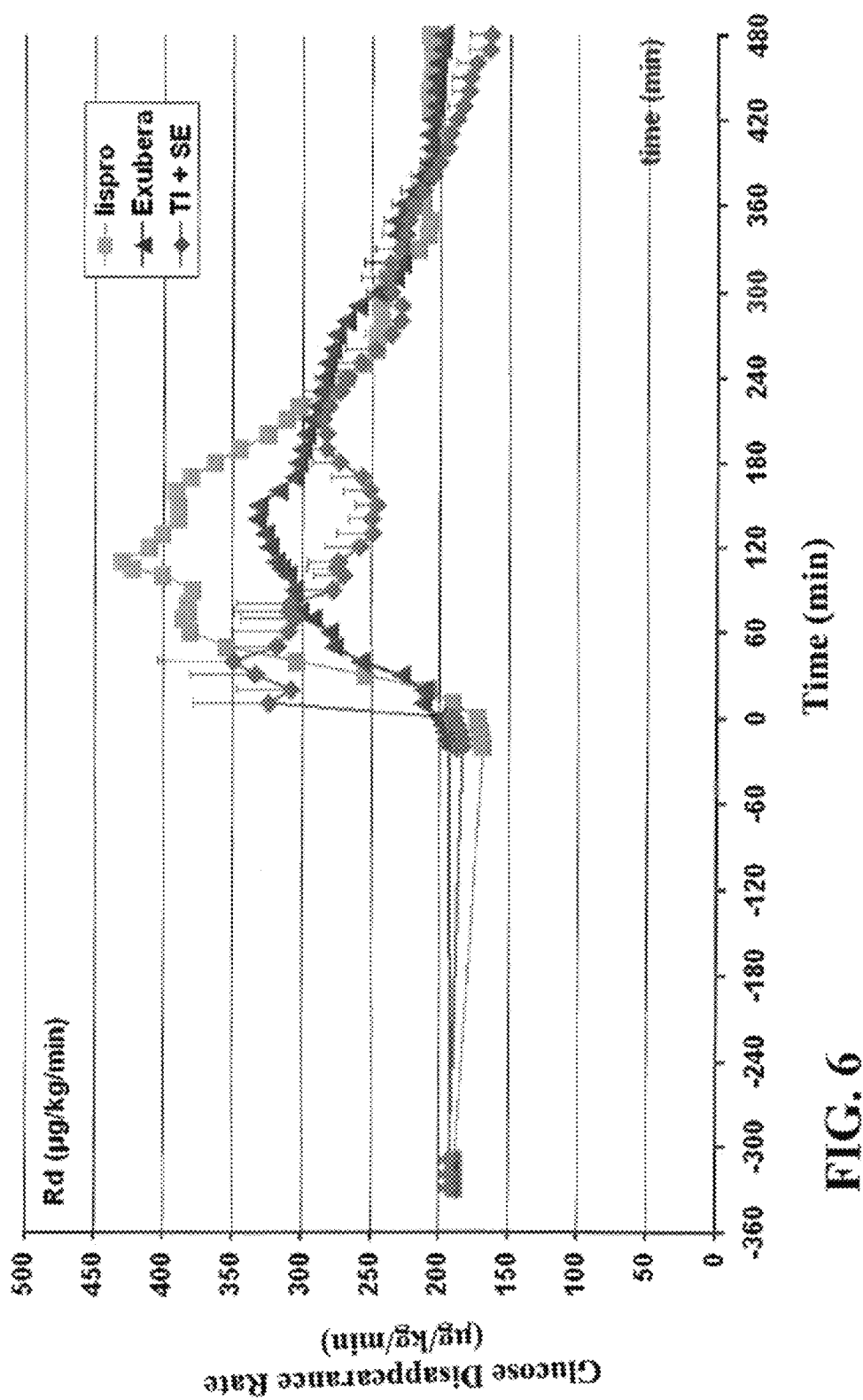
FIG. 6 is a graph of data obtained from a study which monitored for a period of time the rate of glucose disappearance in patients with type 2 diabetes, who were treated with insulin lispro, EXUBERA® and an insulin-FDKP formulation at the onset of the meal.

FIG. 6 is a graph of data obtained from experiments that monitored the rate of glucose disappearance for a period of time in subjects with type 2 diabetes, who were treated with insulin lispro, EXUBERA® and an insulin-FDKP formulation at the onset of the meal as described above. The time points in the data plots for each treatment curve represent the mean value for all samples analyzed in the experiments. In addition, the glucose disappearance rate was standardized to account for each subject's body weight by dividing the rate of glucose disappearance by the body weight of the subject. The data show that the rate of glucose disappearance or utilization for the subjects was different for all treatments. Notably, the glucose disappearance rate for insulin-FDKP was evidently much sooner than for insulin lispro or EXUBERA®. It was substantial at the first measurement after dosing, about 10 minutes post dosing, whereas the glucose disappearance rate for the others did not significantly depart from baseline until about 30 minutes. The glucose disappearance rate for insulin-FDKP peaked at about 40 minutes after dosing, much earlier as compared to insulin lispro (at about 120 minutes) and EXUBERA® (at about 150 minutes).

The study also indicated that measurements of C-peptide (data not shown) clearly show that an increase in C-peptide concentrations was delayed in the TI group when compared to lispro and EXUBERA®. This later increase in C-peptide (and endogenous insulin production), is related to the ability of each of the exogenous insulins to control the glucose absorbed from the meal, and appears to be related to the shape of the insulin profiles for each treatment group. The slow rise in insulin concentrations following EXUBERA® and lispro (median $t_{max}$ of 113 and 75 minutes, respectively, versus a $t_{max}$ of 20 minutes in the TI group, results in a decreased ability to control glucose early following the meal, and therefore, in an earlier increase in the patients' endogenous insulin response. The delay of endogenous insulin production in the TI group, however, indicates better control of blood glucose early in the study, when TI concentrations are high.

In summary, the data from the study indicate that insulin-FDKP was a markedly and surprisingly more efficacious treatment in patient with type 2 diabetes than existing treatments, i.e., insulin lispro and EXUBERA®, in that the insulin-FDKP treatment was faster at inhibiting endogenous glucose production and faster at inducing the glucose disappearance or utilization rate. It is surprising that EXUBERA® is so much slower in these parameters than even insulin lispro, to which it is otherwise kinetically similar. This further emphasizes the non-equivalence of these two inhalable insulin preparations (i.e. insulin-FDKP and EXUBERA®) already evident from their different kinetics.

Figure 7:
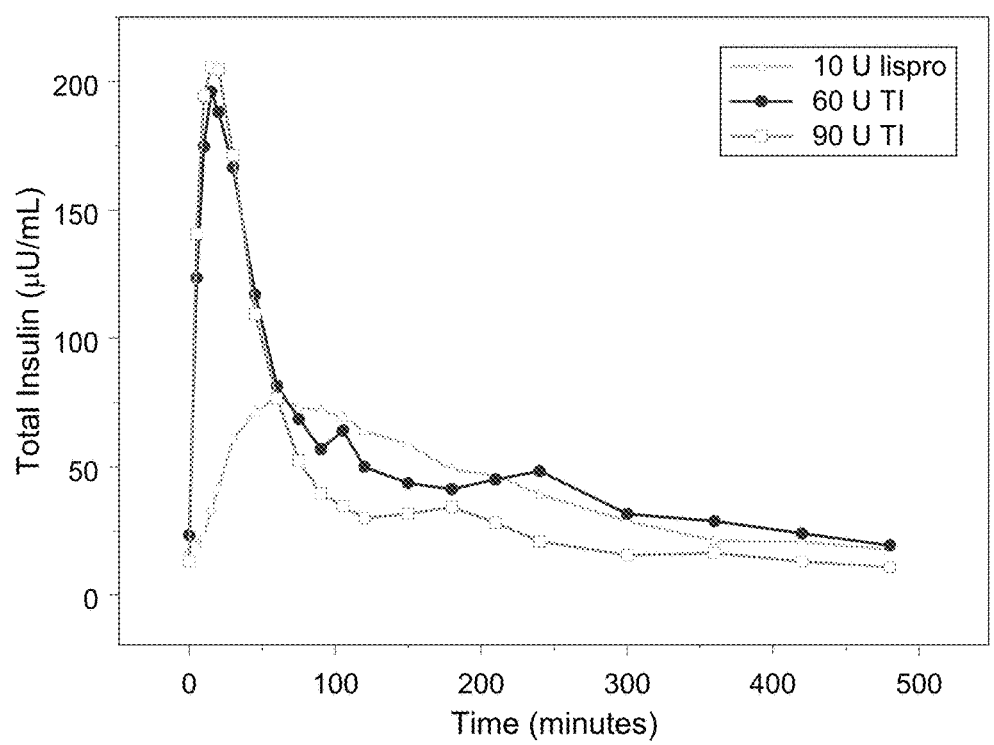
FIG. 7 depicts the mean insulin concentration-time profiles for patients with type 2 diabetes who were treated with insulin lispro nd 60 U or 90 U of an insulin-FDKP formulation at the onset of the meal from the glucose clamp study.

The results of the A1 portion of the study are presented in FIGS. 7-11. FIG. 7 is a graphical representation of data plotted from blood samples values obtained from subjects in this study. In particular, FIG. 7 shows the mean insulin concentration-time profiles for the three treatments. Total insulin concentrations (the sum of regular human insulin and lispro concentrations at each time point) are shown, as all of the insulin in the system is associated with the elicited response. Following both 60 and 90 U of insulin-FDKP administration, observed peak insulin concentrations are much higher (196 and 216 μU/mL following TI versus 83 μU/mL following lispro) and occur much earlier (median $t_{max}$ of 15 and 17.5 minutes following TI versus 60 minutes following lispro) when compared to peak insulin concentrations following lispro treatment. However, average exposure was very similar between the three groups, with total insulin AUC of 24,384, 18,616 and 19,575 pU/mL*min for the two TI dose groups and lispro, respectively.

Figure 8:
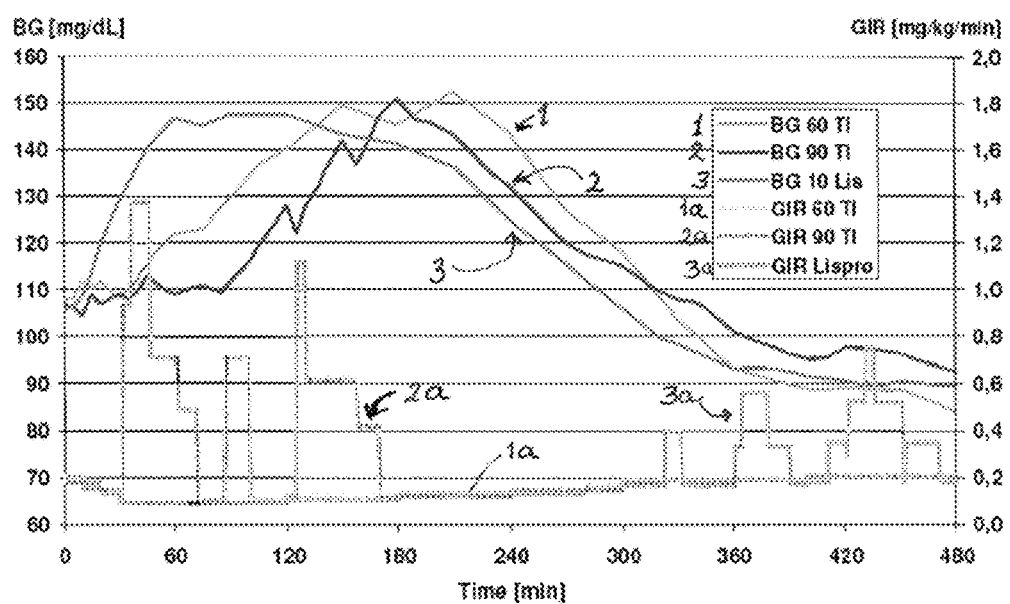
FIG. 8 depicts the blood glucose concentration of patients with type 2 diabetes who were treated with insulin lispro, 3), and 60 U (1) or 90 U (2) of an insulin-FDKP formulation at the onset of the meal from the glucose clamp study. The time of glucose infusion and amount of glucose infused is shown as 1a, 2a, and 3a respectively for 60 U and 90 U of an insulin-FDKP and insulin lispro.

FIG. 8 shows measured blood glucose concentrations at various times after the meal challenge in patients with type 2 diabetes who were treated with either 60 or 90 U of insulin formulation comprising fumaryl diketopiperazine (insulin-FDKP, 2, 3), and insulin lispro (1) at the onset of the meal. The time points in the data plots of each treatment curve represent the mean value for all samples analyzed in the study. The graph also shows the exogenous glucose infusions administered to the patients as needed during the experiments to maintain euglycemic (to remain above 75 mg/dL of blood glucose) levels following administration of each of the treatments and represented in the graph as 1a, 2a, and 3a, respectively for 60 and 90 U of insulin-FDKP, and insulin lispro, respectively. As seen in FIG. 7, the glucose profile shapes differ for all three treatments, however, maximal glucose levels are very similar, and glucose was controlled by all three treatments. The graph also shows that subjects treated with either dose of insulin-FDKP had reduced glucose levels much earlier than following lispro administration, with more efficacious glucose control occurring within the first 120-180 minutes post-dose. Subjects treated with both 90 U insulin-FDKP and lispro required some additional glucose infusions to maintain blood glucose at or above 75 mg/dL. Following 90 U TI, some subjects required additional glucose infusions in the earlier post-dose period, and following lispro, these infusions were needed in the latter period. This phenomenon can be due to the rapid glucose clearance rate observed in the patients treated with 90 U of insulin FDKP. Minimal glucose infusions were needed (following the initial phase) until the end of the study following insulin-FDKP administration (when glucose demand is likely due to the baseline insulin infusion) as compared to lispro treated subjects, who were infused with glucose between 5 and 8 hours post-treatment. This result is indicative of an elevated insulin presence and activity following lispro treatment in a timeframe well beyond expected glucose absorption following a meal. Additionally, it is evident that the 90 U insulin-FDKP group controlled blood glucose levels more efficiently than the group treated with the 60 U dose of insulin-FDKP, resulting in lower blood glucose levels in the 0-180 minute time period. Due to the better control, less endogenous insulin was secreted by the patients receiving the 90 U insulin-FDKP dose, and thus endogenous insulin contributed a small portion of the total insulin profile of the individuals in this group. Moreover, the data indicate that more endogenous insulin contributed to the total insulin profile of the group treated with 60 U dose of insulin-FDKP, making the average insulin profiles similar for the two groups tested.

Figure 9:
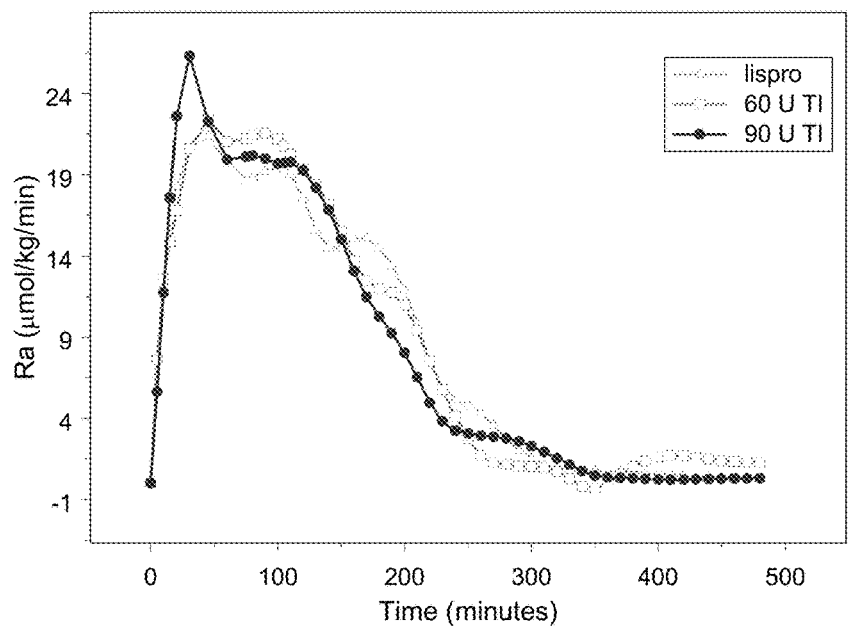
FIG. 9 is a graph of data obtained from a glucose clamp study which shows the rate of glucose absorption in the patients with type 2 diabetes treated with 60 U or 90 U of an insulin-FDKP and insulin lispro immediately prior to the meal.

FIG. 9 is a graph of data obtained from the patients in the study described above showing the rate of absorption of glucose for a period of time after a meal in patients with type 2 diabetes who were treated with 10 U insulin lispro, and 60 and 90 U of an insulin-FDKP formulation immediately prior to the meal. The time points in the data plots of each treatment curve represent the mean value for all samples analyzed in the experiments. The data in FIG. 9 show that the subjects treated with the three treatments all exhibited similar pattern of the rate of glucose absorption from the meal taken. Therefore, the data indicate that the treatment did not alter the rate of glucose absorption in the subjects treated from a meal.

Figure 10:
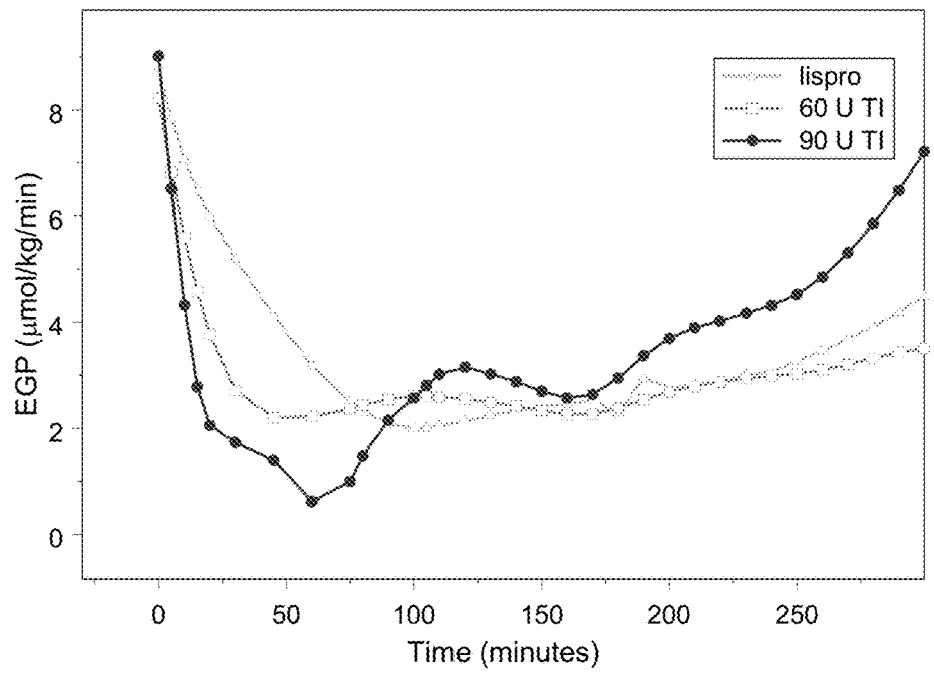
FIG. 10 is a graph of data obtained from a glucose clamp experiments in which endogenous glucose production after a meal was determined in patients with type 2 diabetes treated with 60 U or 90 U of an insulin-FDKP and insulin lispro at the onset of a meal.

FIG. 10 is a graph of data obtained from experiments in which endogenous glucose production after a meal was determined in patients with type 2 diabetes who were treated with 10 U of insulin lispro and either 60 or 90 U of an insulin-FDKP formulation at the onset of the meal. The time points in the data plots in each treatment curve represent the mean value for all samples analyzed in the experiments. Two subjects treated with 90 U insulin-FDKP were excluded from the analysis due to difficulty in interpreting the modeled results. The data curves for the three treatments show that all three treatments were effective in inhibiting endogenous glucose production in the treated subjects, to a similar degree between the 60 U insulin-FDKP and 10 U lispro treatments. The data also indicate that the 90 U insulin-FDKP treatment has a greater and faster effect on inhibiting endogenous glucose production. Notably subjects treated with insulin-FDKP exhibited peak inhibition of endogenous glucose production at a much faster or earlier time (at about 40 and 60 minutes for the two treatments) following dosing, than insulin lispro (at about 100 minutes).

Figure 11:
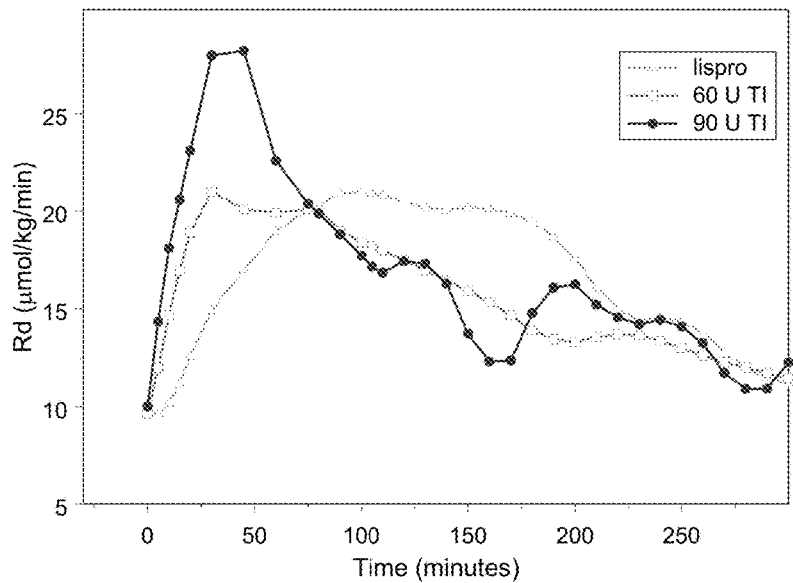
FIG. 11 is a graph of data obtained from experiments that monitored the rate of glucose disappearance for a period of time in subjects with type 2 diabetes treated with 60 U or 90 U of an insulin-FDKP and insulin lispro at the onset of a meal.

FIG. 11 is a graph of data obtained from experiments that monitored the rate of glucose disappearance for a period of time in subjects with type 2 diabetes, who were treated with 10 U of insulin lispro and either 60 or 90 U of an insulin-FDKP formulation at the onset of the meal as described above. The time points in the data plots for each treatment curve represent the mean value for all samples analyzed in the experiments. In addition, the glucose disappearance rate was standardized to account for each subject's body weight by dividing the rate of glucose disappearance by the body weight of the subject. The data show that the rate of glucose disappearance or utilization for the subjects was different for all treatments. Notably, the glucose disappearance rate for both the 60 U and 90 U insulin-FDKP dose groups was evident much earlier than for insulin lispro. The glucose disappearance rate of the insulin-FDKP treated groups was substantial at the first measurement after dosing, about 5 minutes post dosing, and peaked at about 30-50 minutes after dosing, much earlier as compared to insulin lispro (at about 100 minutes).

In summary, the data from the study indicate that insulin-FDKP was markedly a more efficacious treatment in patient with type 2 diabetes than existing treatments, i.e., insulin lispro, in that the insulin-FDKP treatment was faster at inhibiting endogenous glucose production and faster at inducing the glucose disappearance or utilization rate in patients with type 2 diabetes. Insulin-FDKP effect on EGP and glucose utilization appeared to increase with increasing dose.

Example 2

A Prospective, Multi-Center, Open-Label, Randomized, Controlled Clinical Trial Comparing the Efficacy and Safety in Subjects with Type 1 Diabetes Receiving SC Basal Insulin and Prandial Inhalation of Insulin-FDKP Versus SC Basal and Prandial Insulin Over a 52-Week Treatment Period and a 4-Week Follow-up This was a prospective, multi-country, multicenter, open label, randomized, controlled clinical trial comparing glycemic control in subjects with type 1 diabetes receiving basal insulin and prandial insulin-FDKP (TI) Inhalation Powder (TI Inhalation Powder group) with subjects receiving basal insulin and SC rapid-acting insulin aspart (comparator group). This study included a 52-week treatment phase and a 4-week follow-up phase. During the 4-week follow-up phase, pulmonary function and select clinical laboratory assessments were scheduled.

The study began with enrollment at Week-3. Subjects received a complete battery of safety and eligibility assessments, including HbA1c and fasting plasma glucose (FPG).

At Week-1, subjects were randomized to one of the following 2 treatments:
Basal insulin+prandial TI Inhalation Powder
Basal insulin+prandial SC rapid-acting insulin At Week-1, subjects again completed the first three components of the Insulin Treatment Questionnaire (ITQ) for the purpose of assessing test-retest reliability only). After completing the questionnaire, subjects randomized to the TI Inhalation Powder group were trained on the MEDTONE® Inhaler using TECHNOSPHERE®/insulin (insulin-FDKP) inhalation powder; subjects in the comparator group were trained in the use of the NOVOLOG® pens; all subjects were trained in administration of LANTUS®. Additionally, all subjects were trained on a blood glucose monitoring (HBGM) meter provided at the beginning of the trial and diary and received diabetes education. Any training was repeated at Week 0, if needed.

At the beginning of the treatment phase, subjects had several titration/dose evaluation visits to adjust insulin therapy. Titration visits occurred once a week for the first 4 weeks. During Weeks 4 through 10, there were three telephone "visits" (at Week 6, Week 8, and Week 10) to titrate dose, if necessary. However, dose titration was allowed throughout the trial.

All subjects completed a 7-point blood glucose profile on any 3 days during the week immediately preceding each visit from Week 0 to Week 52. The 7 time points included samples from before breakfast and 2 hours after breakfast, before the mid-day meal and 2 hours after the mid-day meal, before the evening meal and 2 hours after the evening meal and at bedtime (7 time points a day, over 3 days). These blood glucose (BG) values were recorded in the HBGM diary that was collected at clinic visits. The diaries for Weeks 4 through 10 (during dose titration) which were discussed over the telephone were collected at the next office visits.

A meal challenge test was performed at Week 4 (during dose titration), Week 26, and Week 52. Meal challenge venous blood sampling times were: −30, 0, 30, 60, 90, 105, 120, 180, 240, 300, and 360 minutes. Blood glucose (BG) was also measured using HBGM glucose meters to aid the Investigator in treatment decisions and values were obtained at −30, 0, 60, and 120 minutes during the meal challenge.

Treatments for glycemic control used in the trial were the following: prandial insulin-FDKP (TI) inhalation powder, prandial insulin aspart, and basal insulin glargine. Subjects assigned to the TI Inhalation Powder group (TI Inhalation Powder in combination with basal insulin therapy) received sc basal insulin glargine (LANTUS®) once daily (at bedtime) and inhaled TI Inhalation Powder 3 to 4 times a day, immediately before main meals or a snack as based upon clinical need. Adjustment of the TI Inhalation Powder dose and frequency of use to greater than 3 times a day was at the discretion of the Investigator. Subjects in the comparator group received SC basal insulin glargine once daily (at bedtime) and SC injection of rapid acting insulin (NOVOLOG®) 3 to 4 times per day, immediately before main meals (no later than 10 minutes before meals).

The primary objective of this trial was to compare the efficacy over 52 weeks of TI Inhalation Powder+basal insulin versus insulin aspart+basal insulin as assessed by change from baseline in HbA1c (%). A total of 565 subjects were studied in sites in the United States, Europe, Russia, and Latin America. A total of 293 subjects received TI Inhalation Powder+basal insulin, and 272 subjects received insulin aspart+basal insulin.

The primary efficacy endpoint was assessed using pre-specified ANCOVA and Mixed Model with Repeated Measures (MMRM) analyses. Due to disproportionate dropouts between the TI Inhalation Powder+basal insulin treatment arm and the insulin aspart+basal insulin treatment arm, the assumption of missing completely at random for the ANCOVA model was violated. As such, the MMRM was used as a secondary confirmation. TI Inhalation Powder met the primary endpoint of non-inferiority in the MMRM model, although not in the ANCOVA model. The mean change from baseline over 52 weeks was comparable in both treatment groups, with a Least Square Means treatment difference of −0.25% in favor of insulin aspart. Based on results from both models, there was not a clinically significant difference between treatment groups in mean change from baseline in HbA1c. Indeed, a comparable percentage of subjects reached HbA1c target levels in the 2 treatment groups. There were no statistically significant differences in the percentage of subjects whose HbA1c level decreased to ≤8.0% (50.99% for the TI Inhalation Powder group, 56.16% for the comparator group); ≤7.0% (16.34%, TI Inhalation Powder group; 15.98%, comparator group); and ≤6.5% (7.43%, TI Inhalation Powder group; 7.31%, comparator group).

The reduction in HbA1c was comparable between groups and sustained over 52 weeks. Subjects in the TI arm dropped to 8.21 (SD 1.15) % at Week 14 from a baseline of 8.41 (SD 0.92) %; the reduction was maintained at Week 52 (8.20 [SD 1.22]%). Subjects in the insulin aspart arm dropped to 8.07 (SD 1.09) % at Week 14 from a baseline of 8.48 (SD 0.97) %; the reduction was maintained at Week 52 (7.99 [SD 1.07]%).

When the analysis of the change from baseline in HbA1c was corrected for the last 3 months of insulin glargine exposure in an ANCOVA model, no effect due to glargine exposure was found.

Over the 52-week treatment period, fasting plasma glucose (FPG) levels decreased significantly ($p=0.0012$) in the TI Inhalation Powder group compared to FPG levels in subjects using insulin aspart, despite similar dose levels of basal insulin in both groups at both start and end points of the trial. In the TI Inhalation Powder group, mean FPG decreased 44.9 (SD 104.7) mg/dL from 187.6 (SD 85.1) mg/dL at baseline to 140.1 (SD 72.1) mg/dL at the end of the treatment period, compared to a smaller drop of 23.4 (SD 103.1) mg/dL from 180.8 (SD 86.9) mg/dL at baseline to 161.3 (SD 68.2) mg/dL over the same period in the comparator group.

A secondary efficacy endpoint was the percentage of subjects with a 2-hour postprandial plasma glucose (PPG) <140 mg/dL and <180 mg/dL after a meal challenge. Subjects with 2-hour PPG values in both categories were comparable in each treatment group at Weeks 26 and 52. Absolute values for PPG $C_{max}$ at Baseline and Week 52 were the same in both treatment groups.

Subjects in the TI Inhalation Powder group lost an average of 0.5 kg over the 52-week treatment period compared to an average gain of 1.4 kg observed in the comparator group. The difference between groups was statistically significant ($p<0.0001$) with a treatment difference of −1.8 kg. The mean change from Baseline (Week 0) in body weight was not statistically significant for the TI arm ($p=0.1102$), while the mean body weight gain for the insulin aspart arm was significant ($p<0.0001$).

Overall, comparable levels of HbA1c and postprandial blood glucose levels were achieved in both arms of the trial; however TI Inhalation Powder-treated subjects did so in the context of weight neutrality and with more effective control of fasting blood glucose.

TI Inhalation Powder was well-tolerated over 52 weeks of treatment. The safety profile of TI Inhalation Powder was similar to that observed in earlier trials in the TI Inhalation Powder clinical development program; no safety signals emerged over the course of the trial. No pulmonary neoplasms were reported. There was no statistical difference between TI Inhalation Powder treatment and comparator with respect to change from baseline in $FEV_1$ (forced expiratory volume in one second), FVC (forced vital capacity), and TLC (total lung capacity). The most common adverse events in the trial in TI Inhalation Powder-treated subjects were mild to moderate hypoglycemia and transient, mild, non-productive cough.

Figure 12:
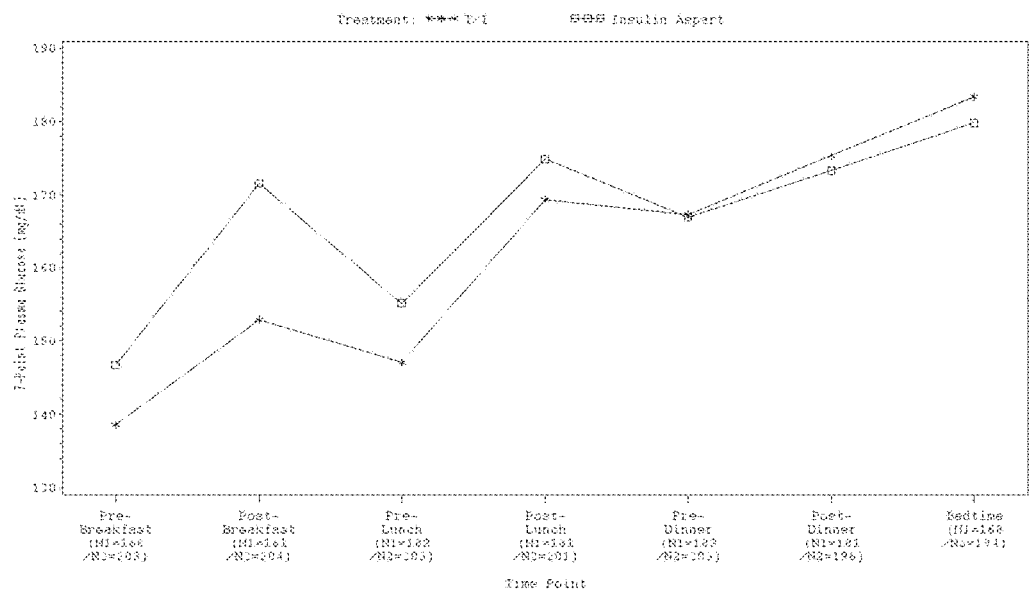
FIG. 12 is a graph of data from a study comparing usage of insulin-FDKP and insulin glargine to insulin aspart and insulin glargine presenting 7-point blood glucose profiles in the $52^{nd}$ week of the study.
Figure 13:
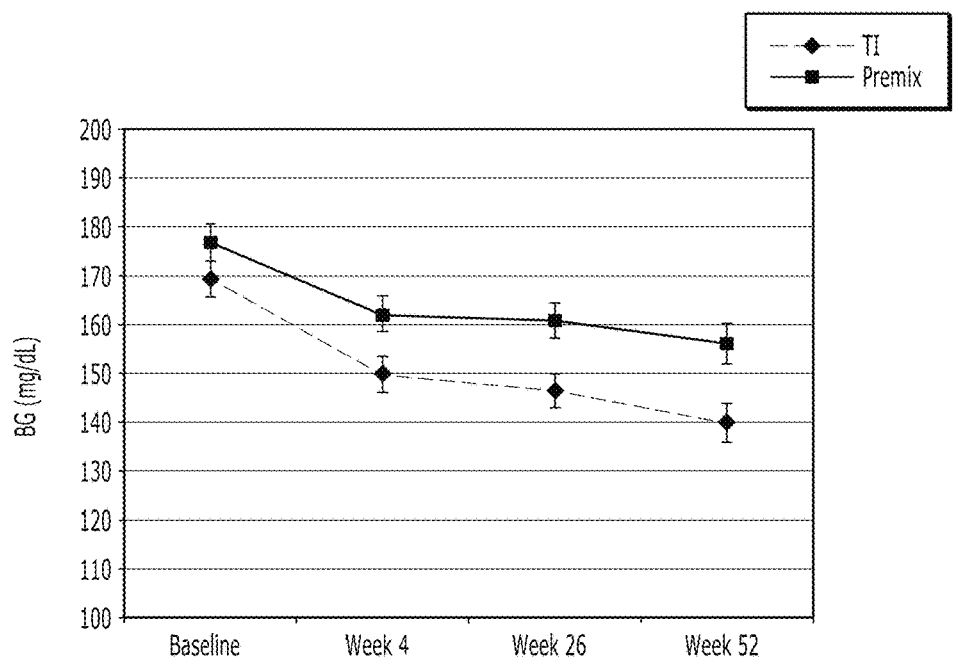
FIG. 13 is a graph depicting data from experiments measuring fasting blood glucose levels in blood samples from subjects treated with subcutaneous injections of a basal insulin (insulin glargine/LANTUS®) at bedtime, and insulin-FDKP administered prandially by pulmonary inhalation. The graph also shows data of a comparison group, i.e., subjects treated with NOVOLOG® mix 70/30 (premix) at breakfast and dinner as recommended by the manufacturer. The subjects were all diagnosed as patients with suboptimally controlled type 2 diabetes, who had been previously treated with regimens of subcutaneous insulins with or without anti-hyperglycemic agents.

Seven-point BG profiles were derived from HBGM; data collected at all specified time points are presented in FIG. 12 for the ITT and PP Populations, respectively. No inferential statistics were performed.

FIG. 12 presents the 7-point BG profile at Week 52 for both treatment arms. Pre-breakfast baseline values were lower in the TI arm as expected from the Week 52 FPG values: 139.1 (SD 72.6) mg/dL for the TI arm vs. 49.5 (SD 80.2) mg/dL for the aspart arm. From pre-breakfast to pre-lunch, BG values were lower in the TI arm. However, from post-lunch through bedtime, mean daily BG values were similar in both treatment groups. Concordant results were observed in the PP Population (data not shown). There was a parallel and steady increase in BG from pre-dinner to bedtime in both treatment arms that was likely a result of the suboptimal dosing with insulin glargine. Bedtime dosing with insulin glargine may not provide full 24-hour coverage in all subjects with type 1 diabetes (Barnett A. Vascular Health and Risk Management 2: 59-67, 2006) (LANTUS® was administered once daily by label). Although there was a rise in underlying baseline blood glucose in both treatment arms both in the evening and throughout the day the effect is more pronounced in the TI treatment arm.

Example 3

Figure 14:
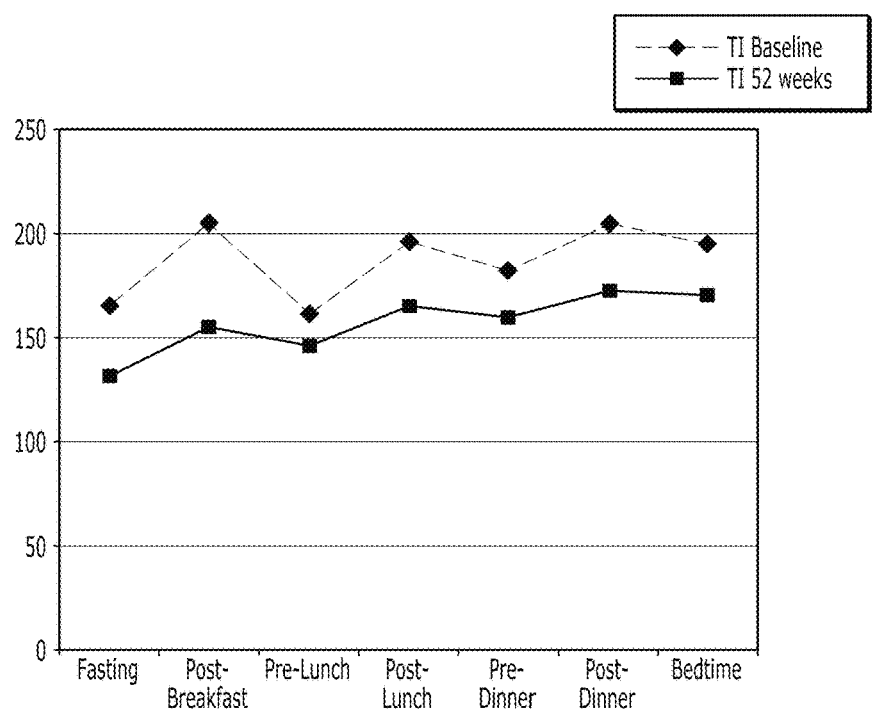
FIG. 14 is a graph depicting data from experiments measuring mean blood glucose levels from samples taken at seven points during the day, i.e., fasting, post-breakfast, pre-lunch, post-lunch, pre-dinner, post-dinner and bedtime for three days during the indicated week, in subjects treated with insulin glargine at bedtime and prandial insulin-FDKP by pulmonary inhalation at the first week of treatment, (hatched lines; baseline) and during the 52nd week (solid line) of treatment. The data show a rise in blood glucose concentration in subjects with type 2 diabetes throughout the day, however, at 52 weeks, the data indicate that the blood glucose levels were significantly lower that at the onset of the treatments and better controlled.

A Prospective, Multi-Center, Open-Label, Randomized, Controlled Clinical Trial Comparing the Efficacy and Safety in Subjects With T2 DM Receiving SC Basal Insulin and Prandial Inhalation of TI vs. SC Premixed Insulin Therapy Over a 52-Week Treatment Period and 4-Wk Follow-up This trial compared the efficacy as expressed by change in HbA1c over a 52-week period of prandial administration of TI Inhalation Powder in combination with basal insulin therapy (TI group) versus a premix of intermediate-acting and rapid-acting insulin (comparator group) in subjects with suboptimally controlled type 2 diabetes, previously treated with regimens of sc insulins±oral anti-hyperglycemic agents. The reduction in HbA1c was comparable between TI+basal insulin and premixed insulin. The percent of responders for an end of study HbA1c≤7.0% was comparable and not statistically different between the TI+basal insulin and premixed insulin groups. Notably fasting blood glucose was reduced significantly by treatment with TI+basal insulin as compared to premixed insulin (see FIG. 13) Additionally both fasting blood glucose and glucose excursions were reduced for the TI+basal insulin group between the beginning and end of the treatment period (See FIG. 14). As noted in Example 2 baseline blood glucose levels trended upward over the course of the day for TI+basal insulin (see FIG. 14).

Example 4

Figure 15:
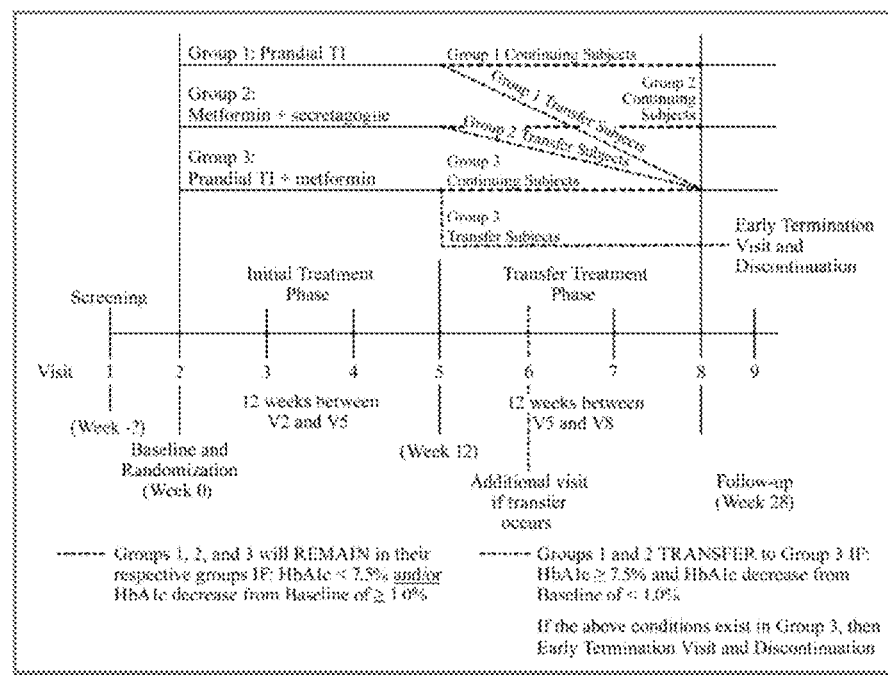
FIG. 15 depicts the trial design of a clinical study comparing prandial TI (insulin-FDKP) (Group 1) with metformin+a secretagogue (Group 2) and prandial TI+metformin (Group 3).

This study was a phase 3, 24-week, open-label trial designed to evaluate the efficacy and safety of prandial TECHNOSPHERE®/Insulin (insulin-FDKP, TI) alone or in combination with metformin versus metformin and a secretagogue, a current standard of care regimen, in subjects with type 2 diabetes mellitus sub-optimally controlled on combination metformin and secretagogue. FIGS. 15 and 16 depict the trial design of the clinical study and the baseline demographics of patients enrolled in the study. Subjects were randomized 1:1:1 to one of the 3 treatment groups and received anti-diabetic treatment based on their randomization group for the first 12 weeks; the subsequent 12 weeks of the trial were considered an observational period.

The trial design was unusual in that there was not a formal run-in period to titrate study medications. Subjects had a total of only 12 weeks of treatment to titrate to an effective dose of study medication before an assessment of the primary efficacy endpoint was conducted. Subjects with continued sub-optimal control after 12 weeks of therapy, in any of the 3 treatment groups, were required to either switch to TI+metformin or discontinue participation in the trial. The total duration of the treatment period was 24 weeks.

This was not a treat-to-target trial and investigators were not given a specific HbA1c or fasting plasma glucose (FPG) goal to treat to. Investigators were allowed to titrate TI at their clinical discretion with upper limits specified for pre-prandial, postprandial, and bedtime blood glucose, but without a fixed dose schedule. Although the protocol allowed titration of up to 90 U TI per meal, the mean per meal dose of TI was ~65 U at trial endpoint, suggesting that investigators may have been reluctant to titrate upward.

In a head-to-head comparison of prandial TI alone or in combination with metformin vs. a commonly used antihyperglycemic regimen. All three treatment groups showed statistically and clinically significant reductions in HbA1c levels over the course of the study. TI was comparable with respect to HbA1c and FPG reduction and significantly more effective with respect to postprandial control—both in formal meal challenges and in self monitored glucose profiles. Subjects treated with prandial TI alone or in combination with metformin over 24 weeks had mean weight loss. The ultrarapid pharmacokinetics of TI may synchronize insulin levels with the post-meal rise in blood glucose, thereby preventing over-insulinization and concomitant weight gain.

TI alone or in combination with metformin was well-tolerated over 24 weeks of treatment. FIGS. 17-28 depict the results of the study. The safety profile of TI was similar to that observed in earlier trials in the TI clinical development program; no safety signals emerged over the course of the trial. Very low rates of severe hypoglycemia were observed in all treatment groups with no cases occurring in patients treated with TI alone or with oral hypoglycemics and in 2% of patients when TI and metformin were combined. Even with such marked reductions in HbA1c overall, no increases in weight were seen. Detailed assessment of pulmonary safety including FEv1 and DLCO over the 24 weeks of the study showed no difference in pulmonary function between patients inhaling TI and those on oral therapy alone.

TI+Metformin

For those subjects that completed the trial, prandial TI+metformin provided a clinically significant mean reduction from baseline in HbA1c (−1.68 [1.0]%) after 24 weeks of treatment, comparable to that of a standard anti-hyperglycemic regimen. However, TI+metformin provided statistically superior postprandial control compared to metformin+secretagogue after 12 and 24 weeks of treatment and a comparable mean reduction from baseline in FPG after 24 weeks. There was mean weight loss (−0.75 kg) over 24 weeks in this treatment group and an overall incidence of mild-to-moderate hypoglycemia of 35.0%.

TI Alone

For those subjects that completed the trial, prandial TI alone was successful in providing a clinically significant mean reduction from baseline in HbA1c (1.82 [1.1]%) after 24 weeks of treatment. The change from baseline was numerically superior to the standard anti-hyperglycemic regimen of metformin+secretagogue. At trial endpoint, TI alone provided significantly more effective postprandial control than comparator with a comparable mean reduction from baseline in FPG. There was net weight loss (−0.04 kg) over 24 weeks in this treatment group and an overall incidence of mild-to-moderate hypoglycemia of 27.6%.

Metformin+Secretagogue

Figure 17:
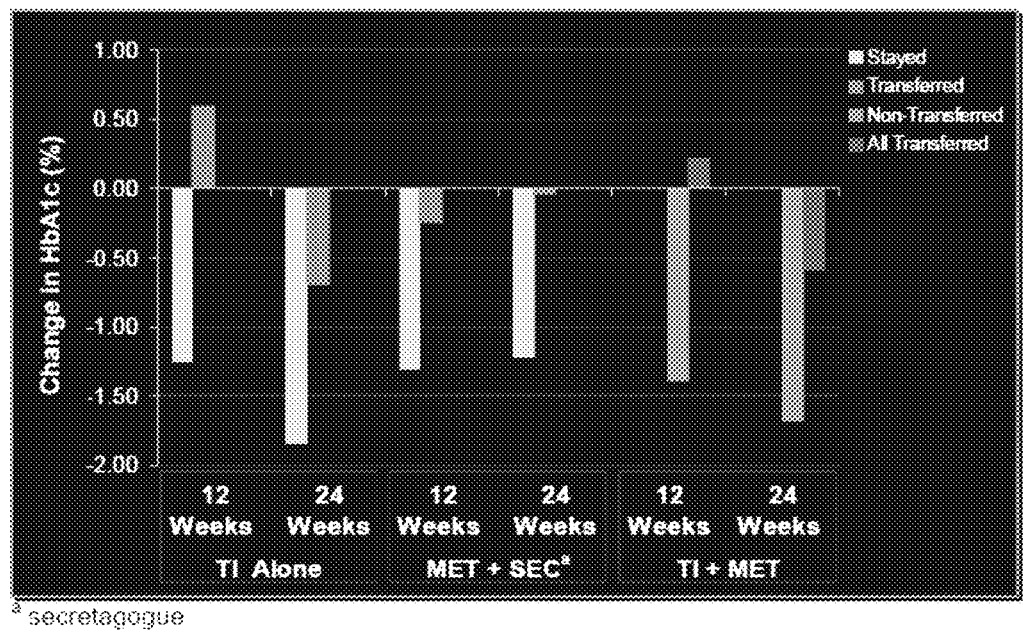
FIG. 17 depicts lowering of HbA1c at 12 and 24 weeks after treatment with TI alone, TI and metformin, or metformin and a secretagogue. The terms "stayed," "transferred," "non-transferred," and "all transferred" are defined in FIG. 15.
Figure 18:
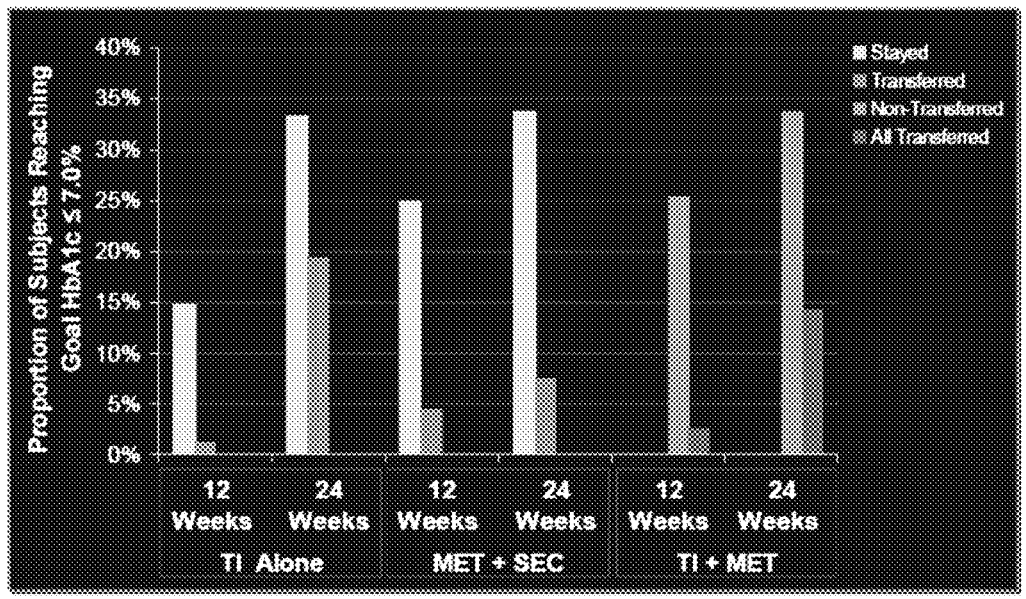
FIG. 18 depicts the proportion of patients reaching their HbA1c goal of ≤7% at 12 and 24 weeks after treatment with TI alone, TI and metformin, or metformin and a secretagogue.
Figure 19:
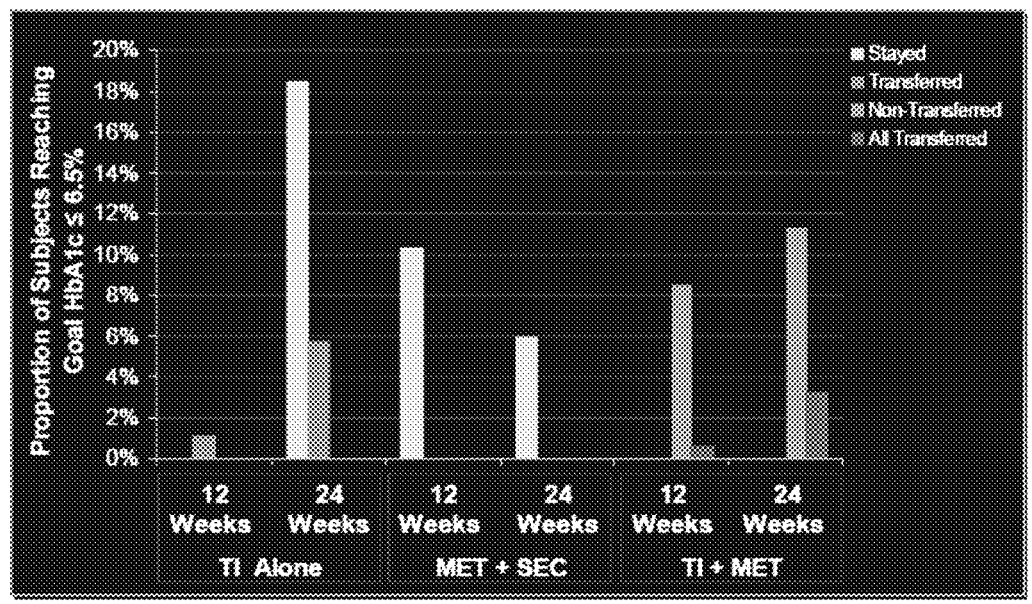
FIG. 19 depicts the proportion of patients reaching their HbA1c goal of ≤6.5% at 12 and 24 weeks after treatment with TI alone, TI and metformin, or metformin and a secretagogue.
Figure 20:
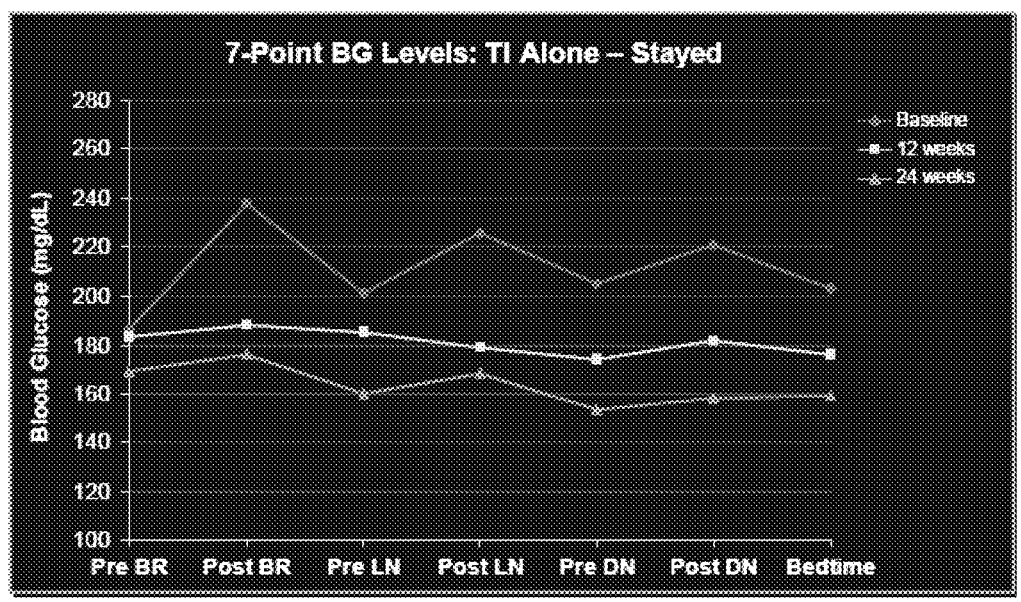
FIG. 20 depicts blood glucose levels after 12 and 24 weeks of treatment with TI alone.
Figure 21:
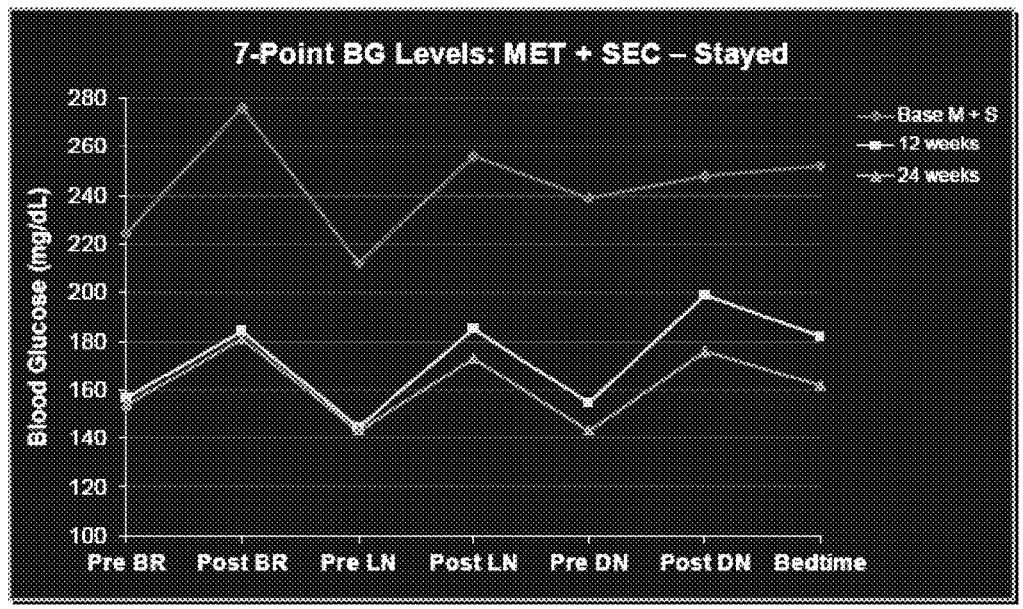
FIG. 21 depicts blood glucose levels after 12 and 24 weeks of treatment with metformin and a secretagogue.
Figure 22:
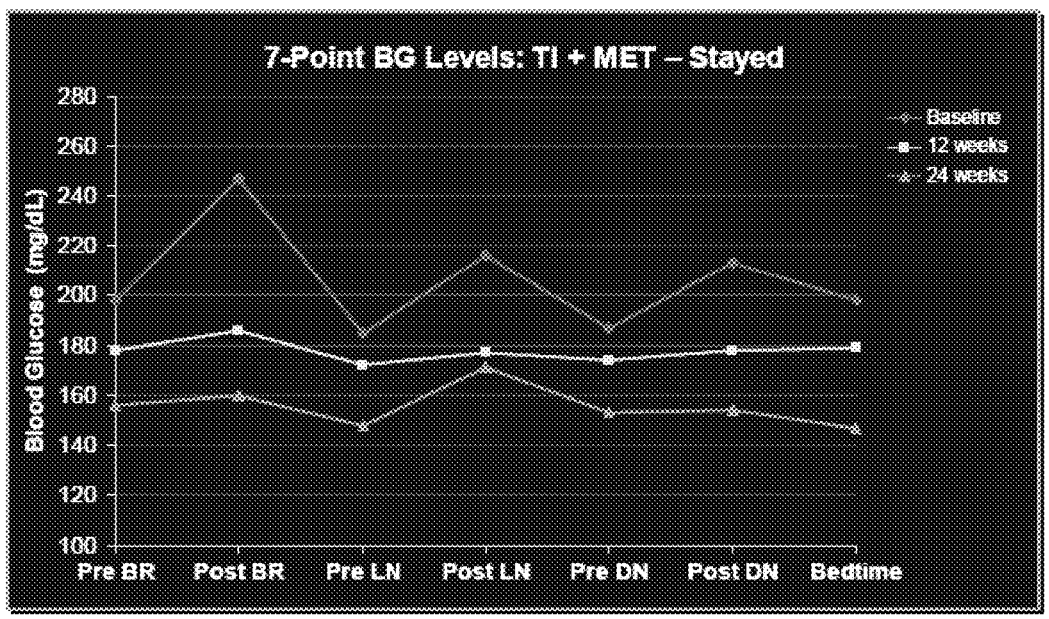
FIG. 22 depicts blood glucose levels after 12 and 24 weeks of treatment with TI and metformin.

For those subjects that completed the trial, metformin+secretagogue was successful in providing a clinically significant mean reduction from baseline in HbA1c (1.23 [1.1]%) after 24 weeks, but with significantly less effective postprandial control than the TI arms (FIGS. 17 and 18). The mean reduction from baseline in FPG and body weight was similar to that observed for the TI+metformin arm (FIGS. 21-22). The overall incidence of mild-to-moderate hypoglycemia was 20.8%.

Figure 23:
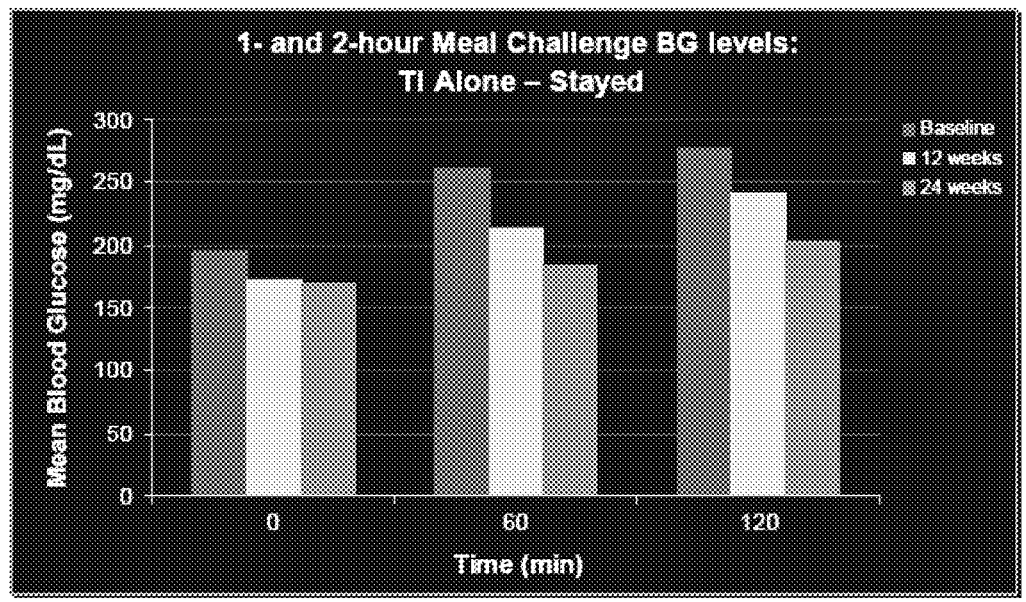
FIG. 23 depicts 1- and 2-hour postprandial blood glucose levels after 12 and 24 weeks of treatment with TI alone.
Figure 24:
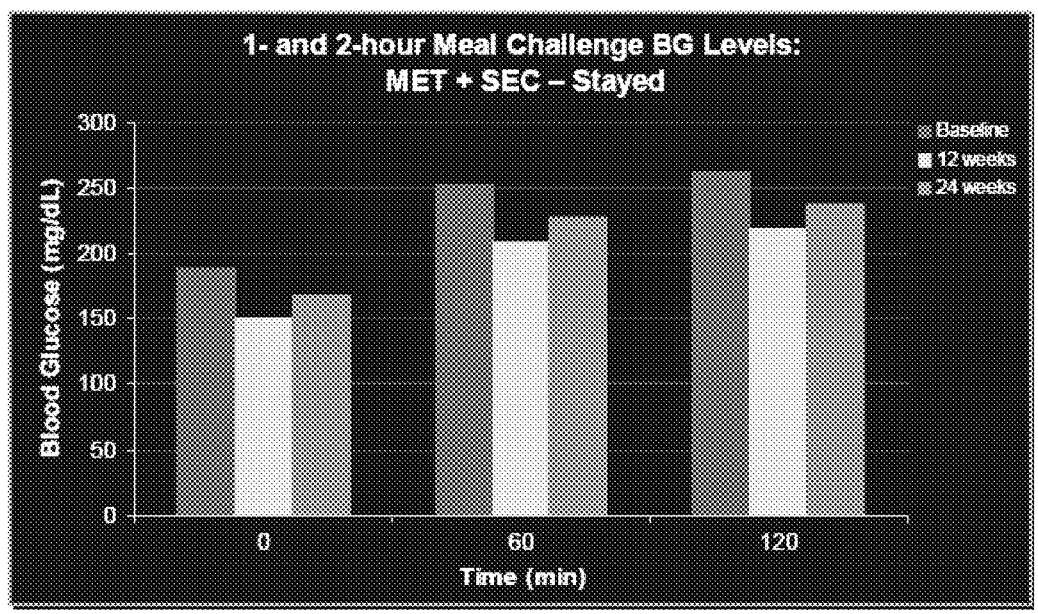
FIG. 24 depicts 1- and 2-hour postprandial blood glucose levels after 12 and 24 weeks of treatment with metformin and a secretagogue.
Figure 25:
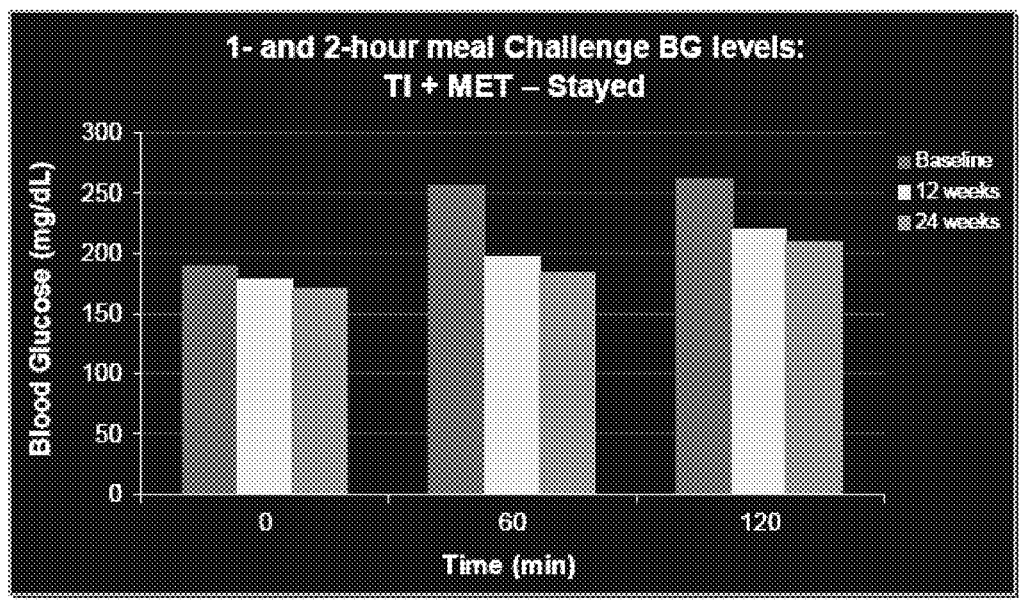
FIG. 25 depicts 1- and 2-hour postprandial blood glucose levels after 12 and 24 weeks of treatment with TI and metformin.
Figure 26:
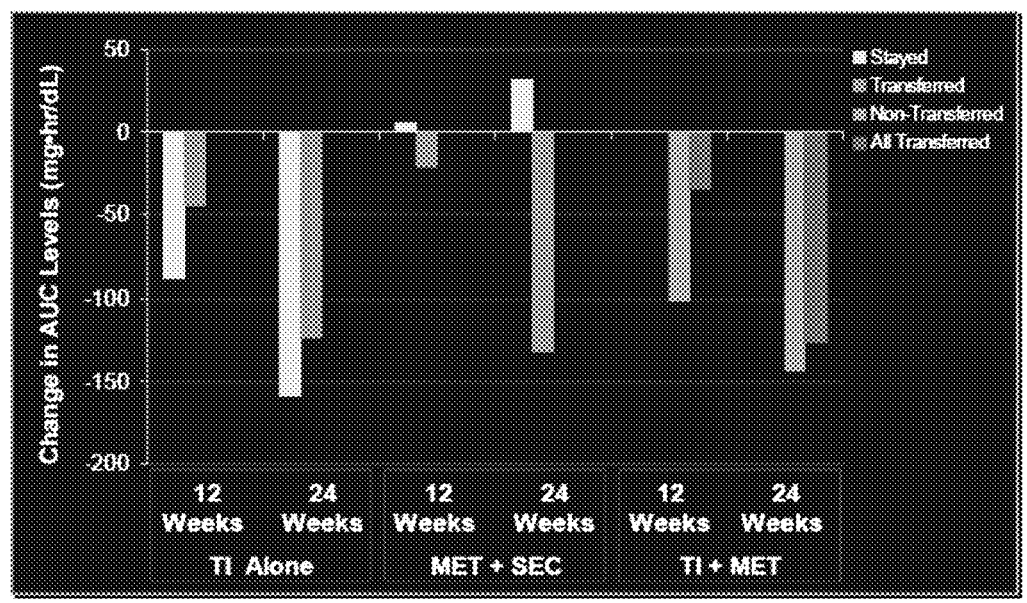
FIG. 26 depicts changes in postprandial glucose excursions (measured as change in AUC levels (mg·hr/dL) after 12 and 24 weeks of treatment with metformin and a secretagogue.
Figure 27:
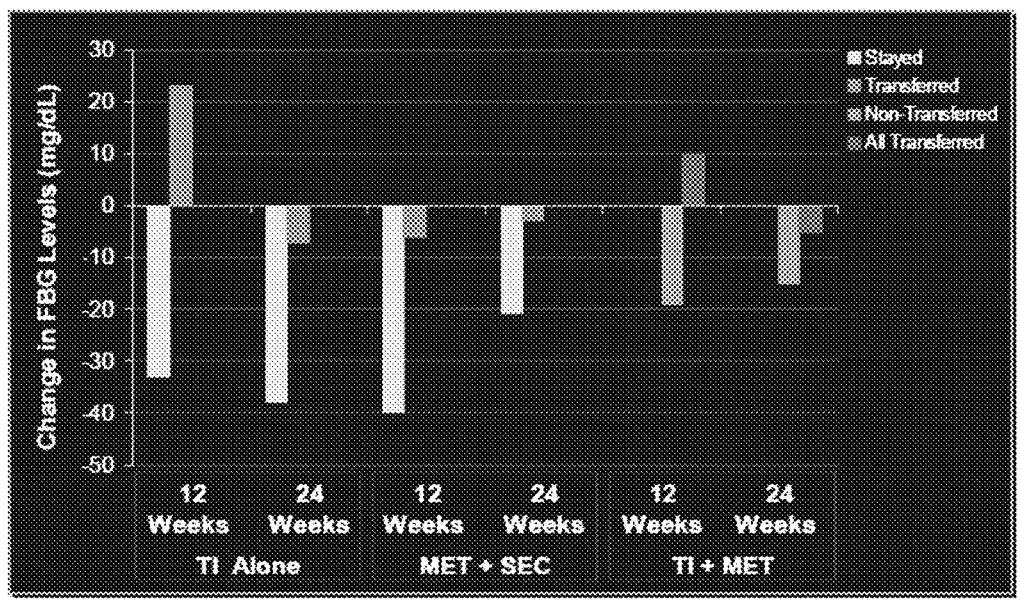
FIG. 27 depicts fasting blood glucose levels at 12 and 24 weeks after treatment with TI alone, TI and metformin, or metformin and a secretagogue.
Figure 28:
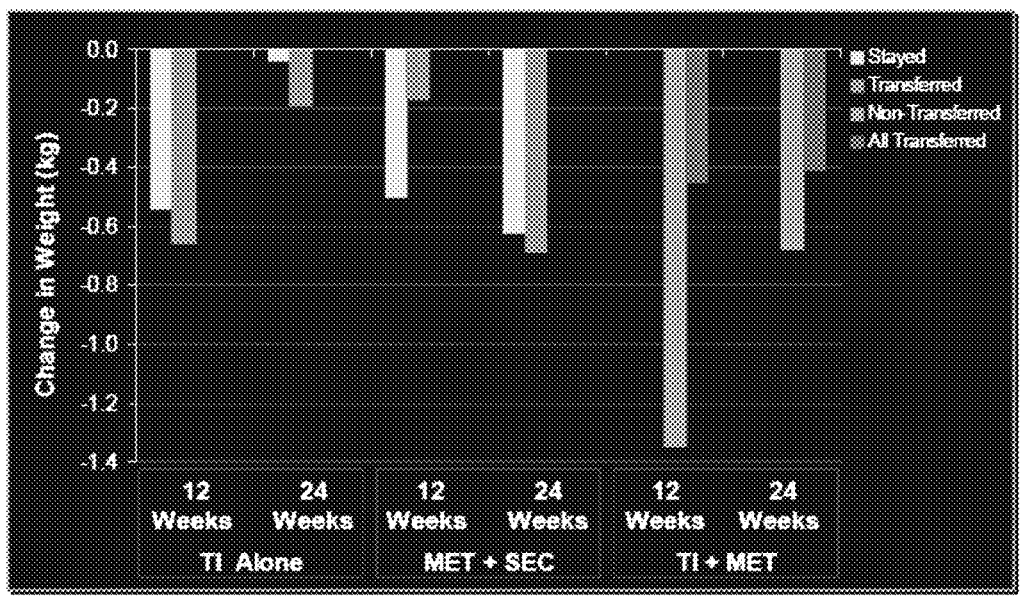
FIG. 28 depicts changes in weight at 12 and 24 weeks after treatment with TI alone, TI and metformin, or metformin and a secretagogue

Prandial TI alone or in combination with metformin significantly lowers HbA1c levels over the course of 12 and 24 weeks (FIGS. 23-25). This is achieved by controlling blood glucose levels over a 24 hour period as demonstrated by 7-point blood glucose levels. TI's main effect is by reducing post-prandial blood glucose excursion as evidenced by reductions in 1 and 2-hour post-prandial glucose levels, AUC and Cmax. The data from this trial support the use of prandial TI in combination with metformin in subjects with type 2 diabetes who require improvements in both postprandial and FPG (FIGS. 26-28). They also indicate a potential for use of prandial TI as monotherapy in subjects with type 2 diabetes who require an improvement in postprandial glycemic control but who have adequate control with respect to FPG.

The majority of patients with type 2 diabetes will eventually require treatment with insulin in order to maintain glycemic control. Treatment with prandial TI alone or in combination with metformin provides effective glycemic control with no weight gain. This is particularly important for patients with type 2 diabetes who are often overweight or obese.

SUMMARY

The data demonstrate that TI alone or in combination with metformin clinically and significantly reduced HbA1c over 12 and 24 weeks without weight gain. TI alone or in combination with metformin controls overall daily blood glucose levels better than metformin+secretagogue based on 7-point blood glucose levels.

The data also demonstrate that TI alone or in combination with metformin controls postprandial glucose excursions better than metformin+secretagogue (1) at 1-hr and 2-hr in meal challenge tests; (2) AUC levels at 12 and 24 weeks; (3) 1-hr and 2-hr postprandial glucose levels (<180 mg/dL) at 12 and/or 24 weeks; and (4) 1-hr and 2-hr postprandial glucose levels (<140 mg/dL) at 12 and/or 24 weeks.

In addition, TI alone or in combination with metformin lowers fasting blood glucose at 12 and 24 weeks.

Overall, incidence of hypoglycemia was low in all treatment groups.

Moreover, mean changes from baseline in lung function tests including FEV1, FVC, TLC and DLco-HB1 for the TI alone and TI+metformin groups were not significantly different from the metformin+secretagogue group at week 12 or week24

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating pre-meal hyperglycemia in a patient in need of treatment who is monitored for pre-meal blood glucose levels for 10 days comprising: regularly administering a split dose of an ultra rapid acting insulin formulation, the split dose including an initial dose taken at mealtime and a second dose of between 10% to 100% of the initial dosage taken 30 to 150 minutes after beginning a meal; wherein when pre-meal blood glucose level for a next meal had been regularly greater than 120 mg/dl.

2. The method of claim 1, wherein the second dose is taken 60-150 minutes after beginning a meal.

3. The method of claim 2, wherein the second dose is taken 90-150 minutes after beginning a meal.

4. The method of claim 1, wherein said regularly greater than 120 mg/dl comprises pre-meal blood glucose levels of greater than 140 mg/dl for a majority of the pre-meal blood glucose tests within a given time period.

5. The method of claim 1, wherein the pre-meal blood glucose is regularly greater than 150 mg/dl.

6. The method of claim 5, wherein the pre-meal blood glucose is regularly greater than 160 mg/dl.

7. A method of treating hyperglycemia in a patient whose pre-meal blood glucose is greater than 140 mg/dl, comprising: administering a mealtime dose, then administering a secondary dose of an ultra rapid acting insulin formulation 30 to 120 minutes after the mealtime dose comprising between 10% to 100% of an initial dose, wherein the secondary dose is titrated so that median blood glucose 1 to 2 hours after the secondary dose is less than 180 mg/dl.

8. The method of claim 7 wherein the secondary dose is administered to a patient in which increasing the dosage of the mealtime dose produces an undesirably lesser, non-proportional reduction is blood glucose as compared to an unincreased mealtime dosage.

9. The method of claim 7, wherein the ultra rapid acting insulin formulation comprises 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, or 3,6-di(fumaryl-4-aminobutyl)-2,5-diketopiperazine.

10. The method of claim 9, wherein the ultra rapid acting insulin formulation comprises 3,6-di(fumaryl-4-aminobutyl)-2,5-diketopiperazine.

11. The method of claim 10, wherein the ultra rapid acting insulin comprises human insulin.

12. The method of claim 11, wherein administration is by inhalation.

* * * * *